(12) United States Patent
Peyronel

(10) Patent No.: US 8,314,109 B2
(45) Date of Patent: Nov. 20, 2012

(54) 6-HETEROCYCLIC-IMIDAZO[1,2-α]PYRIDINE-2-CARBOXAMIDE DERIVATIVES, PREPARATION AND THERAPEUTIC USE THEREOF

(75) Inventor: Jean-Francois Peyronel, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/828,374

(22) Filed: Jul. 1, 2010

(65) Prior Publication Data

US 2010/0317675 A1    Dec. 16, 2010

Related U.S. Application Data

(63) Continuation of application No. PCT/FR2008/001836, filed on Dec. 31, 2008.

(30) Foreign Application Priority Data

Jan. 2, 2008 (FR) ................... 08 00005

(51) Int. Cl.
| | | |
|---|---|---|
| *A61K 31/506* | (2006.01) | |
| *C07D 471/04* | (2006.01) | |
| *A61K 31/437* | (2006.01) | |
| *A61P 25/28* | (2006.01) | |
| *A61P 29/00* | (2006.01) | |
| *A61P 19/10* | (2006.01) | |
| *A61P 35/00* | (2006.01) | |
| *A61P 25/16* | (2006.01) | |
| *A61P 25/18* | (2006.01) | |
| *A61P 25/24* | (2006.01) | |
| *A61P 25/30* | (2006.01) | |

(52) U.S. Cl. ......... 514/256; 514/300; 546/121; 544/333
(58) Field of Classification Search .................. 514/256, 514/300; 546/121; 544/333
See application file for complete search history.

(56) References Cited

U.S. PATENT DOCUMENTS

| 7,704,989 B2 * | 4/2010 | El-Ahmad et al. ....... 514/210.21 |
| 2010/0168155 A1 | 7/2010 | El-Ahmad et al. |

FOREIGN PATENT DOCUMENTS

| EP | 0436831 A2 | 7/1991 |
| FR | 2638161 A1 | 4/1990 |
| FR | 2903107 A1 | 1/2008 |
| WO | WO2004/050659 A1 | 6/2004 |
| WO | WO2004/103991 A1 | 12/2004 |

OTHER PUBLICATIONS

Enguehard-Gueiffier, Cecile et al., "Convenient Synthesis of Alkenyl-, Alkynyl-, and Allenyl-Substituted Imidazo [1,2-a]pyridines via Palladium-Catalyzed Cross-Coupling Reactions," Helvetica Chimica Acta (2007), vol. 90, pp. 2349-2367.
International Preliminary Report on Patentability dated Sep. 7, 2010 issued in PCT/FR2008/001836.

* cited by examiner

*Primary Examiner* — Niloofar Rahmani
(74) *Attorney, Agent, or Firm* — Kelly Bender; Scully, Scott, Murphy & Presser, P.C.

(57) ABSTRACT

Compounds of formula (I):

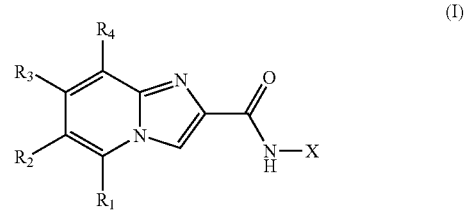

in which:
X, $R_1$, $R_2$, $R_3$ and $R_4$ are as defined in the disclosure, or an acid addition salt thereof; and therapeutic use thereof.

11 Claims, No Drawings

6-HETEROCYCLIC-IMIDAZO[1,2-α] PYRIDINE-2-CARBOXAMIDE DERIVATIVES, PREPARATION AND THERAPEUTIC USE THEREOF

The present invention relates to imidazo[1,2-a]pyridine-2-carboxamide derivatives, to their preparation and to their therapeutic use in the treatment or prevention of diseases involving the nuclear receptors Nurr-1, also known as NR4A2, NOT, TINUR, RNR-1 and HzF3.

One subject of the present invention is the compounds of formula (I):

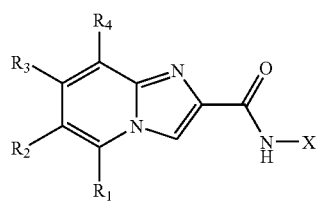

in which:
X represents a phenyl group optionally substituted with one or more groups chosen, independently of each other, from the following atoms or groups: halogen, $(C_1-C_6)$alkoxy, $(C_1-C_6)$alkyl, NRaRb, cyano, $(C_1-C_6)$alkoxycarbonyl, the groups $(C_1-C_6)$alkyl and $(C_1-C_6)$alkoxy being optionally substituted with one or more halogen atoms;

$R_1$ represents a hydrogen atom, a halogen, a group $(C_1-C_6)$alkoxy, a group $(C_1-C_6)$alkyl or a group NRaRb, the alkyl and alkoxy groups possibly being substituted with one or more halogen, hydroxyl or amino, or a group $(C_1-C_6)$alkoxy;

$R_2$ represents an unsaturated, partially saturated or totally saturated aromatic heterocyclic group, optionally substituted with one or more groups chosen, independently of each other, from the following atoms or groups: hydroxyl, $(C_1-C_6)$alkoxy, halogen, cyano, NRaRb, —CO—$R_5$, —CO—$NR_6R_7$, —CO—O—$R_8$, —$NR_9$—CO—$R_{10}$, a group $(C_1-C_6)$alkyl, which is itself optionally substituted with one or more hydroxyl or NRaRb, an oxido group;

$R_3$ represents a hydrogen atom, a group $(C_1-C_6)$alkyl, a group $(C_1-C_6)$alkoxy or a halogen atom;

$R_4$ represents a hydrogen atom, a group $(C_1-C_4)$alkyl, a group $(C_1-C_4)$alkoxy or a fluorine atom;

$R_5$ represents a hydrogen atom, a phenyl group or a group $(C_1-C_6)$alkyl;

$R_6$ and $R_7$, which may be identical or different, represent a hydrogen atom or a group $(C_1-C_6)$alkyl or form, with the nitrogen atom, a 4- to 7-membered ring optionally including another heteroatom chosen from N, O and S;

$R_8$ represents a group $(C_1-C_6)$alkyl;

$R_9$ and $R_{10}$, which may be identical or different, represent a hydrogen atom or a group $(C_1-C_6)$alkyl;

Ra and Rb are, independently of each other, hydrogen or $(C_1-C_6)$alkyl or form, with the nitrogen atom that bears them, a 4- to 7-membered ring, optionally including another heteroatom chosen from N, O and S;

with the exception of N-(4-bromophenyl)-6-(1-methyl-2-piperidinyl)imidazo[1,2-a]pyridine-2-carboxamide;
in the form of the base or of an acid-addition salt.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention. These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

N-(4-Bromophenyl)-6-(1-methyl-2-piperidinyl)imidazo[1,2-a]pyridine-2-carboxamide, which is specifically excluded from formula (I) according to the invention, is cited in chemical libraries under the number RN=797785-86-5.

In the context of the present invention, the following definitions apply:
a halogen atom: a fluorine, a chlorine, a bromine or an iodine;
an alkyl group: a linear, branched or cyclic saturated aliphatic group, optionally substituted with a linear, branched or cyclic saturated alkyl group. Examples that may be mentioned include methyl, ethyl, propyl, isopropyl, butyl, isobutyl, tert-butyl, cyclopropyl, cyclobutyl, cyclopentyl, cyclohexyl, methylcyclopropyl, etc. groups;
an alkenyl group: a linear or branched, monounsaturated or polyunsaturated aliphatic group comprising, for example, one or two ethylenic unsaturations;
an alkoxy group: a radical —O-alkyl in which the alkyl group is as defined previously;
a heterocyclic group: an unsaturated, partially saturated or totally saturated monocyclic or bicyclic aromatic group comprising from 5 to 10 atoms including 1 to 4 heteroatoms chosen from N, O and S. Examples of heterocyclic groups that may be mentioned include: pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine, triazine, pyrrolopyrrole, pyrroloimidazole, pyrrolopyrazole, pyrrolotriazole, imidazoimidazole, imidazopyrazole, imidazotriazole, indole, isoindole, benzimidazole, indazole, indolizine, benzofuran, isobenzofuran, benzothiophene, benzo[c]thiophene, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, tetrazolopyrimidine, pyrrolopyrazine, imidazopyrazine, pyrazolopyrazine, triazolopyrazine, tetrazolopyrazine, pyrrolopyridazine, imidazopyridazine, pyrazolopyridazine, triazolopyridazine, tetrazolopyridazine, pyrrolotriazine, imidazotriazine, pyrazolotriazine, triazolotriazine, tetrazolotriazine, furopyridine, furopyrimidine, furopyrazine, furopyridazine, furotriazine, oxazolopyridine, oxazolopyrimidine, oxazolopyrazine, oxazolopyridazine, oxazolotriazine, isoxazolopyridine, isoxazolopyrimidine, isoxazolopyrazine, isoxazolopyridazine, isoxazolotriazine, oxadiazolopyridine, oxadiazolopyrimidine, oxadiazolopyrazine, oxadiazolopyridazine, oxadiazolotriazine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, thiazolotriazine, isothiazolopyridine, isothiazolopyrimidine, isothiazolopyrazine, isothiazolopyridazine, isothiazolotriazine, thiadiazolopyridine, thiadiazolopyrimidine, thiadiazolopyrazine, thiadiazolopyridazine, thiadiazolotriazine, benzothiazole, benzoisothiazole, benzothiadiazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrimidotriazine, pyrazinopyrazine, pyrazinopyridazine, pyrazinotriazine, pyridazinopyridazine, pyridazinotriazine; these groups possibly being partially unsaturated or saturated.

Examples of heterocyclic groups that may also be mentioned include dioxolane and indazoline groups.

This heterocyclic group at $R_2$ is not bonded to the imidazo[1,2-a]pyridine via a nitrogen if it is a nitrogenous saturated monocyclic heterocyclic group.

Various subgroups of compounds, which also form part of the invention, are defined hereinbelow.

Among the compounds that are subjects of the invention, a first group of compounds is constituted by the compounds of formula (I) as defined previously, in which:

X represents a phenyl group optionally substituted with one or more halogen atoms or cyano groups;

the other groups being as defined previously.

Among the compounds that are subjects of the invention, a second group of compounds is constituted by the compounds of formula (I) as defined previously, in which:

X represents a phenyl group optionally substituted with one or more fluorine or chlorine atoms or cyano groups;

the other groups being as defined previously.

Among the compounds that are subjects of the invention, a third group of compounds is constituted by the compounds of formula (I) as defined previously, in which $R_2$ represents an unsaturated, partially saturated or totally saturated monocyclic or bicyclic aromatic heterocyclic group, comprising from 5 to 10 atoms including 1 to 4 heteroatoms chosen from N, O and S, with the exclusion of a piperidine group, the said heterocycle being optionally substituted with one or more groups chosen, independently of each other, from the following atoms or groups: hydroxyl, $(C_1-C_6)$alkoxy, halogen, cyano, NRaRb, —CO—$R_5$, —CO—$NR_6R_7$, —CO—O—$R_8$, —$NR_9$—CO—$R_{10}$, an oxido group, a group $(C_1-C_6)$alkyl, which is itself optionally substituted with one or more hydroxyl or group NRaRb;

the other groups being as defined previously.

Among the compounds that are subjects of the invention, a fourth group of compounds is constituted by the compounds of formula (I) as defined previously, in which:

$R_2$ represents a pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine group; optionally substituted with one or more groups chosen from the following atoms or groups: hydroxyl, $(C_1-C_6)$alkoxy, oxido, halogen, —NRaRb, $(C_1-C_6)$alkyl which is itself optionally substituted with a hydroxyl group, Ra and Rb are, independently of each other, hydrogen or $(C_1-C_6)$alkyl.

Among the compounds that are subjects of the invention, a fifth group of compounds is constituted by the compounds of formula (I) as defined previously, in which:

$R_2$ represents a dioxolane, pyridine, imidazole, pyrazole, triazole, pyrrole, furan, imidazoline, thiophene, pyrazine, pyrimidine or thiazole group; optionally substituted with one or more groups chosen from the following atoms or groups: hydroxyl, $(C_1-C_6)$alkoxy, oxido, halogen, —NRaRb, $(C_1-C_6)$alkyl which is itself optionally substituted with a hydroxyl group, Ra and Rb are, independently of each other, hydrogen or $(C_1-C_6)$alkyl, the other groups being as defined previously.

Among the compounds that are subjects of the invention, a sixth group of compounds is constituted by the compounds of formula (I) as defined previously, in which:

$R_2$ represents an indole, isoindole, benzimidazole, indazole, indolizine, benzofuran, isobenzofuran, benzothiophene, benzo[c]thiophen, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, tetrazolopyrimidine, pyrrolopyrazine, imidazopyrazine, pyrazolopyrazine, triazolopyrazine, tetrazolopyrazine, pyrrolopyridazine, imidazopyridazine, pyrazolopyridazine, triazolopyridazine, tetrazolopyridazine, pyrrolotriazine, imidazotriazine, pyrazolotriazine, triazolotriazine, tetrazolotriazine, furopyridine, furopyrimidine, furopyrazine, furopyridazine, furotriazine, oxazolopyridine, oxazolopyrimidine, oxazolopyrazine, oxazolopyridazine, oxazolotriazine, isoxazolopyridine, isoxazolopyrimidine, isoxazolopyrazine, isoxazolopyridazine, isoxazolotriazine, oxadiazolopyridine, oxadiazolopyrimidine, oxadiazolopyrazine, oxadiazolopyridazine, oxadiazolotriazine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, thiazolotriazine, isothiazolopyridine, isothiazolopyrimidine, isothiazolopyrazine, isothiazolopyridazine, isothiazolotriazine, thiadiazolopyridine, thiadiazolopyrimidine, thiadiazolopyrazine, thiadiazolopyridazine, thiadiazolotriazine, benzothiazole, benzoisothiazole or benzothiadiazole group; optionally substituted with one or more groups chosen from the following atoms or groups: hydroxyl, $(C_1-C_6)$alkoxy, oxido, halogen, —NRaRb, $(C_1-C_6)$alkyl which is itself optionally substituted with a hydroxyl group, Ra and Rb are, independently of each other, hydrogen or $(C_1-C_6)$alkyl;

the other groups being as defined previously.

Among the compounds that are subjects of the invention, a seventh group of compounds is constituted by the compounds of formula (I) as defined previously, in which:

$R_2$ represents an indole group optionally substituted with one or more groups chosen from the following atoms or groups: hydroxyl, $(C_1-C_6)$alkoxy, oxido, halogen, —NRaRb, $(C_1-C_6)$alkyl which is itself optionally substituted with a hydroxyl group, Ra and Rb are, independently of each other, hydrogen or $(C_1-C_6)$alkyl;

the other groups being as defined previously.

Among the compounds that are subjects of the invention, an eighth group of compounds is constituted by the compounds of formula (I) as defined previously, in which:

$R_2$ represents a dioxolane, pyridine, imidazole, pyrazole, triazole, pyrrole, furan, oxazole, indole, imidazoline, thiophene, pyrazine, pyrimidine or thiazole group, optionally substituted with one or more hydroxyl, methyl, hydroxymethyl, methoxy, oxido, halogen or $NH_2$ groups, the other groups being as defined previously.

Among the compounds that are subjects of the invention, a ninth group of compounds is constituted by the compounds of formula (I) as defined previously, in which $R_1$ represents a hydrogen atom or a group $(C_1-C_6)$alkyl;

the other groups being as defined previously.

Among the compounds that are subjects of the invention, a tenth group of compounds is constituted by the compounds of formula (I) as defined previously, in which $R_1$ represents a hydrogen atom or a methyl group;

the other groups being as defined previously.

Among the compounds that are subjects of the invention, an eleventh group of compounds is constituted by the compounds of formula (I) as defined previously, in which $R_3$ and $R_4$ represent a hydrogen atom;

the other groups being as defined previously.

Among the compounds that are subjects of the invention, a twelfth group of compounds is constituted by the compounds of formula (I) as defined previously, in which:

X represents a phenyl group optionally substituted with one or more fluorine or chlorine atoms or with a cyano group;

$R_2$ represents a dioxolane, pyridine, imidazole, pyrazole, triazole, pyrrole, furan, oxazole, indole, imidazoline, thiophene, pyrazine, pyrimidine or thiazole group, optionally substituted with one or more hydroxyl, methyl, hydroxymethyl, methoxy, oxido, halogen or $NH_2$ groups, $R_1$ represents a hydrogen atom or a methyl group;

$R_3$ and $R_4$ represent a hydrogen atom;

in the form of the base or of an acid-addition salt.

Among the compounds of formula (I) that are subjects of the invention, a thirteenth group of compounds is constituted of compounds for which:

X represents a phenyl group optionally substituted with one or more fluorine atoms;

$R_2$ represents a pyridine, furan, dioxolane, imidazole, pyrazole, triazole, pyrrole, thiazole, oxazole, pyrazine, pyrimidine, thiophene, indole or imidazoline group, these groups being optionally substituted with a hydroxymethyl, $NH_2$, methyl, methoxy, hydroxyl or oxido group or a fluorine atom;

$R_1$ represents a hydrogen atom or a methyl group;

$R_3$ and $R_4$ represent a hydrogen atom, in the form of the base or of an acid-addition salt.

Among the compounds of formula (I) that are subjects of the invention, mention may be made especially of the following compounds:

6-(1,3-Dioxolan-2-yl)-N-phenylimidazo[1,2-a]pyridine-2-carboxamide

N-Phenyl-6-(pyrid-3-yl)imidazo[1,2-a]pyridine-2-carboxamide

N-Phenyl-6-(pyrid-2-yl)imidazo[1,2-a]pyridine-2-carboxamide

6-[5-(Hydroxymethyl)pyrid-3-yl]-N-phenylimidazo[1,2-a]pyridine-2-carboxamide

6-[4-(Hydroxymethyl)pyrid-2-yl]-N-phenylimidazo[1,2-a]pyridine-2-carboxamide and the hydrochloride (1:1) thereof 6-(6-Aminopyrid-2-yl)-N-phenylimidazo[1,2-a]pyridine-2-carboxamide and the hydrochloride (1:1) thereof 6-(1H-Imidazol-4-yl)-N-phenylimidazo[1,2-a]pyridine-2-carboxamide and the hydrochloride (1:1) thereof N-Phenyl-6-(1H-pyrazol-3-yl)imidazo[1,2-a]pyridine-2-carboxamide N-Phenyl-6-(1H-1,2,4-triazol-3-yl)imidazo[1,2-a]pyridine-2-carboxamide N-Phenyl-6-(1H-pyrrol-3-yl)imidazo[1,2-a]pyridine-2-carboxamide 6-(2-Methyl-1H-imidazol-4-yl)-N-phenylimidazo[1,2-a]pyridine-2-carboxamide 6-(3-Furyl)-N-phenylimidazo[1,2-a]pyridine-2-carboxamide 6-(1H-Imidazol-1-yl)-N-phenylimidazo[1,2-a]pyridine-2-carboxamide and the trifluoroacetate (1:1) thereof 6-(Oxazol-5-yl)-N-phenylimidazo[1,2-a]pyridine-2-carboxamide 6-(2-Aminothiazol-4-yl)-N-phenylimidazo[1,2-a]pyridine-2-carboxamide 6-(2-Methyl-1,3-dioxolan-2-yl)-N-phenylimidazo[1,2-a]pyridine-2-carboxamide 6-(4,5-Dihydro-1H-imidazol-2-yl)-N-phenylimidazo[1,2-a]pyridine-2-carboxamide and the hydrochloride (1:1) thereof 6-(6-Methoxypyrid-2-yl)-N-phenylimidazo[1,2-a]pyridine-2-carboxamide 5-Methyl-N-phenyl-6-(pyrid-2-yl)imidazo[1,2-a]pyridine-2-carboxamide 6-(2-Amino-1H-imidazol-4-yl)-N-phenylimidazo[1,2-a]pyridine-2-carboxamide and the trifluoroacetate (1:1) thereof 6-(2-Aminothiazol-5-yl)-N-phenylimidazo[1,2-a]pyridine-2-carboxamide 6-(6-Hydroxypyrid-2-yl)-N-phenylimidazo[1,2-a]pyridine-2-carboxamide N-Phenyl-6-(1H-1,2,3-triazol-4-yl)imidazo[1,2-a]pyridine-2-carboxamide N-(3,5-Difluorophenyl)-6-(furan-3-yl)imidazo[1,2-a]pyridine-2-carboxamide N-(3-Fluorophenyl)-6-(furan-3-yl)imidazo[1,2-a]pyridine-2-carboxamide 6-(2-Furyl)-N-phenylimidazo[1,2-a]pyridine-2-carboxamide 6-[6-(Hydroxymethyl)pyrid-2-yl]-N-phenylimidazo[1,2-a]pyridine-2-carboxamide and the hydrochloride (1:1) thereof 6-(1-Oxidopyrid-3-yl)-N-phenylimidazo[1,2-a]pyridine-2-carboxamide and the hydrochloride (1:1) thereof N-Phenyl-6-(1H-pyrazol-4-yl)imidazo[1,2-a]pyridine-2-carboxamide 6-(1H-Imidazol-2-yl)-N-phenylimidazo[1,2-a]pyridine-2-carboxamide hydrochloride (1:1)

6-(1-Methyl-1H-imidazol-4-yl)-N-phenylimidazo[1,2-a]pyridine-2-carboxamide 6-(Oxazol-2-yl)-N-phenylimidazo[1,2-a]pyridine-2-carboxamide N-(3,5-Difluorophenyl)-6-(pyrid-2-yl)imidazo[1,2-a]pyridine-2-carboxamide N-Phenyl-6-(pyrid-4-yl)imidazo[1,2-a]pyridine-2-carboxamide 6-(1H-Indol-3-yl)-N-phenylimidazo[1,2-a]pyridine-2-carboxamide N-Phenyl-6-(thiophen-2-yl)imidazo[1,2-a]pyridine-2-carboxamide N-Phenyl-6-(pyrazin-2-yl)imidazo[1,2-a]pyridine-2-carboxamide 6-(1-Oxidopyrid-2-yl)-N-phenylimidazo[1,2-a]pyridine-2-carboxamide N-Phenyl-6-(pyrimidin-5-yl)imidazo[1,2-a]pyridine-2-carboxamide N-Phenyl-6-(thien-3-yl)imidazo[1,2-a]pyridine-2-carboxamide
6-(5-Fluoro-2-furyl)-N-phenylimidazo[1,2-a]pyridine-2-carboxamide
N-(3-Fluorophenyl)-6-(pyrid-2-yl)imidazo[1,2-a]pyridine-2-carboxamide
N-(2-Fluorophenyl)-6-(pyrid-2-yl)imidazo[1,2-a]pyridine-2-carboxamide
N-(2,5-Difluorophenyl)-6-(pyrid-2-yl)imidazo[1,2-a]pyridine-2-carboxamide
N-(2,3-Difluorophenyl)-6-(pyrid-2-yl)imidazo[1,2-a]pyridine-2-carboxamide
6-(6-Aminopyrid-2-yl)-N-(3-fluorophenyl)imidazo[1,2-a]pyridine-2-carboxamide
N-(3-Fluorophenyl)-6-(1H-pyrrol-3-yl)imidazo[1,2-a]pyridine-2-carboxamide
N-(3-Fluorophenyl)-6-(1H-pyrazol-3-yl)imidazo[1,2-a]pyridine-2-carboxamide
N-(3-Fluorophenyl)-6-(furan-2-yl)imidazo[1,2-a]pyridine-2-carboxamide
N-(3-Fluorophenyl)-6-(oxazol-2-yl)imidazo[1,2-a]pyridine-2-carboxamide
N-Phenyl-6-(pyrimidin-2-yl)imidazo[1,2-a]pyridine-2-carboxamide
N-(3-Fluorophenyl)-6-(1H-imidazol-4-yl)imidazo[1,2-a]pyridine-2-carboxamide
N-(3-Fluorophenyl)-6-(1H-1,2,4-triazol-3-yl)imidazo[1,2-a]pyridine-2-carboxamide
6-(2-Aminothiazol-4-yl)-N-(3-fluorophenyl)imidazo[1,2-a]pyridine-2-carboxamide
N-(3-Fluorophenyl)-6-(1H-1,2,3-triazol-4-yl)imidazo[1,2-a]pyridine-2-carboxamide
N-(3-Fluorophenyl)-6-(1H-pyrazol-4-yl)imidazo[1,2-a]pyridine-2-carboxamide
N-(3-Fluorophenyl)-6-[5-(hydroxymethyl)furan-2-yl]imidazo[1,2-a]pyridine-2-carboxamide
6-[2-(Hydroxymethyl)-1H-imidazol-4-yl]-N-phenylimidazo[1,2-a]pyridine-2-carboxamide
N-(3,5-Difluorophenyl)-6-(6-methylpyrid-2-yl)imidazo[1,2-a]pyridine-2-carboxamide
N-(2-Chlorophenyl)-6-(pyrid-2-yl)imidazo[1,2-a]pyridine-2-carboxamide
N-(3,5-Difluorophenyl)-6-(1H-pyrrol-3-yl)imidazo[1,2-a]pyridine-2-carboxamide
N-(2-Fluorophenyl)-6-(1H-pyrrol-3-yl)imidazo[1,2-a]pyridine-2-carboxamide
N-(2,5-Difluorophenyl)-6-(1H-pyrrol-3-yl)imidazo[1,2-a]pyridine-2-carboxamide
N-(2,3-Difluorophenyl)-6-(1H-pyrrol-3-yl)imidazo[1,2-a]pyridine-2-carboxamide
N-(3,5-Difluorophenyl)-6-(1H-pyrazol-3-yl)imidazo[1,2-a]pyridine-2-carboxamide
N-(2-Fluorophenyl)-6-(furan-2-yl)imidazo[1,2-a]pyridine-2-carboxamide
N-(2,5-Difluorophenyl)-6-(furan-2-yl)imidazo[1,2-a]pyridine-2-carboxamide
N-(2,3-Difluorophenyl)-6-(furan-2-yl)imidazo[1,2-a]pyridine-2-carboxamide
N-(2-Chlorophenyl)-6-(furan-2-yl)imidazo[1,2-a]pyridine-2-carboxamide
N-(2,5-Difluorophenyl)-6-(oxazol-2-yl)imidazo[1,2-a]pyridine-2-carboxamide
N-(2-Chlorophenyl)-6-(oxazol-2-yl)imidazo[1,2-a]pyridine-2-carboxamide
N-(2-Fluorophenyl)-6-(furan-3-yl)imidazo[1,2-a]pyridine-2-carboxamide
N-(2,5-Difluorophenyl)-6-(furan-3-yl)imidazo[1,2-a]pyridine-2-carboxamide
N-(2,3-Difluorophenyl)-6-(furan-3-yl)imidazo[1,2-a]pyridine-2-carboxamide
N-(2-Chlorophenyl)-6-(furan-3-yl)imidazo[1,2-a]pyridine-2-carboxamide
N-(2,3-Difluorophenyl)-6-[5-(hydroxymethyl)furan-2-yl]imidazo[1,2-a]pyridine-2-carboxamide
N-(2-Fluorophenyl)-6-(1H-1,2,4-triazol-3-yl)imidazo[1,2-a]pyridine-2-carboxamide
N-(2-Chlorophenyl)-6-(1H-1,2,4-triazol-3-yl)imidazo[1,2-a]pyridine-2-carboxamide
N-(2-Cyanophenyl)-6-(pyrid-2-yl)imidazo[1,2-a]pyridine-2-carboxamide
6-(6-Aminopyrid-2-yl)-N-(3,5-difluorophenyl)imidazo[1,2-a]pyridine-2-carboxamide and the dihydrochloride thereof
6-(6-Aminopyrid-2-yl)-N-(2-fluorophenyl)imidazo[1,2-a]pyridine-2-carboxamide and the dihydrochloride thereof
6-(6-Aminopyrid-2-yl)-N-(2,5-difluorophenyl)imidazo[1,2-a]pyridine-2-carboxamide and the dihydrochloride thereof
6-(6-Aminopyrid-2-yl)-N-(2,3-difluorophenyl)imidazo[1,2-a]pyridine-2-carboxamide and the dihydrochloride thereof
6-(6-Aminopyrid-2-yl)-N-(2-chlorophenyl)imidazo[1,2-a]pyridine-2-carboxamide and the dihydrochloride thereof
N-(2-Chlorophenyl)-6-(1H-pyrrol-3-yl)imidazo[1,2-a]pyridine-2-carboxamide
N-(2-Fluorophenyl)-6-(1H-pyrazol-3-yl)imidazo[1,2-a]pyridine-2-carboxamide
N-(2-Chlorophenyl)-6-(1H-pyrazol-3-yl)imidazo[1,2-a]pyridine-2-carboxamide
N-(3,5-Difluorophenyl)-6-(furan-2-yl)imidazo[1,2-a]pyridine-2-carboxamide
N-(3,5-Difluorophenyl)-6-(oxazol-2-yl)imidazo[1,2-a]pyridine-2-carboxamide
N-(2-Fluorophenyl)-6-(oxazol-2-yl)imidazo[1,2-a]pyridine-2-carboxamide
N-(2,3-Difluorophenyl)-6-(oxazol-2-yl)imidazo[1,2-a]pyridine-2-carboxamide
N-(3,5-Difluorophenyl)-6-[5-(hydroxymethyl)furan-2-yl]imidazo[1,2-a]pyridine-2-carboxamide
N-(2,5-Difluorophenyl)-6-[5-(hydroxymethyl)furan-2-yl]imidazo[1,2-a]pyridine-2-carboxamide
N-(2,3-Difluorophenyl)-6-(1H-imidazol-4-yl)imidazo[1,2-a]pyridine-2-carboxamide
N-(2,5-Difluorophenyl)-6-(1H-1,2,4-triazol-3-yl)imidazo[1,2-a]pyridine-2-carboxamide
N-(2,3-Difluorophenyl)-6-(1H-1,2,4-triazol-3-yl)imidazo[1,2-a]pyridine-2-carboxamide
N-(3,5-Difluorophenyl)-6-(1H-1,2,3-triazol-4-yl)imidazo[1,2-a]pyridine-2-carboxamide
N-(2-Fluorophenyl)-6-(1H-1,2,3-triazol-4-yl)imidazo[1,2-a]pyridine-2-carboxamide
N-(2,5-Difluorophenyl)-6-(1H-1,2,3-triazol-4-yl)imidazo[1,2-a]pyridine-2-carboxamide
N-(2-Chlorophenyl)-6-(1H-1,2,3-triazol-4-yl)imidazo[1,2-a]pyridine-2-carboxamide;
and the acid-addition salts thereof.

In accordance with the invention, the compounds of general formula (I) may be prepared according to the process described in Scheme 1.

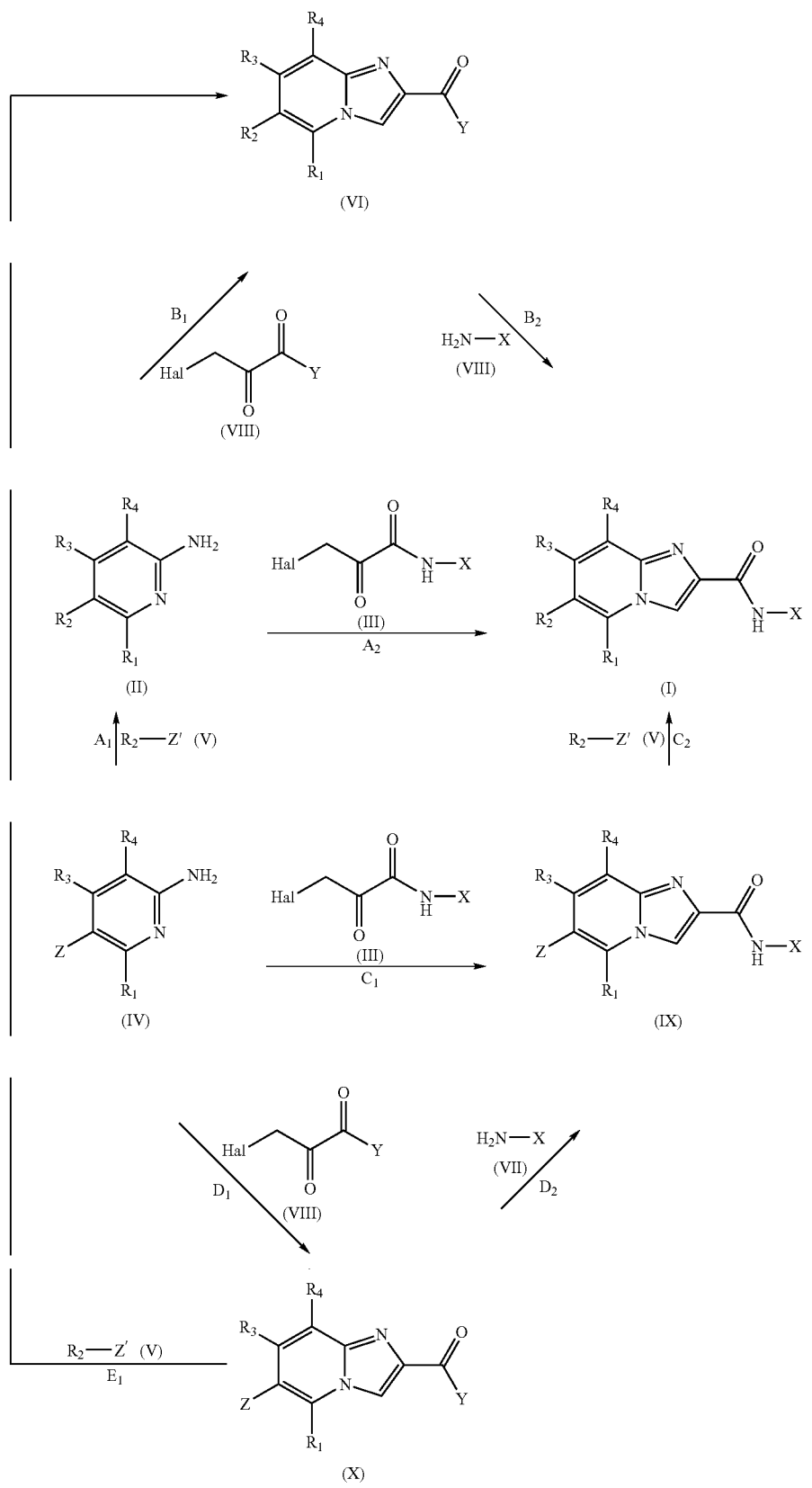
Scheme 1

The first synthetic route (transformation $A_2$) consists in preparing, according to the methods known to those skilled in the art, a 2-aminopyridine of formula (II), in which $R_1$, $R_2$, $R_3$ and $R_4$ are as defined previously, and then in forming the imidazo[1,2-a]pyridine ring by condensation of a halogenated derivative of 2-oxo-N-arylpropionamide (III) in which Hal represents a chlorine, bromine or iodine atom and X is as defined previously, by analogy with the methods described by J-J. Bourguignon et al. in Aust. J. Chem., 50, 719 (1997) and by J. G. Lombardino in J. Org. Chem., 30, 2403 (1965), for example.

The halogenated derivatives of 2-oxo-N-arylpropionamide (III) may be obtained, for example, according to the method described by R. Kluger et al. in J. Am. Chem. Soc., 106, 4017 (1984).

The 2-aminopyridines of formula (II), in which $R_1$, $R_2$, $R_3$ and $R_4$ are as defined previously, may be prepared, for example, via transformation $A_1$, i.e.:

via a coupling reaction of a 2-aminopyridine derivative of formula (IV), in which $R_1$, $R_3$ and $R_4$ are as defined previously and Z represents a boryl, stannyl or silyl group, with a derivative $R_2$—Z' (V) in which $R_2$ is as defined previously, and Z' represents a halogen atom such as bromine or iodine or a sulfonyloxy group, via a coupling reaction of a 2-aminopyridine derivative of formula (IV), in which $R_1$, $R_3$ and $R_4$ are as defined previously and Z represents a halogen atom such as bromine or iodine, with a derivative $R_2$—Z' (V) in which $R_2$ is as defined previously, and Z' represents a reactive group such as a boryl, stannyl or silyl group or a hydrogen atom, or via any other method known to those skilled in the art.

The second synthetic route (transformation $B_2$) consists in coupling an imidazopyridine-2-carboxylic acid or a derivative thereof of formula (VI), in which $R_1$, $R_2$, $R_3$ and $R_4$ are as defined previously, Y represents a hydroxyl group, a halogen atom or a group $(C_1-C_6)$alkoxy, with an arylamine X—$NH_2$ of formula (VII), in which X is as defined previously, according to methods known to those skilled in the art. Thus, the acid may be converted beforehand into a reactive derivative thereof such as an acid halide, anhydride, mixed anhydride or activated ester, and then reacted with the amine (VII) in the presence of a base such as diisopropylethylamine, triethylamine or pyridine, in an inert solvent such as THF, DMF or dichloromethane. The coupling may also be performed in the presence of a coupling agent such as CDI, EDCI, HATU or HBTU under the same conditions without isolating the reactive intermediate. Alternatively, the amine (VII) may be reacted with an ester of the acid of formula (VI) in the presence of a catalyst such as trimethylaluminium according to the method of Weinreb, S. et al. (Tet. Lett. (1977), 18, 4171), or zirconium tert-butoxide.

The imidazopyridine-2-carboxylic acid derivatives of formula (VI), in which $R_1$, $R_2$, $R_3$ and $R_4$ are as defined previously and Y is $(C_1-C_6)$alkoxy, hydroxyl or halogen, are prepared by condensation of a 2-aminopyridine of formula (II), in which $R_1$, $R_2$, $R_3$ and $R_4$ are as defined previously, with a 3-halo-2-oxopropionic acid of formula (VIII) in which Hal represents a halogen and Y is $(C_1-C_6)$alkoxy, under conditions similar to those used for the condensation of a derivative of formula (II) with a derivative of formula (III), followed, where appropriate, by conversion of the ester to the acid and then to the acid chloride or another reactive derivative (transformation $B_1$).

The third synthetic route (transformation $C_2$) consists in coupling a derivative of general formula (IX), in which $R_1$, $R_3$, $R_4$ and X are as defined previously and Z represents a halogen atom such as bromine or iodine, a sulfonyloxy group or a reactive group such as boryl, stannyl or silyl, with a derivative of formula $R_2$—Z' (V) in which $R_2$ is as defined previously, and Z' represents a reactive group such as a boryl, stannyl or silyl group or a hydrogen atom when Z represents a halogen atom or a sulfonyloxy group, or Z' represents a halogen atom such as bromine or iodine when Z represents a reactive group such as a boryl, stannyl or silyl group or a hydrogen atom.

The derivatives of general formula (IX) in which $R_1$, $R_3$, $R_4$, X and Z are as defined previously may be prepared:

by condensation of a 2-aminopyridine of formula (IV), in which $R_1$, $R_3$, $R_4$ and Z are as defined previously, with a 2-oxo-N-arylpropionamide derivative (III) in which Hal represents a chlorine, bromine or iodine atom and X is as defined previously (transformation $C_1$), according to methods mentioned for the conversion of a compound of formula (II) into a compound of formula (I) or by amidation of an imidazopyridine-2-carboxylic acid or a derivative thereof of formula (X), in which $R_1$, $R_2$, $R_3$ and $R_4$ are as defined previously, Y represents a hydroxyl group, a halogen atom or a group $(C_1-C_6)$alkoxy, with an arylamine X—$NH_2$ of formula (VII), in which X is as defined previously (transformation $D_2$), according to methods mentioned for the conversion of a compound of formula (VI) into a compound of formula (I).

The imidazopyridine-2-carboxylic acids or derivatives thereof of formula (X), in which $R_1$, $R_3$ and $R_4$ are as defined previously, Y is $(C_1-C_6)$alkoxy, hydroxyl or halogen and Z represents a boryl, stannyl or silyl group or a halogen atom, may be prepared (transformation $D_1$) by condensation of a 2-aminopyridine of formula (IV), in which $R_1$, $R_3$ and $R_4$ are as defined previously and Z represents a boryl, stannyl or silyl group or a halogen atom, with a 3-halo-2-oxopropionic acid ester of formula (VIII), in which Hal represents a halogen and Y is $(C_1-C_6)$alkoxy, under conditions similar to those mentioned previously for the condensation of the 2-aminopyridines of formula (II), with a derivative of formula (VIII) to obtain the imidazopyridine-2-carboxylic acids or derivatives thereof of formula (VI), according to transformation $B_1$, followed, where appropriate, by conversion of the ester to the acid and then to the acid chloride or another reactive derivative.

The imidazopyridine-2-carboxylic acids or derivatives thereof of formula (VI), in which $R_1$, $R_2$, $R_3$ and $R_4$ are as defined previously and Y is $(C_1-C_6)$alkoxy, hydroxyl or halogen, may also be prepared (transformation $E_1$) by coupling a derivative of general formula (X), in which $R_1$, $R_3$, and $R_4$ are as defined previously, Y is $(C_1-C_6)$alkoxy and Z represents a halogen atom such as bromine or iodine, a sulfonyloxy group or a reactive group such as boryl, stannyl or silyl, with a derivative of formula $R_2$—Z' (V), in which $R_2$ is as defined previously, and Z' represents a reactive group such as a boryl, stannyl or silyl group or a hydrogen atom when Z represents a halogen atom or a sulfonyloxy group, or Z' represents a halogen atom such as bromine or iodine when Z represents a reactive group such as a boryl, stannyl or silyl group or a hydrogen atom, followed, where appropriate, by conversion of the ester to the acid and then to the acid chloride or another reactive derivative.

The coupling of the derivatives of formula (IV), (IX) or (X) with the products of formula (V) may be performed via any method known to those skilled in the art, in particular by working in the presence of copper-based or palladium-based catalysts, or ligands such as phosphines, according to or by analogy with the methods described, for example, in the following references and cited references:

for the reactions of Suzuki type: N. Miyaura, A. Suzuki, Chem. Rev., 95, 2457, (1995), for the reactions of Stille type: V. Farina et al., Org. React., 50, 1 (1997), for the reactions of Hiyama type: T. Hiyama et al., Top. Curr. Chem., 2002, 219, 61 (2002), for the reactions of Negishi type: E. Negishi et al., Chem. Rev., 103, 1979 (2003), for the reactions of Bellina type: M. Miura et al., Chem. Lett., 200 (2007).

It is also possible, in order to perform the coupling, to form as intermediates, but without isolating them, organometallic derivatives such as zinc derivatives.

In accordance with the invention, the compounds of general formulae (I), (VI) and (II) may also be prepared according to the processes described in Scheme 2.

be converted, for example, into a thiazolyl, imidazolyl or oxazolyl group by treatment with thiourea, thioamide, guanidine, urea or amide derivatives, an alkynyl group, such as ethynyl, which may be converted into a 1,2,3-triazol-4-yl group, an acyl group such as formyl, which may be converted, for example, into a 1,3-dioxolanyl-2 or oxazolyl group, a cyano group, which may be converted, for example, into a dihydroimidazolyl(2) or 1,3,4-triazol-2-yl group.

The compounds of general formula (XI) may be obtained from the compounds of formula (XII) under the conditions described for the preparation of the compounds (I), from imidazopyridine-2-carboxylic acid derivatives of formula (VI) via the transformations $B_2$.

The imidazopyridine-2-carboxylic acid derivatives of general formula (XII) may be obtained from the aminopyridines of formula (XIII), under the conditions described for the conversion of the aminopyridines of formula (II) into compounds of general formula (I), via transformation $A_2$.

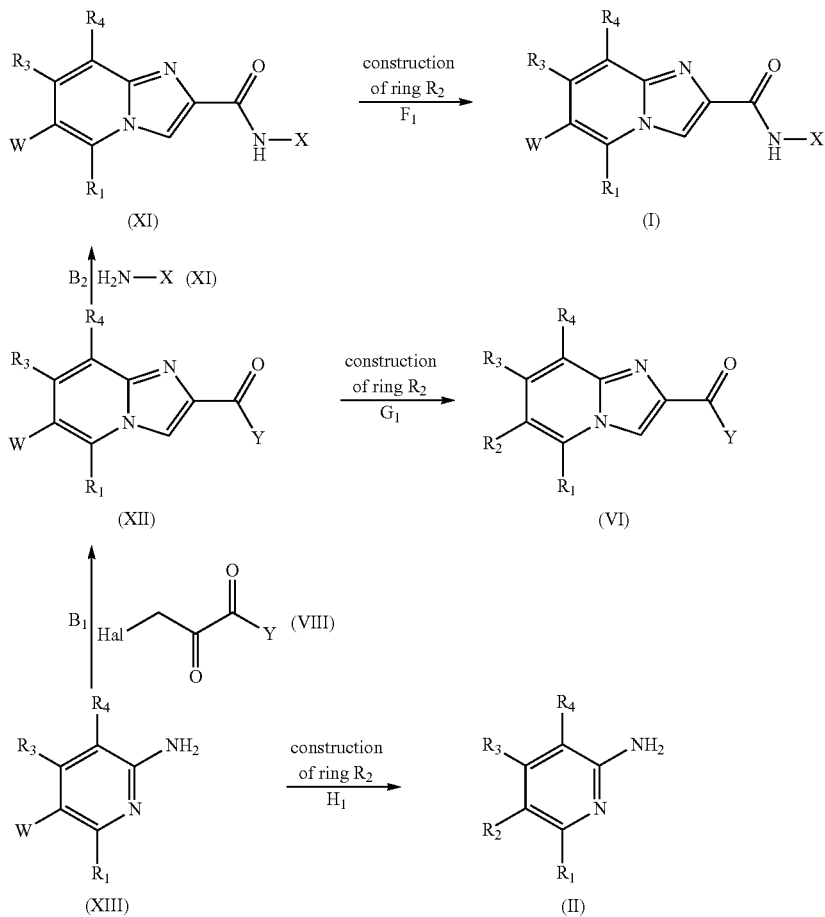

Scheme 2

This synthetic route consists in converting a compound of general formula (XI), (XII) or (XIII), in which $R_1$, $R_3$, $R_4$, X and Y are as defined previously and W represents a precursor group allowing the construction of the heterocycle of formula $R_2$, according to the methods known to those skilled in the art.

By way of example, W may represent:

a 2-haloacyl group such as bromoacetyl, or a 1-halo-2-oxoalkyl group such as 1-bromo-2-oxoethyl, which may The products of formula (I) and the precursors thereof of formula (II), (IV), (VI), (IX) or (X), may be subjected, if desired and if necessary, in order to obtain products of formula (I) or to be converted into other products of formula (I), to one or more of the following transformation reactions, in any order:

a) a reaction for the esterification or amidation of an acid function, b) a reaction for the amidation of an amine function,
c) a reaction for the hydrolysis of an ester function to an acid function,
d) a reaction for the transformation of a hydroxyl function into an alkoxy function,
e) a reaction for the oxidation of an alcohol function to an aldehyde or ketone function,
f) a reaction for the transformation of aldehyde or ketone functions into an alcohol function, via reduction or the action of an organometallic agent such as an organomagnesium reagent,
g) a reaction for the transformation of a nitrile radical into an aldehyde function,
h) a reaction for the transformation of a nitrile radical into a ketone function,
i) a reaction for the oxidation of an alkenyl group to an aldehyde or ketone function,
j) a reaction for the catalytic coupling of an organometallic derivative such as a boron, tin or silicon derivative with a halogenated derivative in order to introduce an alkyl, alkenyl, alkynyl, aryl or hetero aryl substituent,
k) a reaction for the conversion of a primary or secondary amino group into a secondary or tertiary amino group via reductive amination or alkylation,
l) a reaction for the conversion of a halogenated derivative into a secondary or tertiary amino group via substitution—optionally catalytic—with a primary or secondary amine,
m) a reaction for the protection of reactive functions,
n) a reaction for the removal of the protecting groups that may be borne by protected reactive functions,
o) a reaction for salification with a mineral or organic acid or with a base to obtain the corresponding salt,
p) a reaction for the resolution of racemic forms into enantiomers,
the said products of formula (I) thus obtained being, where appropriate, in any possible isomeric form: racemic mixtures, enantiomers and diastereoisomers.

In Schemes 1 and 2, the starting materials and the reagents, when their mode of preparation is not described, are commercially available or described in the literature, or may be prepared according to methods that are described therein or that are known to those skilled in the art.

The examples that follow describe the preparation of certain compounds in accordance with the invention. These examples are not limiting, and serve merely to illustrate the present invention. The numbers of the illustrated compounds refer to those given in the table hereinbelow, which illustrates the chemical structures and the physical properties of a number of compounds according to the invention.

EXAMPLE 1

6-(1,3-Dioxolan-2-yl)-N-phenylimidazo[1,2-a]pyridine-2-carboxamide

To a solution of 137 mg of 6-formyl-N-phenylimidazo[1,2-a]pyridine-2-carboxamide (Intermediate 8) in 5 mL of toluene are added 45 µL of ethylene glycol, 169 mg of para-toluenesulfonic acid and molecular sieves. The mixture is refluxed for 24 hours in a round-bottomed flask equipped with Dean-Stark apparatus, and then cooled, filtered, diluted with 100 mL of dichloromethane and washed with 2N sodium hydroxide and with water. The organic phases are dried and concentrated to dryness to give a mixture of the starting material and of the expected product, which is redissolved in 5 mL of methanol containing 410 µL of ethylene glycol, 130 mg of para-toluenesulfonic acid and molecular sieves. The mixture is heated for 16 hours at reflux and then cooled, filtered and concentrated to dryness. The residue is chromatographed on a silica cartridge, eluting with a 70/30 mixture of dichloromethane and ethyl acetate to give 53 mg of 6-(1,3-dioxolan-2-yl)-N-phenylimidazo[1,2-a]pyridine-2-carboxamide in the form of a white solid.

EXAMPLE 2

N-Phenyl-6-(pyrid-3-yl)imidazo[1,2-a]pyridine-2-carboxamide 150 mg of 6-bromo-N-phenylimidazo[1,2-a]pyridine-2-carboxamide (Intermediate 1), 0.237 g of pyridine-3-boronic acid, 45 mg of tetrakis(triphenylphosphine)palladium, 2 mL of aqueous 2M sodium carbonate solution, 4 mL of acetonitrile and 4 mL of toluene are placed in a microwave tube. The mixture is heated for 20 minutes in a microwave machine set at 150° C., and then cooled and filtered, the insoluble matter being washed with a mixture of methanol and dichloromethane. The combined filtrates are concentrated to dryness under reduced pressure. The residue is concreted with aqueous methanol to give 73 mg of N-phenyl-6-(pyrid-3-yl)imidazo[1,2-a]pyridine-2-carboxamide in the form of an off-white solid.

EXAMPLE 3

N-Phenyl-6-(pyrid-2-yl)imidazo[1,2-a]pyridine-2-carboxamide 230 mg of 6-iodo-N-phenylimidazo[1,2-a]pyridine-2-carboxamide (Intermediate 2), 690 mg of 2-tributylstannylpyridine, 120 mg of tetrakis(triphenylphosphine)palladium and 4 mL of N,N-dimethylformamide are placed in a microwave tube. The reaction mixture is heated for 5 minutes in a microwave machine set at 100° C., and then for 5 minutes at 150° C. and concentrated to dryness. The residue is chromatographed on a silica cartridge, eluting with a mixture of dichloromethane and ethyl acetate. The fractions containing the expected product are combined and evaporated to dryness under reduced pressure to give 56 mg of N-phenyl-6-(pyrid-2-yl)imidazo[1,2-a]pyridine-2-carboxamide in the form of a white solid.

EXAMPLE 4

6-[5-(Hydroxymethyl)pyrid-3-yl]-N-phenylimidazo[1,2-a]pyridine-2-carboxamide 163 mg of 6-trimethylstannyl-N-phenylimidazo[1,2-a]pyridine-2-carboxamide (Intermediate 4), 310 mg of (5-bromopyrid-3-yl)methanol, 66 mg of tetrakis(triphenylphosphine)-palladium and 4 mL of N,N-dimethylformamide are placed in a microwave tube. The reaction mixture is heated for 20 minutes in a microwave machine set at 150° C. and concentrated to dryness. The residue is chromatographed on a silica cartridge, eluting with dichloromethane. The fractions containing the expected product are combined and evaporated to dryness under reduced pressure to give 61 mg of 6-[5-(hydroxymethyl)pyrid-3-yl]-N-phenylimidazo[1,2-a]pyridine-2-carboxamide in the form of a white solid.

EXAMPLE 5

6-[4-(Hydroxymethyl)pyrid-2-yl]-N-phenylimidazo[1,2-a]pyridine-2-carboxamide hydrochloride (1:1)

5.1 6-[4-(Hydroxymethyl)pyrid-2-yl]-N-phenylimidazo[1,2-a]pyridine-2-carboxamide This product is obtained in a manner similar to that of Example 4, replacing the (5-bromopyrid-3-yl)methanol with (2-bromopyrid-4-yl)methanol.

5.2 6-[4-(Hydroxymethyl)pyrid-2-yl]-N-phenylimidazo[1,2-a]pyridine-2-carboxamide hydrochloride (1:1)

A suspension of 117 mg of 6-[4-(hydroxymethyl)pyrid-2-yl]-N-phenylimidazo[1,2-a]pyridine-2-carboxamide in 2 mL of methanol is treated with 0.68 mL of aqueous 0.5 N hydrochloric acid solution. The mixture is stirred for 16 hours at room temperature and then evaporated to dryness under reduced pressure. The solid obtained is triturated in methanol, filtered off and dried to give 91 mg of 6-[4-(hydroxymethyl)pyrid-2-yl]-N-phenylimidazo[1,2-a]pyridine-2-carboxamide hydrochloride (1:1).

EXAMPLE 6

6-(6-Aminopyrid-2-yl)-N-phenylimidazo[1,2-a]pyridine-2-carboxamide hydrochloride (1:1)

236 mg of 6-trimethylstannyl-N-phenylimidazo[1,2-a]pyridine-2-carboxamide (Intermediate 4), 413 mg of 6-bromopyrid-2-ylamine, 95 mg of tetrakis(triphenylphosphine)palladium and 4 mL of N,N-dimethylformamide are placed in a microwave tube. The reaction mixture is heated for 45 minutes in a microwave machine set at 150° C. and concentrated to dryness. The residue is chromatographed on a silica cartridge, eluting with a mixture of dichloromethane and ethyl acetate. The fractions containing the expected product are combined and evaporated to dryness under reduced pressure to give 147 mg of 6-(6-aminopyrid-2-yl)-N-phenylimidazo[1,2-a]pyridine-2-carboxamide in the form of a yellow solid, which product is taken up in a mixture of dioxane and methanol and treated with 112 μL of a 4 M solution of hydrogen chloride in dioxane. After stirring for 1 hour at room temperature, the precipitate is filtered off by suction, washed with dioxane and dried to give 156 mg of 6-(6-aminopyrid-2-yl)-N-phenylimidazo[1,2-a]pyridine-2-carboxamide hydrochloride (1:1) in the form of a pale yellow solid.

EXAMPLE 7

6-(1H-Imidazol-4-yl)-N-phenylimidazo[1,2-a]pyridine-2-carboxamide hydrochloride (1:1)

7.1: 6-(1-Triphenylmethyl-1H-imidazol-4-yl)-N-phenylimidazo[1,2-a]pyridine-2-carboxamide 540 mg of N-phenyl-6-(4,4,5,5-tetramethyl-1,3,2-dioxaborolan-2-yl)imidazo[1,2-a]pyridine-2-carboxamide (Intermediate 5), 13 mL of dioxane, 6.8 mL of 2M sodium carbonate solution, 843 mg of 4-iodo-1-triphenylmethylimidazole and 86 mg of tetrakis(triphenylphosphine)-palladium are placed in a microwave tube. The mixture is heated for 10 minutes in a microwave machine set at 120° C., and then cooled and concentrated under reduced pressure. The residue is taken up in 100 mL of dichloromethane. After washing with water, the organic phase is dried over magnesium sulfate and concentrated to dryness under reduced pressure. The residue is chromatographed on a silica cartridge, eluting with a gradient of cyclohexane and ethyl acetate (from 100/0 to 60/40). The fractions containing the expected product are combined and concentrated to dryness under reduced pressure. The solid is crystallized from acetonitrile. The crystals are washed with acetonitrile and then with ethyl ether and then dried under vacuum to give 342 mg of 6-(1-triphenylmethyl-1H-imidazol-4-yl)-N-phenylimidazo[1,2-a]pyridine-2-carboxamide in the form of a white solid.

$^1$H NMR spectrum (DMSO-d6, δ in ppm): 7.09 (t, J=7.5 Hz, 1H), 7.19 (d, J=8.0 Hz, 6H), 7.33 (t, J=7.5 Hz, 2H), from 7.38 to 7.49 (m, 9H), 7.53 (d, J=1.5 Hz, 1H), 7.57 (d, J=1.5 Hz, 1H), 7.59 (d, J=9.5 Hz, 1H), 7.79 (dd, J=1.5 and 9.5 Hz, 1H), 7.89 (d, J=7.5 Hz, 2H), 8.50 (s, 1H), 9.03 (broad s, 1H), 10.2 (s, 1H).

Mass spectrum (LC-MS-DAD-ELSD): m/z 546 [M+H]$^+$.

7.2: 6-(1H-Imidazol-4-yl)-N-phenylimidazo[1,2-a]pyridine-2-carboxamide hydrochloride (1:1)

A suspension of 270 mg of 6-(1-triphenylmethyl-1H-imidazol-4-yl)-N-phenyl-imidazo[1,2-a]pyridine-2-carboxamide in 4 mL of 2N hydrochloric acid is heated for 30 minutes at 70° C. and then diluted with 2 mL of methanol, heated for 45 minutes at reflux, diluted again by addition of 2 mL of dichloromethane and heated for a further 2 hours at reflux. The reaction mixture is stirred for 60 hours at room temperature. The precipitate is filtered off by suction, washed with methanol, water and then pentane and dried under reduced pressure to give 96 mg of 6-(1H-imidazol-4-yl)-N-phenylimidazo[1,2-a]pyridine-2-carboxamide hydrochloride (1:1) in the form of a white solid.

EXAMPLE 8

N-Phenyl-6-(1H-pyrazol-3-yl)imidazo[1,2-a]pyridine-2-carboxamide 300 mg of 6-iodo-N-phenylimidazo[1,2-a]pyridine-2-carboxamide (Intermediate 2), 4 mL of dioxane, 4 mL of water, 185 mg of 1H-pyrazole-3-boronic acid, 45 mg of [1,1'-bis(diphenylphosphino)ferrocene]dichloropalladium and 1.077 g of caesium carbonate are placed in a microwave tube. The mixture is heated for 20 minutes in a microwave machine set at 160° C., and then cooled, diluted with 20 mL of water and extracted twice with 20 mL of dichloromethane. The combined organic phases are dried over magnesium sulfate, filtered and concentrated to dryness under reduced pressure. The residue is chromatographed on a silica cartridge, eluting with a gradient of dichloromethane and methanol (from 0 to 10%). The fractions containing the expected product are combined and concentrated to dryness under reduced pressure to give 40 mg of N-phenyl-6-(1H-pyrazol-3-yl)imidazo[1,2-a]pyridine-2-carboxamide in the form of a white solid.

EXAMPLE 9

N-Phenyl-6-(1H-1,2,4-triazol-3-yl)imidazo[1,2-a]pyridine-2-carboxamide 250 mg of 6-iodo-N-phenylimidazo[1,2-a]pyridine-2-carboxamide (Intermediate 2), 8 mL of N,N-dimethylformamide, 7.7 mg of palladium acetate, 197 mg of cuprous iodide and 71.3 mg of 1,2,4-triazole are placed in a microwave tube. The reaction mixture is heated for 2.5 hours in a microwave machine set at 200° C. The cooled reaction mixture is filtered, the insoluble matter is rinsed with N,N-dimethylformamide, dichloromethane and methanol and the combined filtrates are concentrated to dryness under reduced pressure. The residue is chromatographed on a silica cartridge, eluting with a 90/10 mixture of dichloromethane and methanol. The fractions containing the pure expected product are combined and evaporated to dryness under reduced pressure to give 40 mg of N-phenyl-6-(1H-1,2,4-triazol-3-yl)imidazo[1,2-a]pyridine-2-carboxamide in the form of a white solid.

EXAMPLE 10

N-Phenyl-6-(1H-pyrrol-3-yl)imidazo[1,2-a]pyridine-2-carboxamide

10.1: N-Phenyl-6-(1-triisopropylsilyl-1H-pyrrol-3-yl)imidazo[1,2-a]pyridine-2-carboxamide This product is obtained in a manner similar to that of Example 8, replacing the 1H-pyrazole-3-b oronic acid with 1-triisopropylsilyl-1H-pyrrol-3-b oronic acid.

$^1$H NMR spectrum (DMSO-d6, δ in ppm): 1.09 (d, J=7.5 Hz, 18H), 1.56 (m, 3H), 6.66 (broad s, 1H), 6.95 (t, J=2.0 Hz, 1H), 7.09 (t, J=7.5 Hz, 1H), 7.33 (t, J=7.5 Hz, 2H), 7.39 (broad s, 1H), 7.61 (d, J=9.5 Hz, 1H), 7.73 (dd, J=1.5 and 9.5 Hz, 1H), 7.89 (d, J=7.5 Hz, 2H), 8.39 (s, 1H), 8.82 (broad s, 1H), 10.15 (s, 1H).

Mass spectrum (LC-MS-DAD-ELSD): m/z 459 [M+H]$^+$

10.2: N-Phenyl-6-(1H-pyrrol-3-yl)imidazo[1,2-a]pyridine-2-carboxamide

A solution of 120 mg of N-phenyl-6-(1-triisopropylsilyl-1H-pyrrol-3-yl)imidazo[1,2-a]pyridine-2-carboxamide in 5 mL of tetrahydrofuran is treated with 262 μL of a molar solution of tetrabutylammonium fluoride in tetrahydrofuran, and stirred for 10 minutes at room temperature. It is then diluted with 15 mL of dichloromethane and 20 mL of water. The organic phase is dried and concentrated to dryness under reduced pressure. The residue is taken up in 2 mL of dichloromethane, and the solid filtered off is washed twice with 1 mL of dichloromethane and then twice with 1 mL of diisopropyl ether, triturated twice with 2 mL of water, filtered off by suction and washed again with 2 mL of dichloromethane and 2 mL of diisopropyl ether and then dried to give 40 mg of N-phenyl-6-(1H-pyrrol-3-yl)imidazo[1,2-a]pyridine-2-carboxamide in the form of a white solid

EXAMPLE 11

6-(2-Methyl-1H-imidazol-4-yl)-N-phenylimidazo[1,2-a]pyridine-2-carboxamide 400 mg of 6-trimethylstannyl-N-phenylimidazo[1,2-a]pyridine-2-carboxamide (Intermediate 4), 229 mg of 2-methyl-4-iodo-1H-imidazole, 8 mL of tetrahydrofuran, 9.1 mg of bis(dibenzylideneacetone)palladium and 4.6 mg of tris(2-furyl)phosphine are placed in a microwave tube. The reaction mixture is heated for 50 minutes in a microwave machine set at 130° C. and then concentrated to dryness. The residue is taken up in 3.5 mL of N,N-dimethylformamide and a further 150 mg of 2-methyl-4-iodo-1H-imidazole, 10 mg of bis(dibenzylideneacetone)palladium and 5 mg of tris(2-furyl)phosphine are added, followed by heating again for 40 minutes in a microwave machine set at 120° C. The reaction mixture is filtered, the insoluble matter is rinsed with methanol and dichloromethane and the combined filtrates are concentrated under reduced pressure. The residue is chromatographed on a silica cartridge, eluting with dichloromethane and then with a 90/10 mixture of dichloromethane and methanol. The fractions containing the pure expected product are combined and evaporated to dryness under reduced pressure to give 28 mg of 6-(2-methyl-1H-imidazol-4-yl)-N-phenylimidazo[1,2-a]pyridine-2-carboxamide in the form of a beige-coloured solid.

EXAMPLE 12

6-(3-Furyl)-N-phenylimidazo[1,2-a]pyridine-2-carboxamide 200 mg of 6-bromo-N-phenylimidazo[1,2-a]pyridine-2-carboxamide (Intermediate 1), 10 mL of dioxane, 400 μL of 3-(triethoxysilyl)furan, 42 mg of palladium acetate, 42 mg of 1,4-diazabicyclo(2.2.2)octane (DABCO) and 1.5 mL of a molar solution of tetrabutylammonium fluoride in tetrahydrofuran are placed in a microwave tube. The reaction mixture is heated for 3 hours in a microwave machine set at 120° C., 200 μL of 3-(triethoxysilyl)furan, 20 mg of palladium acetate and 20 mg of DABCO are then added and the mixture is heated for a further 1.5 hours in a microwave machine set at 150° C. and then cooled and filtered. The filtrate is concentrated to dryness under reduced pressure and the residue is chromatographed on a silica cartridge, eluting with dichloromethane. The fractions containing the pure expected product are combined and evaporated to dryness under reduced pressure. The solid is dissolved while hot in a mixture of dichloromethane and methanol. The hot solution is filtered and treated with diisopropyl ether. The precipitate formed is filtered off by suction and dried to give 25 mg of 6-(3-furyl)-N-phenylimidazo[1,2-a]pyridine-2-carboxamide in the form of a yellow solid.

EXAMPLE 13

6-(1H-Imidazol-1-yl)-N-phenylimidazo[1,2-a]pyridine-2-carboxamide trifluoroacetate (1:1)

A mixture of 0.6 g of 6-iodo-N-phenylimidazo[1,2-a]pyridine-2-carboxamide (Intermediate 2), 20 mL of N,N-dimethylformamide, 1.08 g of caesium carbonate, 113 mg of imidazole, 60 mg of 1,10-phenanthroline and 31.5 mg of cuprous iodide is heated for 21 hours at 130° C. and, after addition of 70 mg of imidazole, is reacted for a further 3 hours at the same temperature and for 64 hours at room temperature. The reaction mixture is filtered, the insoluble matter is rinsed with dichloromethane and the combined filtrates are concentrated under reduced pressure. The residue is purified by preparative HPLC on a Waters Sunfire 30×100, 5 μm column, eluting with a gradient of acetonitrile containing from 0 to 60% water and 0.07% trifluoroacetic acid over 15 minutes and with a flow rate of 30 mL/min. The fractions containing the pure expected product are combined and evaporated to dryness under reduced pressure. The solid is beaten in 2 mL of methanol, filtered off and washed with 1 mL of methanol, and dried to give 110 mg of 6-(1H-imidazol-1-yl)-N-phenylimidazo[1,2-a]pyridine-2-carboxamide trifluoroacetate (1:1) in the form of a beige-coloured solid.

EXAMPLE 14

6-(Oxazol-5-yl)-N-phenylimidazo[1,2-a]pyridine-2-carboxamide

To a suspension of 200 mg of 6-formyl-N-phenylimidazo[1,2-a]pyridine-2-carboxamide (Intermediate 8) in 10 mL of methanol are added 104 mg of potassium carbonate and 147 mg of para-toluenesulfonylmethylisonitrile (TOSMIC). The reaction mixture is refluxed for 2 hours and then evaporated to dryness under reduced pressure, taken up in 300 mL of dichloromethane and washed with water. The organic phase is dried and concentrated to dryness on silica and then chromatographed on a silica cartridge, eluting with a gradient of from 0 to 20% of methanol in dichloromethane. The fractions containing the expected product are concentrated to dryness and the solid obtained is triturated with a small amount of dichloromethane, filtered off and dried to give 80 mg of 6-(oxazol-5-yl)-N-phenylimidazo[1,2-a]pyridine-2-carboxamide in the form of a white solid.

EXAMPLE 15

6-(2-Aminothiazol-4-yl)-N-phenylimidazo[1,2-a]pyridine-2-carboxamide

To a suspension of 60 mg of crude 6-(2-bromoacetyl)-N-phenylimidazo[1,2-a]pyridine-2-carboxamide in 10 mL of methanol are added 14 mg of thiourea. The reaction mixture is heated for 45 minutes at reflux and then concentrated to dryness under reduced pressure. The residue is chromatographed on a silica cartridge, eluting with a mixture of dichloromethane and methanol (gradient of from 100/0 to 90/10). The fractions containing the expected product are combined and evaporated to dryness under reduced pressure to give 20 mg of 6-(2-aminothiazol-4-yl)-N-phenylimidazo[1,2-a]pyridine-2-carboxamide in the form of a white solid.

EXAMPLE 16

6-(2-Methyl-1,3-dioxolan-2-yl)-N-phenylimidazo[1,2-a]pyridine-2-carboxamide

A mixture of 80 mg of 6-(1-ethoxyvinyl)-N-phenylimidazo[1,2-a]pyridine-2-carboxamide, 2.5 mL of toluene, 280 µL of ethylene glycol and 170 mg of para-toluenesulfonic acid is placed over molecular sieves. The mixture is refluxed for 2 hours and then cooled, filtered and diluted with 20 mL of dichloromethane and 20 mL of water, and neutralized with 2N sodium hydroxide solution. The aqueous phase is washed with dichloromethane and the combined organic phases are dried and concentrated to dryness. The residue is chromatographed on a silica cartridge, eluting with a gradient of dichloromethane and ethyl acetate of from 0/30 to 70/30 to give 17 mg of 6-(2-methyl-1,3-dioxolan-2-yl)-N-phenylimidazo[1,2-a]pyridine-2-carboxamide in the form of a white solid.

EXAMPLE 17

6-(4,5-Dihydro-1H-imidazol-2-yl)-N-phenylimidazo[1,2-a]pyridine-2-carboxamide hydrochlorides (1:1) and (1:2)

17.1 Ethyl 2-phenylcarbamoylimidazo[1,2-a]pyridine-6-carboximidate hydrochloride (1:1)

A suspension of 300 mg of N-phenyl-6-cyanoimidazo[1,2-a]pyridine-2-carboxamide (Intermediate 2) in 25 mL of ethanol containing 0.5 mL of DMF is cooled to 0° C. and then treated for 1 hour 40 minutes with hydrogen chloride gas. The reaction mixture is stirred at room temperature for 16 hours and then concentrated under reduced pressure to a small volume. The precipitate is filtered off by suction and washed with ethanol and ethyl ether to give 296 mg of ethyl 2-phenylcarbamoylimidazo[1,2-a]pyridine-6-carboximidate hydrochloride (1:1) in the form of a white solid, which is used without further purification for the rest of the synthesis.

17.2 6-(4,5-Dihydro-1H-imidazol-2-yl)-N-phenylimidazo[1,2-a]pyridine-2-carboxamide hydrochlorides (1:1) and (1:2)

A suspension of 296 mg of ethyl 2-phenylcarbamoylimidazo[1,2-a]pyridine-6-carboximidate hydrochloride (1:1) in 10 mL of ethanol is cooled to 0° C., followed by addition of 144 µL of ethylenediamine. The reaction mixture is refluxed for 16 hours and then stirred at room temperature for 60 hours. The precipitate is filtered off by suction and washed with ethanol and then recrystallized from methanol to give 64 mg of 6-(4,5-dihydro-1H-imidazol-2-yl)-N-phenylimidazo[1,2-a]pyridine-2-carboxamide hydrochloride (1:2) in the form of a white solid. The filtrate is concentrated to dryness and taken up in water. The insoluble matter is filtered off by suction, washed with methanol and then dried to give 99 mg of 6-(4,5-dihydro-1H-imidazol-2-yl)-N-phenylimidazo[1,2-a]pyridine-2-carboxamide hydrochloride (1:1) in the form of a white solid.

EXAMPLE 18

6-(6-Methoxypyrid-2-yl)-N-phenylimidazo[1,2-a]pyridine-2-carboxamide

To a solution of 624 mg of caesium carbonate, 90 mg of 2-bromo-6-methoxypyridine and 17.5 mg of [1,1'-bis(diphenylphosphino)ferrocene]dichloropalladium in 10 mL of dioxane and 4 mL of water are added 160 mg of 2-phenylcarbamoylimidazo[1,2-a]pyridine-6-boronic acid. The mixture is refluxed for one hour, and then cooled and concentrated to dryness under reduced pressure. The residue is taken up in 150 mL of dichloromethane and washed with 100 mL of water. The organic phase is dried over magnesium sulfate, filtered and concentrated to dryness under reduced pressure on silica and then chromatographed on a silica cartridge, eluting with a gradient of from 0 to 35% ethyl acetate in cyclohexane. The fractions containing the pure expected product are combined and concentrated to dryness under reduced pressure to give 36 mg of 6-(6-methoxypyrid-2-yl)-N-phenylimidazo[1,2-a]pyridine-2-carboxamide in the form of an off-white solid.

EXAMPLE 19

5-Methyl-N-phenyl-6-(pyrid-2-yl)imidazo[1,2-a]pyridine-2-carboxamide 19.1: Ethyl 6-iodo-5-methyl(pyrid-2-yl)imidazo[1,2-a]pyridine-2-carboxylate To a suspension of 2 g of 5-iodo-6-methylpyridine-2-amine in 15 mL of dimethoxyethane are added 1.3 mL of ethyl bromopyruvate. The reaction mixture is stirred at 20° C. for 16 hours and then concentrated to dryness, taken up in 15 mL of ethanol, refluxed for 2.5 hours and finally concentrated under reduced pressure. The residue is taken up in a mixture of dichloromethane and saturated sodium bicarbonate solution. The organic phase is dried over magnesium sulfate and concentrated to dryness under reduced pressure to give 2.77 g of ethyl 6-iodo-5-methyl(pyrid-2-yl)imidazo[1,2-a]pyridine-2-carboxylate in the form of a beige-coloured solid.

$^1$H NMR spectrum (DMSO-d6, δ in ppm): 1.33 (t, J=7.1 Hz, 3H), 2.84 (s, 3H), 4.33 (q, J=7.1 Hz, 2H), 7.34 (d, J=9.3 Hz, 1H), 7.66 (d, J=9.3 Hz, 1H), 8.48 (s, 1H).

Mass spectrum (LC-MS-DAD-ELSD): m/z 331 [M+H]+.

19.2: 6-Iodo-5-methyl-N-phenyl(pyrid-2-yl)imidazo[1,2-a]pyridine-2-carboxamide

To a solution of 852 μL of aniline in 104 mL of toluene cooled to 0° C. are added dropwise 6.2 mL of a 2M solution of trimethylaluminium in toluene, followed by addition, at 20° C., of 1.5 g of ethyl 6-iodo-5-methyl(pyrid-2-yl)imidazo[1,2-a]pyridine-2-carboxylate. The reaction mixture is stirred for 2 hours at 20° C. The resulting mixture is cooled to 4° C. and 120 mL of saturated ammonium chloride solution are then added. After concentrating under reduced pressure, the residue is taken up in ethyl acetate and the organic phase is washed with water, dried over magnesium sulfate, filtered through Celite and evaporated to dryness under reduced pressure. The residue is triturated in methanol, filtered off and dried to give 1.15 g of 6-iodo-5-methyl-N-phenyl(pyrid-2-yl)imidazo[1,2-a]pyridine-2-carboxamide in the form of a yellow solid.

$^1$H NMR spectrum (DMSO-d6, δ in ppm): 2.89 (s, 3H), 7.10 (tt, J=1.5 and 7.5 Hz, 1H), 7.33 (t, J=7.5 Hz, 2H), 7.39 (d, J=9.5 Hz, 1H), 7.70 (d, J=9.5 Hz, 1H), 7.90 (d, J=7.5 Hz, 2H), 8.49 (s, 1H), 10.3 (s, 1H).

Mass spectrum (LC-MS-DAD-ELSD): m/z 378 [M+H]$^+$.

19.3: 5-Methyl-N-phenyl-6-(pyrid-2-yl)imidazo[1,2-a]pyridine-2-carboxamide

This product is obtained in a manner similar to that for the product of Example 3, replacing the 6-iodo-N-phenylimidazo[1,2-a]pyridine-2-carboxamide with 6-iodo-5-methyl-N-phenyl(pyrid-2-yl)imidazo[1,2-a]pyridine-2-carboxamide.

EXAMPLE 20

6-(2-Amino-1H-imidazol-4-yl)-N-phenylimidazo[1,2-a]-pyridine-2-carboxamide trifluoroacetate (1:1)

To a solution of 135 mg of 6-(2-bromoacetyl)-N-phenylimidazo[1,2-a]pyridine-2-carboxamide (Intermediate 9) in 10 mL of N,N-dimethylformamide are added 190 mg of 1-tert-butyloxycarbonylguanidine. The reaction mixture is stirred for 16 hours at 20° C. and then concentrated to dryness at 60° C. under reduced pressure. The residue is taken up in 5 mL of dichloromethane and 3 mL of methanol and the solution is evaporated on silica and then chromatographed on a silica cartridge, eluting with a mixture of dichloromethane and methanol (gradient of from 100/0 to 90/10). The fractions containing the expected product are combined and evaporated to dryness under reduced pressure to give 50 mg of a mixture of 6-(2-tert-butyloxycarbonylaminothiazol-4-yl)-N-phenylimidazo[1,2-a]pyridine-2-carboxamide and 6-(2-amino-1-tert-butyloxycarbonylthiazol-4-yl)-N-phenylimidazo[1,2-a]pyridine-2-carboxamide in the form of a beige-coloured solid. This product is dissolved in 5 mL of dioxane and treated with 320 μL of a 4 N solution of hydrogen chloride in dioxane. The mixture is heated at 60° C. for 4 hours, followed by addition of 200 μL of a 4 N solution of hydrogen chloride in dioxane, and then concentrated to dryness under reduced pressure. The residue is purified by preparative LC/MS to give 18 mg of 6-(2-amino-1H-imidazol-4-yl)-N-phenylimidazo[1,2-a]pyridine-2-carboxamide trifluoroacetate (1:1) in the form of a beige-coloured solid.

EXAMPLE 21

6-(2-Aminothiazol-5-yl)-N-phenylimidazo[1,2-a]pyridine-2-carboxamide 21.1: 6-(2-Ethoxyvinyl)-N-phenylimidazo[1,2-a]pyridine-2-carboxamide This product is obtained under conditions similar to those described in the first step of preparation of Intermediate 9, replacing the tributyl(1-ethoxyvinyl)tin with tributyl(2-ethoxyvinyl)tin.

$^1$H NMR spectrum (DMSO-d6, δ in ppm): 1.33 (t, J=7.2 Hz, 3H), 4.06 (q, J=7.2 Hz, 2H), 5.26 (d, J=6.8 Hz, 1H), 6.52 (d, J=6.8 Hz, 1H), 7.08 (t, J=7.8 Hz, 1H), 7.34 (t, J=7.8 Hz, 2H), 7.54-7.66 (m, 2H), 7.88 (d, J=7.8 Hz, 2H), 8.51 (s, 1H), 8.75 (s, 1H), 10.16 (s, 1H).

21.2: 6-(2-Aminothiazol-5-yl)-N-phenylimidazo[1,2-a]pyridine-2-carboxamide

To a solution of 168 mg of 6-(2-ethoxyvinyl)-N-phenylimidazo[1,2-a]pyridine-2-carboxamide in 5.1 mL of tetrahydrofuran are added 1.4 mL of water followed by addition, after cooling to 0° C., of a solution of 97 mg of N-bromosuccinimide in 0.7 mL of tetrahydrofuran. The reaction mixture is stirred for 3 hours at room temperature. The 6-(1-bromo-2-oxoethyl)-N-phenylimidazo[1,2-a]pyridine-2-carboxamide formed is not isolated from the reaction mixture, which is treated with 42 mg of thiourea and stirred for a further 16 hours after allowing the temperature to return to 20° C. The solid formed is filtered off by suction, washed with water and then with methanol and dried to give 51 mg of 6-(2-aminothiazol-5-yl)-N-phenylimidazo[1,2-a]pyridine-2-carboxamide in the form of a white solid.

EXAMPLE 22

6-(6-Hydroxypyrid-2-yl)-N-phenylimidazo[1,2-a]pyridine-2-carboxamide 22.1: 6-(6-Benzyloxypyrid-2-yl)-N-phenylimidazo[1,2-a]pyridine-2-carboxamide To a solution of 250 mg of 2-benzyloxy-6-bromopyridine in 12 mL of dioxane are added a solution of 1.234 g of caesium carbonate in 3 mL of water, 34.6 mg of [1,1'-bis(diphenylphosphino)ferrocene]dichloropalladium and then 546 mg of N-phenyl-6-(4,4,5,5-tetramethyl-1,3,2-dioxaborolan-2-yl)imidazo[1,2-a]pyridine-2-carboxamide hydrobromide (1:1). The mixture is heated at 110° C. for 2 hours 45 minutes, and then cooled and filtered. The solid is washed with a small amount of methanol and then with dichloromethane and is then taken up in 250 mL of boiling methanol containing 5 mL of trifluoroacetic acid. The insoluble matter is filtered off and washed with methanol and then with dichloromethane and the filtrate is concentrated to dryness under reduced pressure. The residue is chromatographed on a silica cartridge, eluting with a gradient of from 0 to 5% of methanol in dichloromethane. The fractions containing the pure expected product are combined and concentrated to dryness under reduced pressure to give 0.3 g of 6-(6-benzyloxypyrid-2-yl)-N-phenylimidazo[1,2-a]pyridine-2-carboxamide in the form of a white solid.

$^1$H NMR spectrum (DMSO-d6, δ in ppm): 5.54 (s, 2H), 6.91 (d, J=8.3 Hz, 1H), 7.11 (broad t, J=7.7 Hz, 1H), 7.31-7.45 (m, 5H), 7.54 (m, 2H), 7.63 (d, J=7.8 Hz, 1H), 7.77 (d, J=9.7 Hz, 1H), 7.85-7.93 (m, 3H), 8.12 (dd, J=9.7, 2.0 Hz, 1H), 8.64 (s, 1H), 9.44 (broad s, 1H), 10.30 (broad s, 1H).

Mass spectrum (LC-MS-DAD-ELSD): m/z 421 [M+H]$^+$.

22.2: 6-(6-Hydroxypyrid-2-yl)-N-phenylimidazo[1,2-a]pyridine-2-carboxamide

A solution of 300 mg of 6-(6-benzyloxypyrid-2-yl)-N-phenylimidazo[1,2-a]pyridine-2-carboxamide in 3 mL of trifluoroacetic acid is stirred at 25° C. for 48 hours and then evaporated to dryness under reduced pressure at 45° C. The residue is triturated with ether, filtered off and dried, and then triturated again with 2 mL of saturated sodium bicarbonate solution, washed twice with 2 mL of water and twice with 2 mL of ethyl ether and dried under reduced pressure to give 168 mg of 6-(6-hydroxypyrid-2-yl)-N-phenylimidazo[1,2-a]pyridine-2-carboxamide in the form of a beige-coloured solid.

EXAMPLE 23

N-Phenyl-6-(1H-1,2,3-triazol-4-yl)imidazo[1,2-a]pyridine-2-carboxamide

23.1 6-Ethynyl-N-phenylimidazo[1,2-a]pyridine-2-carboxamide 0.2 g of 6-iodo-N-phenylimidazo[1,2-a]pyridine-2-carboxamide (Intermediate 2), 156 μL of trimethylsilylacetylene, 20 mg of dichlorobis(triphenylphosphine)palladium and 2 mL of piperidine are placed in a 20 mL microwave tube. The mixture is heated for 15 minutes in a microwave machine set at 130° C. After cooling, the mixture is poured into 50 mL of saturated aqueous ammonium chloride solution. The resulting mixture is extracted twice with 70 mL of ethyl ether. The combined organic phases are separated out by settling, dried and concentrated to dryness under reduced pressure. The residue is taken up in 4 mL of a 1M solution of tetrabutylammonium fluoride in THF and stirred for 16 hours at 25° C. After evaporating the reaction medium to dryness, the residue is chromatographed on silica, eluting with a mixture of cyclohexane and ethyl acetate (gradient from 0 to 35%) to give 30 mg of 6-ethynyl-N-phenylimidazo[1,2-a]pyridine-2-carboxamide in the form of a beige-coloured solid.

$^1$H NMR spectrum (DMSO-d6, δ in ppm): 4.37 (s, 1H), 7.09 (t, J=8.0 Hz, 1H), 7.34 (broad t, J=8.0 Hz, 2H), 7.39 (broad d, J=9.5 Hz, 1H), 7.67 (d, J=9.5 Hz, 1H), 7.89 (broad d, J=8.0 Hz, 2H), 8.48 (s, 1H), 8.92 (broad s, 1H), 10.3 (s, 1H).

Mass spectrum (EI): m/z 261 [M]$^+$ (base peak), m/z=221 [M−NHPh]$^+$.

23.2: N-Phenyl-6-(1H-1,2,3-triazol-4-yl)imidazo[1,2-a]pyridine-2-carboxamide 123 mg of 6-ethynyl-N-phenylimidazo[1,2-a]pyridine-2-carboxamide, 46 mg of sodium azide, 38 mg of ammonium chloride and 5 mL of N,N-dimethylformamide are placed in a microwave tube. The reaction mixture is heated for 20 minutes in a microwave machine set at 170° C. and then for a further 30 minutes under the same conditions, followed by addition of 46 mg of sodium azide and 38 mg of ammonium chloride, and finally concentrated at 50° C. under reduced pressure. The residue is taken up in 20 mL of ethyl acetate and 20 mL of water. The aqueous phase is extracted twice with 20 mL of ethyl acetate and the combined organic phases are washed with 30 mL of saturated brine and then dried over magnesium sulfate and concentrated to dryness under reduced pressure. The residue is chromatographed on a silica cartridge, eluting with a gradient of dichloromethane and methanol (from 100/0 to 90/10). The fractions containing the expected product are combined and concentrated to dryness under reduced pressure to give 36 mg of N-phenyl-6-(1H-1,2,3-triazol-4-yl)imidazo[1,2-a]pyridine-2-carboxamide in the form of an off-white solid.

EXAMPLE 24

N-(3,5-Difluorophenyl)-6-(furan-3-yl)imidazo[1,2-a]pyridine-2-carboxamide 83 mg of potassium carbonate and 4 mL of 1,2-dimethoxyethane are placed in a microwave tube, followed, after degassing with argon, by 120 mg of N-(3,5-difluorophenyl)-6-iodoimidazo[1,2-a]pyridine-2-carboxamide (Intermediate 10), 40 mg of 3-furanboronic acid and 21 mg of dichlorobis(triphenylphosphine)palladium(II). The reaction mixture is heated for 20 minutes in a microwave machine set at 120° C. and then poured into a mixture of 15 mL of ethyl acetate and 15 mL of water. The aqueous phase is extracted twice with 15 mL of ethyl acetate and the combined organic phases are washed with 15 mL of saturated brine and then dried over magnesium sulfate and concentrated to dryness under reduced pressure. The residue is triturated twice with 10 mL of a methanol/ethyl ether mixture (1/1) and then washed with isopropanol and pentane and dried to give 22 mg of N-(3,5-difluorophenyl)-6-(furan-3-yl)imidazo[1,2-a]pyridine-2-carboxamide in the form of a white solid.

EXAMPLE 25

N-(3-Fluorophenyl)-6-(furan-3-yl)imidazo[1,2-a]pyridine-2-carboxamide

To a suspension of 65 mg of 6-(furan-3-yl)imidazo[1,2-a]pyridine-2-carboxylic acid (Intermediate 19) and 104 mg of 1-(3-dimethylaminopropyl)-3-ethylcarbodiimide hydrochloride in 2 mL of anhydrous pyridine, placed under argon, are added 68 mg of 3-fluoroaniline. The reaction mixture is stirred for 16 hours at 80° C. and then concentrated to dryness under reduced pressure. The residue is taken up in dichloromethane and washed with water. The organic phase is dried over magnesium sulfate and concentrated to dryness under reduced pressure to give 46 mg of N-(3-fluorophenyl)-6-(furan-3-yl)imidazo[1,2-a]pyridine-2-carboxamide in the form of a white solid.

The intermediates described below are useful for preparing the compounds of the present invention.

Intermediate 1: 6-Bromo-N-phenylimidazo[1,2-a]pyridine-2-carboxamide

To a solution of 3 g of aniline in 366 mL of toluene cooled to 0° C. are added dropwise 22.5 mL of a 2M solution of trimethylaluminium in toluene, followed by addition, at 20° C., of 5.6 g of ethyl 6-bromoimidazo[1,2-a]pyridine-2-carboxylate. The reaction mixture is stirred for 2 hours at room temperature. The resulting mixture is cooled to 4° C. and 150 mL of saturated ammonium chloride solution are then added.

The reaction mixture is concentrated to dryness and is then taken up in 400 mL of water and 400 mL of dichloromethane. The organic phase is dried over magnesium sulfate, filtered through Celite and evaporated to dryness under reduced pressure to give 4.6 g of 6-bromo-N-phenylimidazo[1,2-a]pyridine-2-carboxamide in the form of an off-white powder.

$^1$H NMR spectrum (DMSO-d6, δ in ppm): 7.09 (t, J=7.5 Hz, 1H), 7.34 (t, J=7.5 Hz, 2H), 7.51 (d, J=9.5 Hz, 1H), 7.57 (dd, J=1.5 and 9.5 Hz, 1H), 7.88 (d, J=8.0 Hz, 2H), 8.42 (s, 1H), 9.02 (broad s, 1H), 10.25 (s, 1H).

Mass spectrum (EI): m/z=363 [M]$^+$, m/z=271 [M−C$_6$H$_6$N]$^+$, m/z=144 [m/z=271-I]$^+$.

Intermediate 2: 6-Iodo-N-phenylimidazo[1,2-a]pyridine-2-carboxamide

By working in the same manner as for the preparation of Intermediate 1, replacing the ethyl 6-bromoimidazo[1,2-a]pyridine-2-carboxylate with ethyl 6-iodoimidazo[1,2-a]pyridine-2-carboxylate, 6-iodo-N-phenylimidazo[1,2-a]pyridine-2-carboxamide is obtained in the form of a beige-coloured solid.

$^1$H NMR spectrum (DMSO-d6, δ in ppm): 7.09 (t, J=7.5 Hz, 1H), 7.34 (t, J=7.5 Hz, 2H), 7.51 (d, J=9.5 Hz, 1H), 7.57 (dd, J=1.5 and 9.5 Hz, 1H), 7.88 (d, J=8.0 Hz, 2H), 8.42 (s, 1H), 9.02 (broad s, 1H), 10.25 (s, 1H).

Mass spectrum (EI): m/z=363 [M]$^+$, m/z=271 [M−C$_6$H$_6$N]$^+$, m/z=144 [m/z=271-I]$^+$.

Intermediate 3: N-Phenyl-6-cyanoimidazo[1,2-a]pyridine-2-carboxamide

By working in the same manner as for the preparation of Intermediate 1, replacing the ethyl 6-bromoimidazo[1,2-a]pyridine-2-carboxylate with ethyl 6-cyanoimidazo[1,2-a]pyridine-2-carboxylate (J. Med. Chem. (1998), 41(22), 4317), N-phenyl-6-cyanoimidazo[1,2-a]pyridine-2-carboxamide is obtained in the form of a yellow solid $^1$H NMR spectrum (DMSO-d6, δ in ppm): 7.11 (t, J=7.5 Hz, 1H), 7.35 (t, J=7.5 Hz, 2H), 7.65 (dd, J=2.0 and 9.5 Hz, 1H), 7.81 (d, J=9.5 Hz, 1H), 7.89 (d, J=8.0 Hz, 2H), 8.58 (s, 1H), 9.41 (broad s, 1H), 10.4 (broad s, 1H)

IR spectrum (KBr): 3364; 2234; 1671; 1599; 1560; 1527; 1504; 1433 and 748 cm$^{-1}$ Mass spectrum (EI): m/z=262 [M]$^+$ (base peak), m/z=170 [M−C$_6$H$_6$N]$^+$, m/z=143 [m/z=170-HCN]$^+$

Intermediate 4: 6-Trimethylstannyl-N-phenylimidazo[1,2-a]pyridine-2-carboxamide To a suspension of 160 mg of 6-bromo-N-phenylimidazo[1,2-a]pyridine-2-carboxamide in 10 mL of tolene are added 260 μL of hexamethyldistannane and 30 mg of tetrakis-(triphenylphosphine)palladium(0). The reaction mixture is heated for 2 hours at reflux and then stirred for 16 hours at room temperature and filtered through a pad of Celite. The filtrate is concentrated under reduced pressure and the residue is chromatographed on a silica cartridge, eluting with dichloromethane. The fractions containing the expected product are combined and evaporated to dryness under reduced pressure to give 163 mg of 6-trimethylstannyl-N-phenylimidazo[1,2-a]pyridine-2-carboxamide in the form of a yellow solid.

$^1$H NMR spectrum (DMSO-d6, δ in ppm): 0.85 (m, 9H), 7.09 (t, J=7.5 Hz, 1H), 7.33 (t, J=7.5 Hz, 2H), 7.40 (broad d, J=9.5 Hz, 1H), 7.61 (broad d, J=9.5 Hz, 1H), 7.89 (d, J=7.5 Hz, 2H), 8.43 (s, 1H), 8.53 (m, 1H), 10.2 (s, 1H).

Mass spectrum (LC-MS-DAD-ELSD): m/z 402, [M+H]$^+$

Intermediate 5: N-Phenyl-6-(4,4,5,5-tetramethyl-1,3,2-dioxaborolan-2-yl)imidaz-[1,2-a]pyridine-2-carboxamide and the hydrobromide (1:1) thereof To a solution of 1 g of 3-bromo-2-oxo-N-phenylpropionamide in 50 mL of 1,2-dimethoxyethane are added 1.09 g of 2-amino-5-(4,4,5,5-tetramethyl-1,3,2-dioxaborolan-2-yl)pyridine. The reaction mixture is stirred for 40 hours at room temperature and then concentrated to dryness under reduced pressure. The residue is taken up in 30 mL of ethanol and refluxed for 90 minutes. After concentrating to dryness under reduced pressure, the solid is triturated in a small amount of ethanol, filtered off and washed with ethanol and then with ethyl ether to give 0.6 g of N-phenyl-6-(4,4,5,5-tetramethyl-1,3,2-dioxaborolan-2-yl)imidazo[1,2-a]pyridine-2-carboxamide hydrobromide (1:1) in the form of a white solid.

This hydrobromide is taken up in 200 mL of ethyl acetate and washed with saturated sodium bicarbonate solution. The organic phase is dried and concentrated to dryness under reduced pressure to give 0.53 g of N-phenyl-6-(4,4,5,5-tetramethyl-1,3,2-dioxaborolan-2-yl)imidazo[1,2-a]pyridine-2-carboxamide in the form of a white solid.

$^1$H NMR spectrum (DMSO-d6, δ in ppm): 1.33 (s, 12H), 7.10 (t, J=7.5 Hz, 1H), 7.34 (t, J=7.5 Hz, 2H), 7.46 (dd, J=1.5 and 9.5 Hz, 1H), 7.63 (d, J=9.5 Hz, 1H), 7.89 (d, J=7.5 Hz, 2H), 8.58 (s, 1H), 8.96 (broad s, 1H), 10.25 (s, 1H).

Mass spectrum (EI): m/z 363 [M]$^+$; m/z 271=[M−NHPh]$^+$; m/z 171=[271-C6H12O]$^−$.

Intermediate 6: 2-Phenylcarbamoylimidazo[1,2-a]pyridine-6-boronic acid hydrochloride (1:1)

1°) To a solution of 0.8 g of 3-bromo-2-oxo-N-phenylpropionamide in 30 mL of 1,2-dimethoxyethane is added 0.87 g of 2-amino-5-(4,4,5,5-tetramethyl-1,3,2-dioxaborolan-2-yl)pyridine. The reaction mixture is stirred for 16 hours at room temperature and then concentrated to dryness under reduced pressure. The residue is taken up in 15 mL of ethanol and refluxed for 2 hours. After concentrating to dryness under reduced pressure, the residue is crystallized from ethanol, filtered off by suction and washed with ethanol and then with ethyl ether to give 0.75 g of N-phenyl-6-(4,4,5,5-tetramethyl-1,3,2-dioxaborolan-2-yl)imidazo[1,2-a]pyridine-2-carboxamide hydrobromide (1:1) in the form of a white solid.

$^1$H NMR spectrum (DMSO-d6, δ in ppm): 1.34 (s, 12H), 7.11 (t, J=7.8 Hz, 1H), 7.35 (t, J=7.8 Hz, 2H), 7.54 (broad d, J=9.3 Hz, 1H), 7.66 (d, J=9.3 Hz, 1H), 7.87 (d, J=7.8 Hz, 2H), 8.63 (s, 1H), 9.02 (s, 1H), 10.37 (broad s, 1H).

Mass spectrum (EI): m/z 363 [M]$^+$.

2°) A solution of 0.19 g of N-phenyl-6-(4,4,5,5-tetramethyl-1,3,2-dioxaborolan-2-yl)imidazo[1,2-a]pyridine-2-carboxamide hydrobromide (1:1) in 9 mL of acetonitrile is treated with 0.5 mL of hydrochloric acid and 1 g of polymer-supported benzeneboronic acid (Alfa-Aesar L19459, ~3 mmol/g). The reaction mixture is stirred for 16 hours at 25° C. and then refluxed for 1 hour. The resin is filtered off, washed with acetonitrile and then with methanol and the combined filtrates are evaporated to dryness under reduced pressure to give 160 mg of 2-phenylcarbamoylimidazo[1,2-a]pyridine-6-boronic acid hydrochloride (1:1) in the form of an orange-coloured solid.

$^1$H NMR spectrum (DMSO-d6, δ in ppm): 7.14 (t, J=7.8 Hz, 1H), 7.38 (t, J=7.8 Hz, 2H), 7.72 (broad m, 1H), 7.85 (d, J=7.8 Hz, 2H), 7.93 (broad m, 1H), 7.94-8.63 (very broad m, 2H), 8.81 (broad m, 1H), 9.04 (broad m, 1H), 10.52 (broad m, 1H).

Intermediate 7: N-Phenyl-6-vinylimidazo[1,2-a]pyridine-2-carboxamide

A mixture of 0.73 g of 6-iodo-N-phenylimidazo[1,2-a]pyridine-2-carboxamide, 209 mg of tetrakis(triphenylphosphine)palladium(0), 587 µL of tributylvinyltin and 17 mL of DMF is heated for 10 minutes at 130° C. in a microwave machine and then concentrated to dryness. The residue is taken up in 100 mL of water and extracted with twice 70 mL of ethyl acetate. The combined organic phases are washed with saturated sodium chloride solution, dried over magnesium sulfate and evaporated to dryness under reduced pressure. The solid is triturated in ethyl acetate, filtered off by suction, washed with ethyl acetate and then with isopropyl ether, and taken up in a mixture of methanol and dichloromethane. The insoluble matter is filtered off and washed with methanol. The filtrate is concentrated to dryness under reduced pressure to give 0.29 g of N-phenyl-6-vinylimidazo[1,2-a]pyridine-2-carboxamide in the form of a white solid.

$^1$H NMR spectrum (DMSO-d6, δ in ppm): 5.39 (d, J=11.0 Hz, 1H), 5.92 (d, J=17.5 Hz, 1H), 6.77 (dd, J=11.0 and 17.5 Hz, 1H), 7.09 (broad t, J=7.5 Hz, 1H), 7.34 (broad t, J=7.5 Hz, 2H), 7.64 (d, J=9.5 Hz, 1H), 7.70 (dd, J=2.0 and 9.5 Hz, 1H), 7.89 (broad d, J=8.0 Hz, 2H), 8.47 (s, 1H), 8.66 (broad s, 1H), 10.2 (s, 1H).

Mass spectrum (EI): m/z 263 [M$^+$]

Intermediate 8: 6-Formyl-N-phenylimidazo[1,2-a]pyridine-2-carboxamide

A suspension of 150 mg of N-phenyl-6-vinylimidazo[1,2-a]pyridine-2-carboxamide, 232 µL of osmium tetroxide and 167.5 mg of sodium periodate in a mixture of 6 mL of THF, 3 mL of t-butanol and 3 mL of water is stirred for 20 hours at 20° C. and then for a further 48 hours while adding in four portions 100 µL of osmium tetroxide and 80 mg of sodium periodate. The reaction mixture is poured into 50 mL of water and the resulting mixture is extracted twice with 50 mL of ethyl acetate. The combined organic phases are washed with saturated aqueous sodium chloride solution, separated by settling, dried and concentrated to dryness under reduced pressure. The residue is chromatographed on silica, eluting with a mixture of cyclohexane and ethyl acetate (gradient from 0 to 50%) to give 100 mg of 6-formyl-N-phenylimidazo[1,2-a]pyridine-2-carboxamide in the form of a white solid $^1$H NMR spectrum (DMSO-d6, δ in ppm): 7.11 (t, J=8.0 Hz, 1H), 7.36 (broad t, J=8.0 Hz, 2H), 7.71 (dd, J=1.5 and 9.5 Hz, 1H), 7.77 (broad d, J=9.5 Hz, 1H), 7.90 (broad d, J=8.0 Hz, 2H), 8.73 (s, 1H), 9.39 (broad s, 1H), 10.0 (s, 1H), 10.35 (broad s, 1H).

Mass spectrum (LC/MS): m/z 266, [M+H$^+$]

Intermediate 9: 6-(2-Bromoacetyl)-N-phenylimidazo[1,2-a]pyridine-2-carboxamide

9.1: 6-(1-Ethoxyvinyl)-N-phenylimidazo[1,2-a]pyridine-2-carboxamide

To a suspension of 1 g of 6-iodo-N-phenylimidazo[1,2-a]pyridine-2-carboxamide in 50 mL of toluene are added 159 mg of tetrakis(triphenylphosphine)palladium and 1.09 g of tributyl(1-ethoxyvinyl)tin. The reaction mixture is heated for 9 hours at 150° C. and then for 16 hours at 130° C., and concentrated to dryness. The residue is taken up in dichloromethane and washed with aqueous 10% potassium fluoride solution. The organic phase is dried and concentrated to dryness and the residue is chromatographed on a silica cartridge, eluting with a mixture of cyclohexane and ethyl acetate. The fractions containing the expected product are combined and evaporated to dryness under reduced pressure to give 0.52 g of 6-(1-ethoxyvinyl)-N-phenylimidazo[1,2-a]pyridine-2-carboxamide in the form of a beige-coloured solid.

$^1$H NMR spectrum (DMSO-d6, δ in ppm): 1.40 (t, J=7.0 Hz, 3H), 3.97 (q, J=7.0 Hz, 2H), 4.46 (d, J=3.0 Hz, 1H), 4.90 (d, J=3.0 Hz, 1H), 7.09 (t, J=8.0 Hz, 1H), 7.34 (broad t, J=8.0 Hz, 2H), 7.61 (d, J=9.5 Hz, 1H), 7.66 (dd, J=2.0 and 9.5 Hz, 1H), 7.89 (broad d, J=8.0 Hz, 2H), 8.57 (s, 1H), 8.83 (broad s, 1H), 10.2 (s, 1H).

9.2: 6-(2-Bromoacetyl)-N-phenylimidazo[1,2-a]pyridine-2-carboxamide

To a solution of 123 mg of 6-(1-ethoxyvinyl)-N-phenylimidazo[1,2-a]pyridine-2-carboxamide in 4 mL of tetrahydrofuran are added 1 mL of water and then, after cooling to 0° C., 71 mg of N-bromosuccinimide. The reaction mixture is stirred for 2.5 hours at room temperature and then diluted with 80 mL of dichloromethane. The organic phase is washed with water and then dried and concentrated to dryness under reduced pressure to give 60 mg of crude 6-(2-bromoacetyl)-N-phenylimidazo[1,2-a]pyridine-2-carboxamide in the form of a white solid (containing small amounts of 6-acetyl derivative and dibromo derivative) that is used without further purification.

$^1$H NMR spectrum (DMSO-d6, δ in ppm): 4.92 (s, 2H), 7.11 (t, J=7.5 Hz, 1H), 7.36 (t, J=7.5 Hz, 2H), 7.75 (d, J=9.5 Hz, 1H), 7.82 (dd, J=1.5 and 9.5 Hz, 1H), 7.90 (d, J=7.5 Hz, 2H), 8.61 (s, 1H), 9.57 (broad s, 1H), 10.35 (s, 1H).

Mass spectrum (LC-MS-DAD-ELSD): m/z 358 [M+H]$^+$, m/z 356 [M−H]$^-$.

Intermediate 10: N-(3,5-difluorophenyl)-6-iodoimidazo[1,2-a]pyridine-2-carboxamide To a solution of 980 mg of aniline in 100 mL of toluene cooled to 0° C. are added dropwise 5 mL of a 2M solution of trimethylaluminium in toluene and then, at 20° C., 1.5 g of ethyl 6-iodoimidazo[1,2-a]pyridine-2-carboxylate. The reaction mixture is stirred for 2 hours at 20° C. The resulting mixture is cooled to 4° C. and 100 mL of saturated ammonium chloride solution are then added. After concentrating under reduced pressure, the residue is taken up in ethyl acetate and the organic phase is washed with water, dried over magnesium sulfate, filtered through Celite and evaporated to dryness under reduced pressure. The residue is triturated in ethyl ether, filtered off and dried to give 258 mg of N-(3,5-difluorophenyl)-6-iodoimidazo[1,2-a]pyridine-2-carboxamide in the form of a yellow solid.

$^1$H NMR spectrum (DMSO-d1, δ in ppm): 6.92 (tt, J=2.0 and 9.0 Hz, 1H), 7.51 (d, J=9.5 Hz, 1H), 7.59 (dd, J=1.5 and 9.5 Hz, 1H), 7.72 (m, 2H), 8.47 (s, 1H), 9.02 (broad s, 1H), 10.75 (s, 1H).

Mass spectrum (LC-MS-DAD-ELSD): m/z 398 [M+H]$^-$; m/z 400 [M+H]$^+$.

Intermediate 11: 6-(6-{[(1,1-Dimethylethoxy)carbonyl]amino}pyrid-2-yl)imidazo-[1,2-a]pyridine-2-carboxylic acid

11.1: Ethyl 6-(6-aminopyrid-2-yl)imidazo[1,2-a]pyridine-2-carboxylate 350 mg of 2-amino-6-bromopyridine, 750 mg of 2-ethoxycarbonylimidazo[1,2-a]pyridine-6-boronic acid and 57 mg of

[1,1'-bis(diphenylphosphino)ferrocene]dichloropalladium are degassed under vacuum and then suspended, under argon, in 20 mL of degassed dioxane. After addition of 2 mL of aqueous 2N sodium carbonate solution, the mixture is degassed under vacuum, placed under argon and heated for 5 hours at 90° C., and then cooled, diluted and stirred in a mixture of 50 mL of saturated sodium bicarbonate solution and 50 mL of dichloromethane. The organic phase is dried over sodium sulfate, filtered and concentrated to dryness under reduced pressure. The residue is chromatographed on silica, eluting with a mixture of ethyl acetate and hexane. The fractions containing the expected product are combined and concentrated to dryness under reduced pressure to give 446 mg of ethyl 6-(6-aminopyrid-2-yl)imidazo[1,2-a]pyridine-2-carboxylate.

$^1$H NMR spectrum (DMSO-d6, δ in ppm): 9.13 (dd, J=1.0, 1.6 1H), 8.61 (d, J=0.7, 1H), 7.94 (dd, J=1.8, 9.6, 1H), 7.65 (d, J=9.6, 1H), 7.50 (t, J=8.1, 1H), 7.07 (d, J=7.0, 1H), 6.48 (dd, J=0.3, 8.1, 1H), 6.08 (broad s, 2H), 4.33 (q, J=7.1, 2H), 1.33 (t, J=7.1, 3H).

Mass spectrum (APCI): m/z=283 [M+H]$^+$.

11.2: Ethyl 6-(6-{[(1,1-dimethylethoxy)carbonyl]amino}pyrid-2-yl)imidazo[1,2-a]pyridine-2-carboxylate and ethyl 6-(6-{bis[(1,1-dimethylethoxy)carbonyl]amino}pyrid-2-yl)-imidazo[1,2-a]pyridine-2-carboxylate To a suspension of 700 mg of ethyl 6-(6-aminopyrid-2-yl)imidazo[1,2-a]pyridine-2-carboxylate and 25 mg of 4-dimethylaminopyridine in 5 mL of acetonitrile are added 1.14 mL of di-tert-butyl dicarbonate. The mixture is stirred for 16 hours at 25° C. and then concentrated. The residue is chromatographed on silica, eluting with gradient of ethyl acetate and hexane (from 50/50 to 100/0) to give 370 mg of ethyl 6-(6-{bis[(1,1-dimethylethoxy)carbonyl]amino}pyrid-2-yl)imidazo[1,2-a]pyridine-2-carboxylate $^1$H NMR spectrum (DMSO-d6, δ in ppm): 9.23 (s, 1H), 8.65 (s, 1H), 8.06-7.98 (m, 2H), 7.95 (d, J=7.7, 1H), 7.76 (d, J=9.6, 1H), 7.43 (d, J=7.8, 1H), 4.33 (q, J=7.0, 2H), 1.43 (s, 18H), 1.34 (t, J=7.1, 3H).

Mass spectrum (APCI): m/z=483 [M+H]$^+$,
and 163 mg of ethyl 6-(6-{[(1,1-dimethylethoxy)carbonyl]amino}pyrid-2-yl)imidazo[1,2-a]pyridine-2-carboxylate.

$^1$H NMR spectrum (DMSO-d6, δ in ppm): 9.28 (s, 1H), 8.50 (s, 1H), 8.04-8.00 (m, 2H), 7.95 (d, J=7.8, 1H), 7.70 (d, J=9.6, 1H), 7.38 (d, J=7.9, 1H), 4.31 (q, J=7.0, 2H), 1.39 (s, 9H), 1.33 (t, J=7.1, 3H).

Mass spectrum (APCI): m/z=383 [M+H]$^+$.

11.3: 6-(6-{[(1,1-Dimethylethoxy)carbonyl]amino}pyrid-2-yl)imidazo[1,2-a]pyridine-2-carboxylic acid 0.9 mL of aqueous 2 M lithium hydroxide solution is added to a solution of 292 mg of ethyl 6-(6-{bis[(1,1-dimethylethoxy)carbonyl]amino}pyrid-2-yl)imidazo[1,2-a]pyridine-2-carboxylate in 4.73 mL of a 50/1 mixture of tetrahydrofuran and methanol. The reaction mixture is stirred for 7 hours at 25° C. and then treated dropwise at 0° C. with 2 N hydrochloric acid HCl until a pH of 3 is obtained. The precipitate formed after 20 minutes is filtered off by suction and washed with water (20 mL) and diethyl ether (20 ml) and then dried under reduced pressure to give 195 mg of 6-(6-{[(1,1-dimethylethoxy)carbonyl]amino}pyrid-2-yl)imidazo[1,2-a]pyridine-2-carboxylic acid in the form of a beige-coloured solid.

$^1$H NMR spectrum (DMSO-d6, δ in ppm): 13.5-12.0 (br, 1H), 9.80 (s, 1H), 9.24 (s, 1H), 8.51 (s, 1H), 8.03 (dd, J=1.5, 9.6 1H), 7.88 (app, t, J=8.0, 7.8, 1H), 7.77 (d, J=8.2, 1H), 7.73 (d, J=9.6, 1H), 7.62 (d, J=7.5, 1H), 1.50 (s, 9H)

Intermediate 12: 6-(Pyrid-2-yl)imidazo[1,2-a]pyridine-2-carboxylic acid

12.1: Ethyl (6-pyrid-2-yl)imidazo[1,2-a]pyridine-2-carboxylate

A mixture of 3.18 g of caesium carbonate, 25 mL of dioxane, 9.3 mL of water, 500 mg of 2-iodopyridine, 89 mg of [1,1'-bis(diphenylphosphino)ferrocene]dichloropalladium and 848 mg of ethyl 6-(4,4,5,5-tetramethyl-1,3,2-dioxaborolan-2-yl)imidazo[1,2-a]pyridine-2-carboxylate hydrobromide (1:1) is heated for 2 hours at 110° C., and then partially concentrated, diluted with dichloromethane and filtered. The organic phase is washed with water and dried over magnesium sulfate, filtered and concentrated to dryness under reduced pressure. The residue is chromatographed on a silica cartridge, eluting with a mixture of dichloromethane and cyclohexane (80/20). The fractions containing the expected product are combined and concentrated to dryness under reduced pressure to give 317 mg of ethyl 6-(pyrid-2-yl)imidazo[1,2-a]pyridine-2-carboxylate in the form of a brown oil.

$^1$H NMR spectrum (DMSO-d6, δ in ppm): 1.34 (t, J=7.0 Hz, 3H), 4.33 (q, J=7.0 Hz, 2H), 7.42 (ddd, J=7.5, 5.5, 2.0 Hz, 1H), 7.73 (d, J=9.3 Hz, 1H), 7.85-8.02 (m, 2H), 8.07 (dd, J=9.3, 2.0 Hz, 1H), 8.64 (s, 1H), 8.70 (broad d, J=5.5 Hz, 1H), 9.36 (broad s, 1H).

Mass spectrum (LC-MS-DAD-ELSD): m/z 268 [M+H]$^+$.

12.2: 6-(Pyrid-2-yl)imidazo[1,2-a]pyridine-2-carboxylic acid 317 mg of ethyl 6-(pyrid-2-yl)imidazo[1,2-a]pyridine-2-carboxylate are saponified under conditions similar to those described for the preparation of Intermediate 11 (step 11.3) to give 280 mg of 6-(pyrid-2-yl)imidazo[1,2-a]pyridine-2-carboxylic acid in the form of a pasty pink solid.

$^1$H NMR spectrum (DMSO-d6, δ in ppm): 7.47 (m, 1H), 7.83 (d, J=9.8 Hz, 1H), 7.99 (dt, J=8.5, 2.0 Hz, 1H), 8.06 (d, J=8.5 Hz, 1H), 8.31 (broad d, J=9.8 Hz, 1H), 8.73 (m, 2H), 9.52 (broad s, 1H).

Mass spectrum (LC-MS-DAD-ELSD): m/z 240 [M+H]$^+$.

Intermediate 13: 6-(1-Triphenylmethyl-1H-imidazol-4-yl)imidazo[1,2-a]pyridine-2-carboxylic acid

13.1: Ethyl 6-(1-triphenylmethyl-1H-imidazol-4-yl)imidazo[1,2-a]pyridine-2-carboxylate 873 mg of 4-iodo-1-triphenylmethylimidazole, 750 mg of 2-ethoxycarbonylimidazo[1,2-a]pyridine-6-boronic acid, 23 mg of palladium acetate and 70 mg of (2-biphenyl)dicyclohexyl-phosphine are degassed under vacuum and then suspended, under argon, in a degassed mixture of 15 mL of toluene, 5 mL of water and 5 mL of N-methylpyrrolidone. After addition of 950 mg of potassium phosphate, the mixture is degassed under vacuum and then placed under argon and heated for 15 minutes at 100° C. by microwave, then cooled, diluted and stirred in a mixture of 50 mL of saturated sodium bicarbonate solution and 50 mL of dichloromethane. The organic phase is dried over sodium sulfate, filtered and concentrated to dryness under reduced pressure. The residue is chromatographed on silica, eluting with a mixture of ethyl acetate and hexane. The fractions containing the expected product are combined and concentrated to dryness under reduced pressure to give 508 mg of ethyl 6-(1-triphenylmethyl-1H-imidazol-4-yl)imidazo[1,2-a]pyridine-2-carboxylate.

$^1$H NMR spectrum (DMSO-d6, δ in ppm): 8.97 (s, 1H), 8.54 (s, 1H), 7.76-7.72 (m, 1H), 7.56-7.52 (m, 3H), 7.47-7.37 (m, 9H), 7.20-7.17 (m, 6H), 4.31-4.27 (m, 2H), 1.34-1.20 (m, 3H).

Mass spectrum (APCI): m/z=499 [M+H]$^+$.

13.2: 6-(1-Triphenylmethyl-1H-imidazol-4-yl)imidazo[1,2-a]pyridine-2-carboxylic acid 500 mg of ethyl 6-(1-triphenylmethyl-1H-imidazol-4-yl)imidazo[1,2-a]pyridine-2-carboxylate are saponified under conditions similar to those described for the preparation of Intermediate 11 (step 11.3) to give 346 mg of 6-(1-triphenylmethyl-1H-imidazol-4-yl)imidazo[1,2-a]pyridine-2-carboxylic acid.

$^1$H NMR spectrum (DMSO-d6, δ in ppm): 9.01 (s, 1H), 8.51 (s, 1H), 7.83 (d, J=9.5, 1H), 7.59-7.56 (m, 3H), 7.47-7.37 (m, 9H), 7.20-7.17 (m, 6H). No exchangeable proton is observed.

Mass spectrum (APCI): m/z=471 [M+H]$^+$.

Intermediate 14: 6-(2-{[(1,1-Dimethylethoxy)carbonyl]amino}thiazol-4-yl)imidazo[1,2-a]pyridine-2-carboxylic acid

14.1: Ethyl 6-(2-{[(1,1-dimethylethoxy)carbonyl]amino}thiazol-4-yl)imidazo[1,2-a]pyridine-2-carboxylate 465 mg of tert-butyl 4-iodothiazol-2-ylcarbamate, 434 mg of 2-ethoxycarbonyl-imidazo[1,2-a]pyridine-6-boronic acid and 104 mg of [1,1'-bis(diphenylphosphino)ferrocene]dichloro-palladium are degassed under vacuum. After addition of 10 mL of degassed tetrahydrofuran and 0.66 mL of aqueous 2N sodium carbonate solution, the reaction mixture is heated for 2 hours at 100° C. and then cooled, diluted with dichloromethane and washed with aqueous half-saturated sodium bicarbonate solution. The organic phase is dried over magnesium sulfate, filtered and concentrated to dryness under reduced pressure. The residue is chromatographed on silica, eluting with a dichloromethane/methanol mixture (99:1 to 99:2). The fractions containing the expected product are combined and concentrated to dryness under reduced pressure. The solid obtained is washed with 5 mL of diethyl ether to give 125 mg of ethyl 6-(2-{[(1,1-dimethylethoxy)carbonyl]amino}thiazol-4-yl)imidazo[1,2-a]pyridine-2-carboxylate in the form of an off-white solid.

$^1$H NMR spectrum (DMSO-d6, δ in ppm): 11.65 (s, 1H), 8.84 (s, 1H), 8.47 (s, 1H), 7.84 (s, 1H), 7.68-7.71 (m, 2H), 4.32 (q, J=7.1, 2H), 1.51 (s, 9H), 1.33 (t, J=7.1, 3H).

Mass spectrum (APCI): m/z=389 [M+H]$^+$.

14.2: 6-(2-{[(1,1-Dimethylethoxy)carbonyl]amino}thiazol-4-yl)imidazo[1,2-a]pyridine-2-carboxylic acid 125 mg of ethyl 6-(2-{[(1,1-dimethylethoxy)carbonyl]amino}thiazol-4-yl)imidazo[1,2-a]pyridine-2-carboxylate are saponified under conditions similar to those described for the preparation of Intermediate 11 (step 11.3), to give 90 mg of 6-(2-{[(1,1-dimethylethoxy)carbonyl]amino}thiazol-4-yl)imidazo[1,2-a]pyridine-2-carboxylic acid in the form of a brown solid.

$^1$H NMR spectrum (DMSO-d6, δ in ppm): 11.66 (s, 1H), 8.86 (s, 1H), 8.42 (s, 1H), 7.84 (s, 1H), 7.67-7.69 (m, 2H), 1.51 (s, 9H).

Mass spectrum (APCI): m/z=361 [M+H]$^+$.

Intermediate 15: 6-(1H-Pyrrol-3-yl)imidazo[1,2-a]pyridine-2-carboxylic acid

15.1 Ethyl 6-[1-(triisopropylsilyl)-1H-pyrrol-3-yl]imidazo[1,2-a]pyridine-2-carboxylate 100 mg of ethyl 6-iodoimidazo[1,2-a]pyridine-2-carboxylate, 135 mg of 1-(triisopropylsilyl)pyrrole-3-boronic acid and 18 mg of tetrakis(triphenylphosphine)palladium(0) are degassed under vacuum and then suspended, under argon, in a degassed mixture of 1.5 mL of 1,2-dimethoxyethane, 1.5 mL of ethanol and 316 µL of aqueous 2N sodium carbonate solution. The reaction mixture is refluxed for 4 hours and then cooled, diluted and stirred with a mixture of 5 mL of aqueous half-saturated sodium bicarbonate solution and 5 mL of dichloromethane. The organic phase is dried over sodium sulfate, filtered and concentrated to dryness under reduced pressure. The residue is chromatographed on silica, eluting with a mixture of ethyl acetate and hexane (50/50). The fractions containing the expected product are combined and concentrated to dryness under reduced pressure to give 121 mg of ethyl 6-[1-(triisopropylsilyl)-1H-pyrrol-3-yl]imidazo[1,2-a]pyridine-2-carboxylate.

$^1$H NMR spectrum (DMSO-d6, δ in ppm): 8.76 (s, 1H), 8.42 (s, 1H), 7.70 (dd, J=1.9, 9.7 1H), 7.59 (d, J=9.7 1H), 7.37 (broad s, 1H), 6.94 (m, 1H), 6.63 (m, 1H), 4.33 (q, J=6.9, 2H), 1.61-1.50 (m, 3H), 1.33 (t, J=6.9, 3H), 1.10-1.03 (m, 18H).

Mass spectrum (APCI): m/z=412 [M+H]$^+$.

15.2: 6-(1H-Pyrrol-3-yl)imidazo[1,2-a]pyridine-2-carboxylic acid hydrochloride (1:1)

292 mg of ethyl 6-[1-(triisopropylsilyl)-1H-pyrrol-3-yl]imidazo[1,2-a]pyridine-2-carboxylate are saponified under conditions similar to those described for the preparation of Intermediate 11 (step 11.3), to give 140 mg of 6-(1H-pyrrol-3-yl)imidazo[1,2-a]pyridine-2-carboxylic acid hydrochloride (1:1) in the form of a white solid.

$^1$H NMR spectrum (DMSO-d6, δ in ppm): 11.07 (broad s, 1H), 8.73 (s, 1H), 8.39 (s, 1H), 7.69 (dd, J=1.3, 9.5, 1H), 7.59 (d, J=9.5, 1H), 7.31 (s, 1H), 6.86 (s, 1H), 6.46 (s, 1H).

Mass spectrum (APCI): m/z=228 [M+H]$^+$.

Intermediate 16: 6-(1H-Pyrazol-3-yl)imidazo[1,2-a]pyridine-2-carboxylic acid

16.1: Ethyl 6-(1H-pyrazol-3-yl)imidazo[1,2-a]pyridine-2-carboxylate

This product is prepared under conditions similar to those described for the preparation of Intermediate 15 (step 15.1), replacing the 1-(triisopropylsilyl)pyrrole-3-boronic acid with pyrazole-3-boronic acid.

$^1$H NMR spectrum (MeOD-d4, δ in ppm): 8.89 (t, J=1.2, 2.4, 1H), 8.45 (d, J=0.6, 1H), 7.89 (d, J=9.0, 1H), 7.76 (broad s, 1H), 7.67 (d, J=9.5, 1H), 6.77 (d, J=2.4, 1H), 4.42 (q, J=7.1, 2H), 1.43 (t, J=7.1, 3H).

Mass spectrum (APCI): m/z=257 [M+H]$^+$.

16.2: 6-(1H-Pyrazol-3-yl)imidazo[1,2-a]pyridine-2-carboxylic acid 128 mg of ethyl 6-(1H-pyrazol-3-yl)imidazo[1,2-a]pyridine-2-carboxylate are saponified under conditions similar to those described for the preparation of Intermediate 11 (step 11.3) to give 113 mg of 6-(1H-pyrazol-3-yl)imidazo[1,2-a]pyridine-2-carboxylic acid.

$^1$H NMR spectrum (DMSO-d6, δ in ppm): 13.50-12.50 (broad s, 1H), 9.03 (s, 1H), 8.40 (s, 1H), 7.83-7.80 (m, 2H), 7.63 (d, J=9.4, 1H), 6.74 (s, 1H).

Intermediate 17: 6-(1H-Pyrazol-4-yl)imidazo[1,2-a]pyridine-2-carboxylic acid

17.1: Ethyl 6-(1H-pyrazol-4-yl)imidazo[1,2-a]pyridine-2-carboxylate

This product is prepared under conditions similar to those described for the preparation of Intermediate 15 (step 15.1), replacing the 1-(triisopropylsilyl)pyrrole-3-boronic acid with pyrazole-4-boronic acid and heating at 90° C. by microwave for 37 minutes.

$^1$H NMR spectrum (DMSO-d6, δ in ppm): 13.10 (broad s, 1H), 8.83 (s, 1H), 8.43 (s, 1H), 8.25 (broad s, 1H), 7.94 (broad s, 1H), 7.69-7.61 (m, 2H), 4.31 (q, J=7.1, 2H), 1.32 (t, J=7.1, 3H).

Mass spectrum (APCI): m/z=257 [M+H]$^+$.

17.2: 6-(1H-Pyrazol-4-yl)imidazo[1,2-a]pyridine-2-carboxylic acid 128 mg of ethyl 6-(1H-pyrazol-4-yl)imidazo[1,2-a]pyridine-2-carboxylate are saponified under conditions similar to those described for the preparation of Intermediate 11 (step 11.3), to give 60 mg of 6-(1H-pyrazol-4-yl)imidazo[1,2-a]pyridine-2-carboxylic acid.

$^1$H NMR spectrum (DMSO-d6, δ in ppm): 14.0-12.0 (broad s, 1H), 8.84 (s, 1H), 8.36 (s, 1H), 8.10 (s, 2H), 7.64 (s, 2H).

Intermediate 18: 6-(Furan-2-yl)imidazo[1,2-a]pyridine-2-carboxylic acid

18.1: Ethyl 6-(furan-2-yl)imidazo[1,2-a]pyridine-2-carboxylate

This product is prepared under conditions similar to those described for the preparation of Intermediate 15 (step 15.1), replacing the 1-(triisopropylsilyl)pyrrole-3-boronic acid with furan-2-boronic acid.

$^1$H NMR spectrum (DMSO-d6, δ in ppm): 8.78 (s, 1H), 8.44 (s, 1H), 7.72 (dd, J=1.8, 9.6, 1H), 7.63-7.60 (m, 1H), 6.89 (d, J=3.4, 1H), 6.57 (dd, J=1.8, 3.4, 1H), 4.42 (q, J=7.1, 2H), 1.42 (t, J=7.1, 3H).

Mass spectrum (APCI): m/z=257 [M+H]$^+$.

18.2: 6-(Furan-2-yl)imidazo[1,2-a]pyridine-2-carboxylic acid 384 mg of ethyl 6-(furan-2-yl)imidazo[1,2-a]pyridine-2-carboxylate are saponified under conditions similar to those described for the preparation of Intermediate 11 (step 11.3) to give 256 mg of 6-(furan-2-yl)imidazo[1,2-a]pyridine-2-carboxylic acid.

$^1$H NMR spectrum (DMSO-d6, δ in ppm): 8.86 (s, 1H), 8.38 (s, 1H), 7.80 (dd, J=1.7, 9.5, 1H), 7.67-7.64 (m, 2H), 6.90 (d, J=3.4, 1H), 6.60 (dd, J=1.8, 3.4, 1H).

Intermediate 19: 6-(Furan-3-yl)imidazo[1,2-a]pyridine-2-carboxylic acid

19.1: Ethyl 6-(furan-3-yl)imidazo[1,2-a]pyridine-2-carboxylate

This product is prepared under conditions similar to those described for the preparation of Intermediate 15 (step 15.1), replacing the 1-(triisopropylsilyl)pyrrole-3-boronic acid with furan-3-boronic acid.

$^1$H NMR spectrum (DMSO-d6, δ in ppm): 8.86 (s, 1H), 8.45 (s, 1H), 8.28 (s, 1H), 7.82 (s, 1H), 7.66 (s, 2H), 6.95 (s, 1H), 4.31 (q, J=7.1, 2H), 1.33 (t, J=7.1, 3H).

Mass spectrum (APCI): m/z=257 [M+H]$^+$.

19.2: 6-(Furan-3-yl)imidazo[1,2-a]pyridine-2-carboxylic acid 384 mg of ethyl 6-(furan-3-yl)imidazo[1,2-a]pyridine-2-carboxylate are saponified under conditions similar to those described for the preparation of Intermediate 11 (step 11.3) to give 287 mg of 6-(furan-3-yl)imidazo[1,2-a]pyridine-2-carboxylic acid.

$^1$H NMR spectrum (DMSO-d6, δ in ppm): 8.86 (s, 1H), 8.38 (s, 1H), 8.27 (s, 1H), 7.81 (s, 1H), 7.64 (s, 2H), 6.95 (s, 1H).

Mass spectrum (APCI): m/z=229 [M+H]$^+$.

Intermediate 20: 6-[5-(Hydroxymethyl)furan-2-yl]imidazo[1,2-a]pyridine-2-carboxylic acid

20.1: Ethyl 6-(5-formylfuran-2-yl)imidazo[1,2-a]pyridine-2-carboxylate 2 g of ethyl 6-iodoimidazo[1,2-a]pyridine-2-carboxylate, 1.42 g of 5-formylfuran-2-boronic acid and 231 mg of [1,1'-bis(diphenylphosphino)ferrocene]dichloropalladium are degassed under vacuum and then suspended, under argon, in a degassed mixture of 30 mL of dioxane and 9.4 mL of aqueous 2N sodium carbonate solution. The reaction mixture is heated for 5 hours at 90° C., and then stirred for 16 hours at 20° C. and concentrated to dryness. The residue is chromatographed on silica, eluting with a mixture of ethyl acetate and hexane (90/10), with ethyl acetate and then with a mixture (99/1) of ethyl acetate and methanol. The fractions containing the expected product are combined and concentrated to dryness under reduced pressure to give 884 mg of ethyl 6-(5-formylfuran-2-yl)imidazo[1,2-a]pyridine-2-carboxylate.

$^1$H NMR spectrum (DMSO-d6, δ in ppm): 9.64 (s, 1H), 9.20 (s, 1H), 8.66 (s, 1H), 7.86-7.74 (m, 2H), 7.72 (d, J=3.8, 1H), 7.37 (d, J=3.8, 1H), 4.33 (q, J=7.0, 2H), 1.33 (t, J=7.1, 3H).

Mass spectrum (APCI): m/z=285 [M+H]$^+$.

20.2: Ethyl 6-[5-(hydroxymethyl)furan-2-yl]imidazo[1,2-a]pyridine-2-carboxylate To a suspension of 770 mg of ethyl 6-(5-formylfuran-2-yl)imidazo[1,2-a]pyridine-2-carboxylate in 15 mL of ethanol are added 123 mg of sodium borohydride. The reaction mixture is stirred at 25° C. for 90 minutes and then diluted and stirred with 10 mL of dichloromethane and 3 mL of aqueous half-saturated sodium carbonate solution. The organic phase is separated out, dried over magnesium sulfate, filtered and concentrated under reduced pressure. The residue is chromatographed on silica, eluting with a mixture of dichloromethane and methanol (98/2). The fractions containing the expected product are combined and concentrated to dryness under reduced pressure. The solid obtained is triturated in 5 mL of dichloromethane, filtered off and dried to give 403 mg of ethyl 6-(5-formylfuran-2-yl)imidazo[1,2-a]pyridine-2-carboxylate in the form of a white solid.

$^1$H NMR spectrum (DMSO-d6, δ in ppm): 8.89 (s, 1H), 8.60 (s, 1H), 7.70 (m, 2H), 6.98 (d, J=3.3, 1H), 6.45 (d, J=3.3, 1H), 5.30 (t, J=5.3, 1H), 4.47 (d, J=5.6, 2H), 4.32 (q; J=7.1, 2H), 1.32 (t, J=7.1, 3H).

Mass spectrum (APCI): m/z=287 [M+H]$^+$.

20.3: 6-[5-(Hydroxymethyl)furan-2-yl]imidazo[1,2-a]pyridine-2-carboxylic acid 400 mg of ethyl 6-[5-(hydroxymethyl)furan-2-yl]imidazo[1,2-a]pyridine-2-carboxylate are saponified under conditions similar to those described for the preparation of Intermediate 11 (step 11.3) to give 346 mg of 6-[5-(hydroxymethyl)furan-2-yl]imidazo[1,2-a]pyridine-2-carboxylic acid in the form of a white solid.

$^1$H NMR spectrum (DMSO-d6, δ in ppm): 9.06 (s, 1H), 8.73 (s, 1H), 8.03 (d, J=9.5, 1H), 7.82 (d, J=9.5, 1H), 7.09 (d, J=3.3, 1H), 6.49 (d, J=3.2, 1H), 4.49 (s, 2H).

Mass spectrum (APCI): m/z=259 [M+H]$^+$.

Intermediate 21: 6-(Thiophen-3-yl)imidazo[1,2-a]pyridine-2-carboxylic acid

21.1: Ethyl 6-(thiophen-3-yl)imidazo[1,2-a]pyridine-2-carboxylate

This product is prepared under conditions similar to those described for the preparation of Intermediate 15 (step 15.1), replacing the 1-(triisopropylsilyl)pyrrole-3-boronic acid with thiophene-3-boronic acid (catalyst: dichlorobis(triphenylphosphine)palladium).

$^1$H NMR spectrum (DMSO-d6, δ in ppm): 1.34 (d, J=7.1 Hz, 3H), 4.32 (q, J=7.1 Hz, 2H), 7.56 (dd, J=5.0, 1.4 Hz, 1H), 7.68 (d, J=9.8 Hz, 1H), 7.73 (dd, J=5.0, 3.0 Hz, 1H), 7.78 (dd, J=9.8, 1.8 Hz, 1H), 7.97 (dd, J=3.0, 1.4 Hz, 1H), 8.48 (s, 1H), 8.98 (broad s, 1H).

Mass spectrum (LC-MS-DAD-ELSD): m/z 273 [M+H]$^+$.

21.2: 6-(Thiophen-3-yl)imidazo[1,2-a]pyridine-2-carboxylic acid 310 mg of ethyl 6-(thiophen-3-yl)imidazo[1,2-a]pyridine-2-carboxylate are saponified under conditions similar to those described for the preparation of Intermediate 11 (step 11.3) to give 250 mg of 6-(thiophen-3-yl)imidazo[1,2-a]pyridine-2-carboxylic acid.

$^1$H NMR spectrum (DMSO-d6, δ in ppm): 7.57 (d, J=5.4 Hz, 1H), 7.66 (d, J=9.8 Hz, 1H), 7.73 (dd, J=5.4, 2.8 Hz, 1H), 7.76 (dd, J=9.8, 2.0 Hz, 1H), 7.97 (broad d, J=2.0 Hz, 1H), 8.41 (s, 1H), 8.99 (broad s, 1H).

Mass spectrum (LC-MS-DAD-ELSD): m/z 245 [M+H]$^+$.

Intermediate 22: 6-(Oxazol-2-yl)imidazo[1,2-a]pyridine-2-carboxylic acid

22.1: Ethyl 6-(oxazol-2-yl)imidazo[1,2-a]pyridine-2-carboxylate 1 g of ethyl 6-iodoimidazo[1,2-a]pyridine-2-carboxylate, 350 mg of tetrakis(triphenyl-phosphine)palladium(0) and 360 mg of lithium chloride are degassed under vacuum and then suspended, under argon, in 15 mL of degassed dioxane. After addition of 5 g of 2-(tri-n-butylstannyl)oxazole, the reaction mixture is heated at 90° C. for 3.5 hours and then cooled, diluted and stirred with a mixture of 100 mL of aqueous 1M potassium fluoride solution and 200 mL of ethyl acetate. The aqueous phase is extracted with 200 mL of ethyl acetate and the combined organic phases are washed with brine and dried over sodium sulfate, filtered and concentrated to dryness under reduced pressure. The residue is chromatographed on silica, eluting with a gradient of ethyl acetate and hexane (from 80/20 to 100/0). The fractions containing the expected product are combined and concentrated to dryness under reduced pressure to give 530 mg of ethyl 6-(oxazol-2-yl)imidazo[1,2-a]pyridine-2-carboxylate in the form of a yellow powder.

$^1$H NMR spectrum (DMSO-d6, δ in ppm): 9.30 (d, J=0.8, 1H), 8.68 (s, 1H), 8.30 (s, 1H), 7.85 (dd, J=1.7, 9.5, 1H), 7.79 (d, J=9.5, 1H), 7.44 (d, J=0.6, 1H), 4.33 (q, J=7.0, 2H), 1.33 (t, J=7.1, 3H).

Mass spectrum (APCI): m/z=258 [M+H]$^+$.

22.2: 6-(Oxazol-2-yl)imidazo[1,2-a]pyridine-2-carboxylic acid 512 mg of ethyl 6-(oxazol-2-yl)imidazo[1,2-a]pyridine-2-carboxylate are saponified under conditions similar to those described for the preparation of Intermediate 11 (step 11.3) to give 365 mg of 6-(oxazol-2-yl)imidazo[1,2-a]pyridine-2-carboxylic acid in the form of a white solid.

$^1$H NMR spectrum (DMSO-d6, δ in ppm): 9.41 (s, 1H), 8.73 (s, 1H), 8.34 (s, 1H), 8.05 (dd, J=1.5, 9.5, 1H), 7.86 (d, J=9.5, 1H), 7.48 (s, 1H).

Intermediate 23: 6-(1H-1,2,4-Triazol-3-yl)imidazo[1,2-a]pyridine-2-carboxylic acid

23.1: Ethyl 6-[ethoxy(imino)methyl]imidazo[1,2-a]pyridine-2-carboxylate 470 mg of sodium ethanethiolate are added to a solution of 1 g of ethyl 6-cyanoimidazo[1,2-a]pyridine-2-carboxylate (J. Med. Chem. (1998), 41(22), 4317) in a mixture of 15 mL of ethanol and 10 mL of dichloromethane cooled to 0° C. The reaction mixture is stirred for 5 hours at 25° C. and filtered, and the filtrate is evaporated to dryness. The residue is chromatographed on silica, eluting with a mixture of dichloromethane and methanol (98/2) to give 625 mg of ethyl 6-[ethoxy(imino)methyl]imidazo[1,2-a]pyridine-2-carboxylate in the form of a pale yellow solid.

$^1$H NMR spectrum (DMSO-d6, δ in ppm): 9.17 (s, 1H), 9.04 (s, 1H), 8.64 (s, 1H), 7.84 (m, 1H), 7.68 (m, 1H), 4.33 (q, J=7.1, 4H), 1.34 (t=7.2, 6H).

Mass spectrum (APCI): m/z=262 [M+H]$^+$.

23.2: Ethyl 6-[hydrazino(imino)methyl]imidazo[1,2-a]pyridine-2-carboxylate

To a solution of 625 mg of ethyl 6-[ethoxy(imino)methyl]imidazo[1,2-a]pyridine-2-carboxylate in 12 mL of ethanol is added dropwise at 0-5° C. 0.2 mL of hydrazine hydrate. The reaction mixture is stirred for 2 hours, a further 73 µL of hydrazine hydrate are added and the mixture is stirred for a further 2 hours while allowing the temperature to rise to 25° C. The reaction mixture is concentrated to dryness under reduced pressure and the residue is dried to give 600 mg of ethyl 6-[hydrazino(imino)methyl]imidazo[1,2-a]pyridine-2-carboxylate, which is used without further purification in the rest of the synthesis.

$^1$H NMR spectrum (DMSO-d6, δ in ppm): 8.77 (broad s, 1H), 8.49 (s, 1H), 7.70 (m, 1H), 7.53 (d, J=9.6, 1H), 5.67 (s, 2H), 5.15 (broad s, 2H), 4.33 (q, J=7.1, 2H), 1.32 (t=7.1, 3H).

Mass spectrum (APCI): m/z=248 [M+H]$^+$.

23.3: Ethyl 6-(1H-1,2,4-triazol-3-yl)imidazo[1,2-a]pyridine-2-carboxylate

A suspension of 580 mg of ethyl 6-[hydrazino(imino)methyl]imidazo[1,2-a]pyridine-2-carboxylate in 6 mL of formic acid is heated for 20 hours at 85° C. The reaction mixture is concentrated to less than 20% of its initial volume and diluted with 20 mL of water. Solid sodium carbonate is added at 0-5° C. to obtain a pH of 8-9. The precipitate is filtered off by suction, and then purified by chromatography on silica, eluting with a mixture of dichloromethane and methanol (98/2) to give 320 mg of ethyl 6-(1H-1,2,4-triazol-3-yl)imidazo[1,2-a]pyridine-2-carboxylate.

$^1$H NMR spectrum (DMSO-d6, δ in ppm): 14.5-14.0 (broad s, 1H), 9.25 (s, 1H), 8.69 (s, 1H), 8.63 (broad s, 1H), 7.94 (dd, J=9.5, 1.5, 1H), 7.73 (d, J=9.5, 1H), 4.33 (q, J=7.0, 2H), 1.33 (t=7.0, 3H)

Mass spectrum (APCI): m/z=258 [M+H]$^+$.

23.4: 6-(1H-1,2,4-Triazol-3-yl)imidazo[1,2-a]pyridine-2-carboxylic acid 320 mg of ethyl 6-(1H-1,2,4-triazol-3-yl)imidazo[1,2-a]pyridine-2-carboxylate are saponified under conditions similar to those described for the preparation of Intermediate 11 (step 11.3) to give 238 mg of 6-(1H-1,2,4-triazol-3-yl)imidazo[1,2-a]pyridine-2-carboxylic acid in the form of an off-white solid.

$^1$H NMR spectrum (DMSO-d6, δ in ppm): 14.5-14.2 (broad s, 1H), 9.26 (s, 1H), 8.66-8.62 (m, 2H), 7.91 (d, J=9.1, 1H), 7.73 (d, J=9.6, 1H).

Intermediate 24: 6-(1H-1,2,3-Triazol-4-yl)imidazo[1,2-a]pyridine-2-carboxylic acid

24.1: Ethyl 6-[(trimethylsilyl)ethynyl]imidazo[1,2-a]pyridine-2-carboxylate A mixture of 4 g of ethyl 6-iodoimidazo[1,2-a]pyridine-2-carboxylate, 2.63 mL of ethynyltrimethylsilane and 888 mg of dichlorobis(triphenylphosphine)palladium is degassed under vacuum. 240 mg of degassed N,N-dimethylformamide and 3.52 mL of triethylamine are added. The reaction mixture is degassed under argon, stirred at 50° C. for 50 hours and then cooled and diluted with 20 mL of water. The precipitate is filtered off by suction and washed with 5 mL of water and then chromatographed on silica, eluting with mixtures of ethyl acetate and hexane (from 50/50 to 90/10). The fractions containing the expected product are combined and concentrated to dryness under reduced pressure to give 3.6 g of ethyl 6-[(trimethylsilyl)ethynyl]imidazo[1,2-a]pyridine-2-carboxylate in the form of an off-white solid.

$^1$H NMR spectrum (DMSO-d6, δ in ppm): 8.61 (s, 1H), 8.22 (s, 1H), 7.36 (d, J=9.5, 1H), 7.07 (dd, J=9.5, 1.7, 1H), 4.07 (q, J=7.1, 2H), 1.08 (t, J=7.1, 3H), 0.01 (s, 9H).

Mass spectrum (APCI): m/z=287 [M+H]$^+$.

24.2: Ethyl 6-ethynylimidazo[1,2-a]pyridine-2-carboxylate

To a solution of 500 mg of ethyl 6-[(trimethylsilyl)ethynyl]imidazo[1,2-a]pyridine-2-carboxylate in 10 mL of anhydrous tetrahydrofuran, cooled to 0° C. are added dropwise 1.58 mL of a 1M solution of tetrabutylammonium fluoride in tetrahydrofuran. The reaction mixture is stirred for 30 minutes, 5 mL of water are then added and the resulting mixture is extracted three times with 20 mL of dichloromethane. The product is purified by chromatography on silica, eluting with mixtures of ethyl acetate and hexane (from 1/3 to 1/1). The fractions containing the expected product are combined and concentrated to dryness under reduced pressure to give 280 mg of ethyl 6-ethynylimidazo[1,2-a]pyridine-2-carboxylate in the form of a yellow solid.

$^1$H NMR spectrum (DMSO-d6, δ in ppm): 8.86 (d, J=1.0, 1H), 8.50 (d, J=0.6, 1H), 7.63 (d, J=9.4, 1H), 7.37 (d, J=1.7, 9.4, 1H), 4.32 (m, 3H), 1.32 (t, J=7.1 Hz, 3H).

Mass spectrum (APCI): m/z=215 [M+H]$^+$.

24.3: Ethyl 6-(1H-1,2,3-triazol-4-yl)imidazo[1,2-a]pyridine-2-carboxylate

To a solution of 220 mg of ethyl 6-ethynylimidazo[1,2-a]pyridine-2-carboxylate and 0.21 mL of azidotrimethylsilane in 4 mL of a mixture (9/1) of N,N-dimethylformamide and methanol are added 9.8 mg of cuprous iodide. The reaction mixture is stirred for 2 hours at 100° C. and then cooled, diluted with 4 mL of dichloromethane, filtered through alumina and concentrated to dryness. The residue is chromatographed on silica, eluting with a mixture of dichloromethane and ethanol (97/3). The fractions containing the expected product are combined and concentrated to dryness under reduced pressure to give 125 mg of ethyl 6-(1H-1,2,3-triazol-4-yl)imidazo[1,2-a]pyridine-2-carboxylate in the form of an off-white solid.

$^1$H NMR spectrum (DMSO-d6, δ in ppm): 15.5-15.0 (broad s, 1H), 9.14 (dd, J=1.1, 1.5, 1H), 8.60 (d, J=0.5, 1H), 8.40 (broad s, 1H), 7.82 (dd, J=1.7, 9.5, 1H), 7.75 (d, J=9.5, 1H), 4.33 (q, J=7.1, 2H), 1.33 (t, J=7.1, 3H).

Mass spectrum (APCI): m/z=258 [M+H]$^+$.

24.4: 6-(1H-1,2,3-Triazol-4-yl)imidazo[1,2-a]pyridine-2-carboxylic acid 125 mg of ethyl 6-(1H-1,2,3-triazol-3-yl)imidazo[1,2-a]pyridine-2-carboxylate are saponified under conditions similar to those described for the preparation of Intermediate 11 (step 11.3), to give 72 mg of 6-(1H-1,2,3-triazol-3-yl)imidazo[1,2-a]pyridine-2-carboxylic acid in the form of a white solid.

$^1$H NMR spectrum (DMSO-d6, δ in ppm): 16.0-15.0 (broad s, 1H), 9.23 (s, 1H), 8.62 (s, 1H), 8.46 (broad s, 1H), 7.96 (dd, J=1.4, 9.5, 1H), 7.80 (d, J=9.5, 1H).

Intermediate 25: Ethyl 6-(4,4,5,5-tetramethyl-1,3,2-dioxaborolan-2-yl)imidazo[1,2-a]pyridine-2-carboxylate hydrobromide (1:1)

To a solution of 4 g of 2-amino-5-(4,4,5,5-tetramethyl-1,3,2-dioxaborolan-2-yl)pyridine in 40 mL of 1,2-dimethoxyethane are added 4.26 g of ethyl 3-bromo-2-oxopropionate. The reaction mixture is stirred for 40 hours at 20° C. The precipitate is filtered off by suction, washed with a small amount of 1,2-dimethoxyethane and pentane and then taken up in 50 mL of ethanol and refluxed for 1 hour. The reaction mixture is concentrated to dryness under reduced pressure. The oil obtained is redissolved in ethyl ether and the solution is concentrated under reduced pressure. The solid is filtered off by suction and washed with a small amount of ethyl ether to give 3.78 g of ethyl 6-(4,4,5,5-tetramethyl-1,3,2-dioxaborolan-2-yl)imidazo[1,2-a]pyridine-2-carboxylate hydrobromide (1:1) in the form of a white solid.

$^1$H NMR spectrum (DMSO-d6, δ in ppm): 1.27-1.38 (m, 15H), 4.36 (q, J=7.3 Hz, 2H), 7.59 (d, J=9.3 Hz, 1H), 7.67 (d, J=9.3 Hz, 1H), 8.68 (s, 1H), 8.97 (s, 1H).
Mass spectrum (EI): m/z 316 [M]$^+$, 244 [M−CO$_2$Et+H]$^+$.

Intermediate 26: 2-Ethoxycarbonylimidazo[1,2-a]pyridine-6-boronic acid

To a solution of 2.5 g of 2-amino-5-(4,4,5,5-tetramethyl-1,3,2-dioxaborolan-2-yl)pyridine in 50 mL of 1,2-dimethoxyethane are added 2.14 mL of ethyl 3-bromo-2-oxopropionate. The reaction mixture is stirred for 3.5 hours at 25° C., 50 mL of ethanol are then added and the resulting mixture is refluxed for 16 hours. The reaction mixture is cooled and concentrated to dryness. The residue is suspended in 100 mL of water at 0° C. and treated, while stirring vigorously, with solid sodium carbonate until a pH of 8-9 is obtained. The precipitate is filtered off by suction and washed with 100 mL of water at 0° C. and then dissolved in 150 mL of methanol. The solution is dried over magnesium sulfate, filtered, concentrated and dried under vacuum to give 2.36 g of 2-ethoxycarbonylimidazo[1,2-a]pyridine-6-boronic acid in the form of a cream-coloured solid.

$^1$H NMR spectrum (DMSO-d6, δ in ppm): 8.82 (d, J=0.9, 1H), 8.58 (s, 1H), 8.35 (s, 2H) 7.61 (m, 2H), 4.33 (m, 2H), 1.32 (m, 3H).
Mass spectrum (APCI): m/z=235 [M+H]$^+$.

The tables that follow illustrate the chemical structures (Table 1), the spectroscopic characteristics and the synthetic methods (Table 2) of a few examples of compounds according to the invention.

In this table:
- the ratio in parentheses is the (acid/base) ratio, "HCl" represents a compound in hydrochloride form, "TFA" represents a compound in trifluoroacetate form and the ratio indicated in parentheses is the (acid/base) ratio, the sign "-" means that the compound is in base form;
- "—CH$_3$" means methyl,

TABLE 1

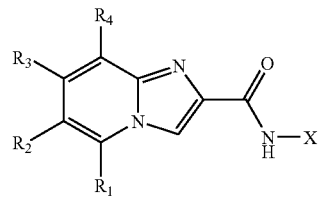

(I)

| Ex | R$_1$ | R$_2$ | R$_3$ | R$_4$ | X | salt | Method |
|---|---|---|---|---|---|---|---|
| 1 | H | ⟨1,3-dioxolan-2-yl⟩ | H | H | Ph | — | Ex 1 |
| 2 | H | ⟨pyridin-3-yl⟩ | H | H | Ph | — | Ex 2 |
| 3 | H | ⟨pyridin-2-yl⟩ | H | H | Ph | — | Ex 3 |
| 4 | H | ⟨5-(hydroxymethyl)pyridin-3-yl⟩ | H | H | Ph | — | Ex 4 |
| 5 | H | ⟨4-(hydroxymethyl)pyridin-3-yl⟩ | H | H | Ph | HCl (1:1) | Ex 5 |

TABLE 1-continued
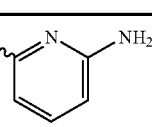
(I)
| Ex | R₁ | R₂ | R₃ | R₄ | X | salt | Method |
|---|---|---|---|---|---|---|---|
| 6 | H |  | H | H | Ph | HCl (1:1) | Ex 6 |
| 7 | H |  | H | H | Ph | HCl (1:1) | Ex 7 |
| 8 | H |  | H | H | Ph | — | Ex 8 |
| 9 | H |  | H | H | Ph | — | Ex 9 |
| 10 | H |  | H | H | Ph | — | Ex 10 |
| 11 | H |  | H | H | Ph | — | Ex 11 |
| 12 | H |  | H | H | Ph | — | Ex 12 |
| 13 | H |  | H | H | Ph | TFA (1:1) | Ex 13 |
| 14 | H |  | H | H | Ph | — | Ex 14 |
| 15 | H |  | H | H | Ph | — | Ex 15 |
| 16 | H |  | H | H | Ph | — | Ex 16 |
| 17 | H | 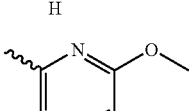 | H | H | Ph | HCl (1:1); HCl (1:2) | Ex 17 |
| 18 | H |  | H | H | Ph | — | Ex 18 |

TABLE 1-continued
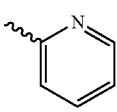
| Ex | R₁ | R₂ | R₃ | R₄ | X | salt | Method |
|---|---|---|---|---|---|---|---|
| 19 | —CH₃ | 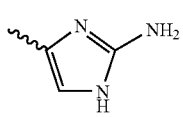 | H | H | Ph | — | Ex 19 |
| 20 | H | 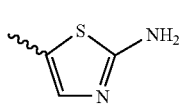 | H | H | Ph | TFA (1:1) | Ex 20 |
| 21 | H | 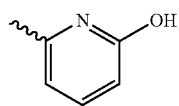 | H | H | Ph | — | Ex 21 |
| 22 | H | 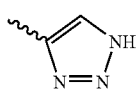 | H | H | Ph | — | Ex 22 |
| 23 | H | 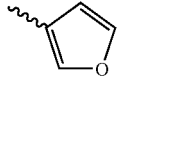 | H | H | Ph | — | Ex 23 |
| 24 | H | 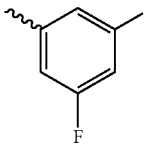 | H | H | 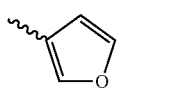 | — | Ex 24 |
| 25 | H | 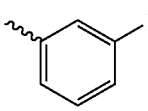 | H | H | 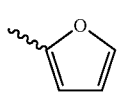 | — | Ex 25 |
| 26 | H | 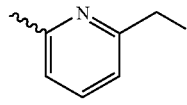 | H | H | Ph | — | As per Ex 3 |
| 27 | H | 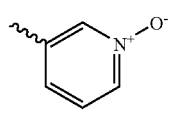 | H | H | Ph | HCl (1:1) | As per Ex 5 |
| 28 | H | 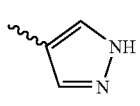 | H | H | Ph | HCl (1:1) | As per Ex 5 |
| 29 | H |  | H | H | Ph | — | As per Ex 8 |

TABLE 1-continued (I)

| Ex | R₁ | R₂ | R₃ | R₄ | X | salt | Method |
|---|---|---|---|---|---|---|---|
| 30 | H | 2-imidazolyl (NH) | H | H | Ph | TFA (1:1) | As per Ex 9 |
| 31 | H | 1-methyl-4-imidazolyl | H | H | Ph | — | As per Ex 7 |
| 32 | H | 2-oxazolyl | H | H | Ph | — | As per Ex 3 |
| 33 | H | 2-pyridyl | H | H | 3,5-difluorophenyl | — | As per Ex 3 |
| 34 | H | 4-pyridyl | H | H | Ph | — | As per Ex. 2 |
| 35 | H | 3-indolyl | H | H | Ph | — | As per Ex 8 |
| 36 | H | 2-thienyl | H | H | Ph | — | As per Ex 7 |
| 37 | H | 2-pyrazinyl | H | H | Ph | — | As per Ex 7 |
| 38 | H | 2-pyridyl N-oxide | H | H | Ph | — | As per Ex 18 |
| 39 | H | 5-pyrimidinyl | H | H | Ph | — | As per Interm. 20 and 1 |

TABLE 1-continued
(I)
| Ex | R₁ | R₂ | R₃ | R₄ | X | salt | Method |
|---|---|---|---|---|---|---|---|
| 40 | H |  | H | H | Ph | — | As per Ex 8 |
| 41 | H |  | H | H | Ph | — | As per Interm. 11 and 1 |
| 42 | H |  | H | H |  | — | As per Ex 25 |
| 43 | H |  | H | H |  | — | As per Ex 25 |
| 44 | H |  | H | H |  | — | As per Ex 25 |
| 45 | H |  | H | H |  | — | As per Ex 25 |
| 46 | H |  | H | H |  | — | As per Ex 25 |
| 47 | H |  | H | H |  | — | As per Ex 25 |
| 48 | H |  | H | H |  | — | As per Ex 25 |
| 49 | H |  | H | H |  | — | As per Ex 25 |
| 50 | H |  | H | H | | — | As per Ex 25 |

TABLE 1-continued
(I)
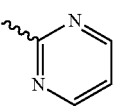
| Ex | R₁ | R₂ | R₃ | R₄ | X | salt | Method |
|----|----|----|----|----|---|------|--------|
| 51 | H | 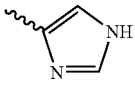 | H | H | Ph | — | As per Ex 18 |
| 52 | H | 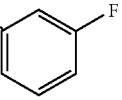 | H | H | 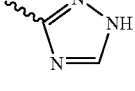 | — | As per Ex 25 |
| 53 | H | 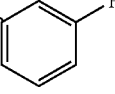 | H | H | 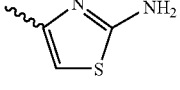 | — | As per Ex 25 |
| 54 | H | 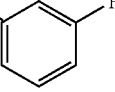 | H | H | 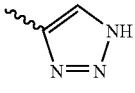 | — | As per Ex 25 |
| 55 | H | 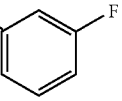 | H | H | 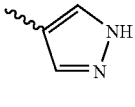 | — | As per Ex 25 |
| 56 | H | 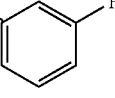 | H | H | 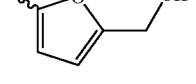 | — | As per Ex 25 |
| 57 | H | 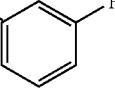 | H | H | 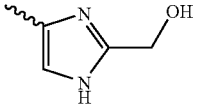 | — | As per Ex 25 |
| 58 | H | 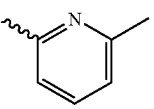 | H | H | Ph | — | As per Ex 4 |
| 59 | H | 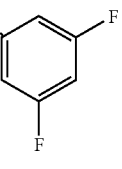 | H | H | 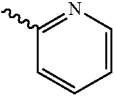 | — | As per Ex 25 |
| 60 | H | 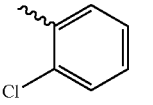 | H | H | (2-Cl-phenyl) | — | As per Ex 25 |

TABLE 1-continued
| Ex | R₁ | R₂ | R₃ | R₄ | X | salt | Method |
|---|---|---|---|---|---|---|---|
| 61 | H | 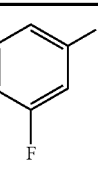 | H | H |  | — | As per Ex 25 |
| 62 | H | 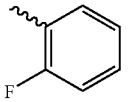 | H | H |  | — | As per Ex 25 |
| 63 | H | 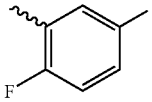 | H | H |  | — | As per Ex 25 |
| 64 | H | 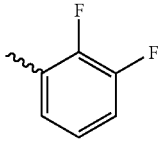 | H | H |  | — | As per Ex 25 |
| 65 | H | 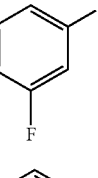 | H | H |  | — | As per Ex 25 |
| 66 | H | 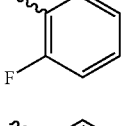 | H | H |  | — | As per Ex 25 |
| 67 | H | 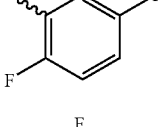 | H | H |  | — | As per Ex 25 |
| 68 | H | 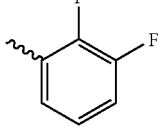 | H | H |  | — | As per Ex 25 |
| 69 | H | 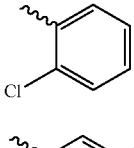 | H | H |  | — | As per Ex 25 |
| 70 | H |  | H | H | | — | As per Ex 25 |

TABLE 1-continued (I)

| Ex | R₁ | R₂ | R₃ | R₄ | X | salt | Method |
|---|---|---|---|---|---|---|---|
| 71 | H | oxazol-2-yl | H | H | 2-chlorophenyl | — | As per Ex 25 |
| 72 | H | furan-3-yl | H | H | 2-fluorophenyl | — | As per Ex 25 |
| 73 | H | furan-3-yl | H | H | 2,5-difluorophenyl | — | As per Ex 25 |
| 74 | H | furan-3-yl | H | H | 2,3-difluorophenyl | — | As per Ex 25 |
| 75 | H | furan-3-yl | H | H | 2-chlorophenyl | — | As per Ex 25 |
| 76 | H | 5-(hydroxymethyl)furan-2-yl | H | H | 2,3-difluorophenyl | — | As per Ex 25 |
| 77 | H | 1H-1,2,4-triazol-3-yl | H | H | 2-fluorophenyl | — | As per Ex 25 |
| 78 | H | 1H-1,2,4-triazol-3-yl | H | H | 2-chlorophenyl | — | As per Ex 25 |
| 79 | H | pyridin-2-yl | H | H | 2-cyanophenyl | — | As per Ex 25 |
| 80 | H | 6-aminopyridin-2-yl | H | H | 3,5-difluorophenyl | HCl (1:2) | As per Ex 25 |

TABLE 1-continued
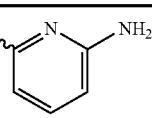
(I)
| Ex | R₁ | R₂ | R₃ | R₄ | X | salt | Method |
|---|---|---|---|---|---|---|---|
| 81 | H | 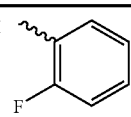 | H | H | 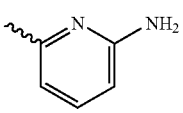 | HCl (1:2) | As per Ex 25 |
| 82 | H | 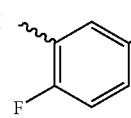 | H | H | 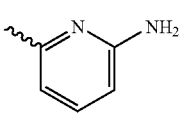 | HCl (1:2) | As per Ex 25 |
| 83 | H | 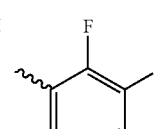 | H | H | 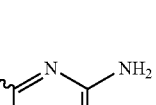 | HCl (1:2) | As per Ex 25 |
| 84 | H | 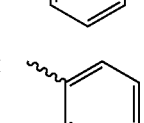 | H | H | 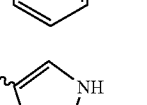 | HCl (1:2) | As per Ex 25 |
| 85 | H | 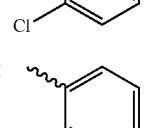 | H | H | 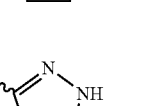 | — | As per Ex 25 |
| 86 | H | 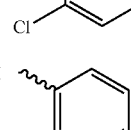 | H | H | 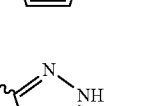 | — | As per Ex 25 |
| 87 | H | 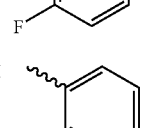 | H | H | 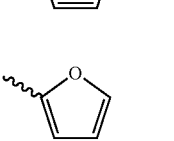 | — | As per Ex 25 |
| 88 | H | 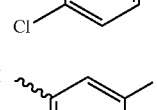 | H | H |  | — | As per Ex 25 |
| 89 | H | 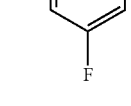 | H | H | 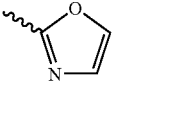 | — | As per Ex 25 |
| 90 | H | 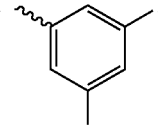 | H | H | 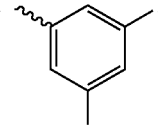 | — | As per Ex 25 |

TABLE 1-continued (I)

| Ex | R₁ | R₂ | R₃ | R₄ | X | salt | Method |
|---|---|---|---|---|---|---|---|
| 91 | H | oxazol-2-yl | H | H | 2,3-difluorophenyl | — | As per Ex 25 |
| 92 | H | 5-(hydroxymethyl)furan-2-yl | H | H | 3,5-difluorophenyl | — | As per Ex 25 |
| 93 | H | 5-(hydroxymethyl)furan-2-yl | H | H | 2,5-difluorophenyl | — | As per Ex 25 |
| 94 | H | 1H-imidazol-4-yl | H | H | 2,3-difluorophenyl | — | As per Ex 25 |
| 95 | H | 1H-1,2,4-triazol-3-yl | H | H | 2,5-difluorophenyl | — | As per Ex 25 |
| 96 | H | 1H-1,2,4-triazol-3-yl | H | H | 2,3-difluorophenyl | — | As per Ex 25 |
| 97 | H | 1H-1,2,3-triazol-4-yl | H | H | 3,5-difluorophenyl | — | As per Ex 25 |
| 98 | H | 1H-1,2,3-triazol-4-yl | H | H | 2-fluorophenyl | — | As per Ex 25 |
| 99 | H | 1H-1,2,3-triazol-4-yl | H | H | 2,5-difluorophenyl | — | As per Ex 25 |

TABLE 1-continued

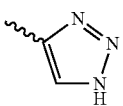

(I)

| Ex | R₁ | R₂ | R₃ | R₄ | X | salt | Method |
|----|----|----|----|----|----|------|--------|
| 100 | H | 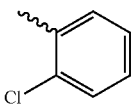 | H | H | (2-chlorophenyl) | — | As per Ex 25 |

TABLE 2

| Ex | Characterizations |
|----|-------------------|
| 1 | $^1$H NMR spectrum (DMSO-d6, δ in ppm): from 3.97 to 4.14 (m, 4H), 5.87 (s, 1H), 7.10 (t, J = 7.5 Hz, 1H), 7.33 (t, J = 7.5 Hz, 2H), 7.41 (dd, J = 2.0 and 9.5 Hz, 1H), 7.69 (d, J = 9.5 Hz, 1H), 7.90 (d, J = 7.5 Hz, 2H), 8.54 (s, 1H), 8.77 (broad s, 1H), 10.3 (s, 1H). Mass spectrum (LC-MS-DAD-ELSD): m/z 310 [M + H]⁺. |
| 2 | $^1$H NMR spectrum (DMSO-d6, δ in ppm): 7.10 (t, J = 8.0 Hz, 1H), 7.35 (broad t, J = 8.0 Hz, 2H), 7.56 (broad dd, J = 5.0 and 8.0 Hz, 1H), from 7.76 to 7.83 (m, 2H), 7.91 (broad d, J = 8.0 Hz, 2H), 8.16 (td, J = 1.5 and 8.0 Hz, 1H), 8.52 (s, 1H), 8.64 (dd, J = 1.5 and 5.0 Hz, 1H), 8.98 (m, 1H), 9.09 (t, J = 1.5 Hz, 1H), 10.3 (s, 1H). Mass spectrum (LC-MS-DAD-ELSD): m/z 315 [M + H]⁺. |
| 3 | $^1$H NMR spectrum (DMSO-d6, δ in ppm): 7.10 (t, J = 7.5 Hz, 1H), 7.36 (t, J = 7.5 Hz, 2H), 7.43 (dd, J = 5.0 and 8.0 Hz, 1H), 7.78 (d, J = 9.5 Hz, 1H), 7.91 (d, J = 7.5 Hz, 2H), 7.97 (dt, J = 2.0 and 8.0 Hz, 1H), 8.03 (d, J = 9.5 Hz, 1H), 8.12 (dd, J = 2.0 and 8.0 Hz, 1H), 8.62 (s, 1H), 8.72 (broad d, J = 5.0 Hz, 1H), 9.43 (s, 1H), 10.3 (s, 1H). Mass spectrum (LC-MS-DAD-ELSD): m/z 315 [M + H]⁺. |
| 4 | $^1$H NMR spectrum (DMSO-d6, δ in ppm): 4.64 (d, J = 5.5 Hz, 2H), 5.41 (t, J = 5.5 Hz, 1H), 7.10 (t, J = 7.5 Hz, 1H), 7.35 (t, J = 7.5 Hz, 2H), 7.79 (s, 2H), 7.90 (d, J = 7.5 Hz, 2H), 8.08 (broad s, 1H), 8.53 (s, 1H), 8.59 (broad s, 1H), 8.84 (broad s, 1H), 9.10 (broad s, 1H), 10.25 (s, 1H). Mass spectrum (LC-MS-DAD-ELSD): m/z 345 [M + H]⁺; m/z 389 [M + HCO₂]⁻. |
| 5 | $^1$H NMR spectrum (DMSO-d6, δ in ppm): 4.68 (s, 2H), 7.12 (t, J = 8.0 Hz, 2H), 7.38 (t, J = 8.0 Hz, 2H), 7.42 (broad d, J = 5.0 Hz, 1H), 7.82 (d, J = 9.5 Hz, 1H), 7.89 (d, J = 8.0 Hz, 2H), 8.00 (broad s, 1H), 8.21 (broad d, J = 9.5 Hz, 1H), 8.67 (d, J = 5.0 Hz, 1H), 8.72 (s, 1H), 9.51 (broad s, 1H), 10.45 (broad s, 1H). Mass spectrum (LC-MS-DAD-ELSD): m/z 345 [M + H]⁺. |
| 6 | $^1$H NMR spectrum (DMSO-d6, δ in ppm): 6.89 (broad d, J = 7.9 Hz, 1H), 7.11 (tt, J = 7.6, 1.2 Hz, 1H), 7.23 (dd, J = 7.9, 1.1 Hz, 1H), 7.32-7.41 (m, 2H), 7.62 (very broad m, 3H), 7.84 (d, J = 9.6 Hz, 1H), 7.81-7.97 (m, 4H), 8.67 (s, 1H), 9.29 (t, J = 1.1 Hz, 1H), 10.45 (s, 1H). Mass spectrum (LC-MS-DAD-ELSD): m/z 330 [M + H]⁺. |
| 7 | $^1$H NMR spectrum (DMSO-d6, δ in ppm): 7.10 (t, J = 7.5 Hz, 1H), 7.37 (t, J = 7.5 Hz, 2H), 7.80 (s, 1H), 7.90 (d, J = 7.5 Hz, 2H), 8.09 (broad s, 1H), 8.62 (s, 1H), 8.84 (broad m, 1H), 9.09 (s, 1H), 10.3 (s, 1H). Mass spectrum (LC-MS-DAD-ELSD): m/z 304 [M + H]⁺. |
| 8 | $^1$H NMR spectrum (DMSO-d6, δ in ppm): 6.76 (d, J = 3.0 Hz, 1H), 7.10 (t, J = 7.5 Hz, 1H), 7.34 (t, J = 7.5 Hz, 2H), 7.71 (d, J = 9.5 Hz, 1H), from 7.81 to 7.92 (m, 4H), 8.51 (s, 1H), 9.09 (s, 1H), 10.2 (s, 1H), 13.05 (broad m, 1H). Mass spectrum (LC-MS-DAD-ELSD): m/z 304 [M + H]⁺, m/z 302 [M − H]⁻. |
| 9 | $^1$H NMR spectrum (DMSO-d6, δ in ppm): 7.10 (t, J = 7.5 Hz, 1H), 7.36 (t, J = 7.5 Hz, 2H), 7.78 (d, J = 9.5 Hz, 1H), 7.90 (d, J = 7.5 Hz, 2H), 7.99 (dd, J = 1.5 and 9.5 Hz, 1H), 8.61 (broad s, 1H), 8.68 (s, 1H), 9.30 (broad s, 1H), 10.25 (s, 1H), 14.0 (very broad m, 1H). Mass spectrum (LC-MS-DAD-ELSD): m/z 305 [M + H]⁺, m/z 303 [M − H]⁻. |
| 10 | $^1$H NMR spectrum (DMSO-d6, δ in ppm): 6.48 (broad s, 1H), 6.89 (broad s, 1H), 7.10 (t, J = 7.5 Hz, 1H), 7.30 (broad s, 1H), 7.34 (t, J = 7.5 Hz, 2H), 7.60 (d, J = 9.5 Hz, 1H), 7.68 (dd, J = 1.5 and 9.5 Hz, 1H), 7.89 (d, J = 7.5 Hz, 2H), 8.40 (s, 1H), 8.76 (broad s, 1H), 10.15 (broad s, 1H), 11.05 (broad m, 1H). Mass spectrum (LC-MS-DAD-ELSD): m/z 303 [M + H]⁺, m/z 301 [M − H]⁻. |
| 11 | $^1$H NMR spectrum (DMSO-d6, δ in ppm): 2.33 (s, 3H), 7.09 (t, J = 7.5 Hz, 1H), 7.33 (t, J = 7.5 Hz, 2H), 7.54 (broad s, 1H), 7.61 (d, J = 9.5 Hz, 1H), 7.72 (dd, J = 1.5 and 9.5 Hz, 1H), 7.89 (d, J = 7.5 Hz, 2H), 8.53 (s, 1H), 9.93 (broad s, 1H), 10.2 (s, 1H), 11.95 (broad m, 1H). Mass spectrum (LC-MS-DAD-ELSD): m/z 318 [M + H]⁺. |
| 12 | $^1$H NMR spectrum (DMSO-d6, δ in ppm): 6.99 (broad s, 1H), 7.10 (t, J = 7.5 Hz, 1H), 7.33 (t, J = 7.5 Hz, 2H), 7.69 (broad s, 2H), 7.82 (t, J = 1.5 Hz, 1H), 7.90 (d, J = 7.5 Hz, 2H), 8.30 (broad s, 1H), 8.42 (s, 1H), 8.92 (broad s, 1H), 10.25 (s, 1H). Mass spectrum (LC-MS-DAD-ELSD): m/z 304 [M + H]⁺. |

TABLE 2-continued

| Ex | Characterizations |
|---|---|
| 13 | $^1$H NMR spectrum (DMSO-d6, δ in ppm): 7.11 (t, J = 8.0 Hz, 1H), 7.36 (t, J = 8.0 Hz, 2H), 7.65 (broad s, 1H), 7.79 (dd, J = 2.0 and 9.5 Hz, 1H), 7.90 (m, 3H), 8.05 (broad s, 1H), 8.60 (s, 1H), 9.11 (broad s, 1H), 9.20 (broad s, 1H), 10.3 (s, 1H).<br>Mass spectrum (LC-MS-DAD-ELSD): m/z 304 [M + H]$^+$. |
| 14 | $^1$H NMR spectrum (DMSO-d6, δ in ppm): 7.10 (t, J = 7.5 Hz, 1H), 7.35 (t, J = 7.5 Hz, 2H), 7.78 (m, 3H), 7.90 (d, J = 7.5 Hz, 2H), 8.54 (s, 1H), 8.60 (s, 1H), 9.07 (broad s, 1H), 10.25 (s, 1H).<br>Mass spectrum (LC-MS-DAD-ELSD): m/z 305 [M + H]$^+$. |
| 15 | $^1$H NMR spectrum (DMSO-d6, δ in ppm): 7.10 (t, J = 7.5 Hz, 1H), 7.15 (m, 3H), 7.33 (t, J = 7.5 Hz, 2H), 7.64 (d, J = 9.5 Hz, 1H), 7.81 (dd, J = 1.5 and 9.5 Hz, 1H), 7.89 (d, J = 7.5 Hz, 2H), 8.61 (s, 1H), 8.92 (broad s, 1H), 10.2 (s, 1H).<br>Mass spectrum (LC-MS-DAD-ELSD): m/z 336 [M + H]$^+$, m/z 334 [M − H]$^-$. |
| 16 | $^1$H NMR spectrum (DMSO-d6, δ in ppm): 1.64 (s, 3H), 3.82 (m, 2H), 4.03 (m, 2H), 7.10 (t, J = 7.5 Hz, 1H), 7.34 (t, J = 7.5 Hz, 2H), 7.39 (dd, J = 1.5 and 9.5 Hz, 1H), 7.64 (d, J = 9.5 Hz, 1H), 7.90 (d, J = 7.5 Hz, 2H), 8.53 (s, 1H), 8.68 (broad s, 1H), 10.2 (broad s, 1H).<br>Mass spectrum (LC-MS-DAD-ELSD): m/z 324 [M + H]$^+$. |
| 17 | HCl (1:1) salt:<br>$^1$H NMR spectrum (DMSO-d6, δ in ppm): 4.04 (s, 4H), 7.12 (dt, J = 7.3, 1.2 Hz, 1H), 7.31-7.40 (m, 2H), 7.82 (dd, J = 9.6, 1.9 Hz, 1H), 7.87-7.95 (m, 3H), 8.76 (d, J = 0.8 Hz, 1H), 9.47 (dd, J = 1.9, 0.8 Hz, 1H), 10.46 (s, 1H), 10.89 (broad s, 2H).<br>Mass spectrum (LC-MS-DAD-ELSD): m/z 305 [M + H]$^+$. |
| 18 | $^1$H NMR spectrum (DMSO-d6, δ in ppm): 4.01 (s, 3H), 6.85 (d, J = 8.0 Hz, 1H), 7.10 (t, J = 7.7 Hz, 1H), 7.35 (t, J = 7.7 Hz, 2H), 7.61 (d, J = 8.0 Hz, 1H), 7.76 (d, J = 9.8 Hz, 1H), 7.85 (t, J = 8.0 Hz, 1H), 7.91 (d, J = 7.7 Hz, 2H), 8.11 (broad d, J = 9.8 Hz, 1H), 8.61 (s, 1H), 9.40 (broad s, 1H), 10.26 (s, 1H).<br>Mass spectrum (LC-MS-DAD-ELSD): m/z 345 [M + H]$^+$. |
| 19 | $^1$H NMR spectrum (DMSO-d6, δ in ppm): 2.74 (s, 3H), 7.10 (tt, dd, J = 7.6, 1.2 Hz, 1H), 7.36 (broad t, J = 7.6 Hz, 2H), 7.45 (ddd, J = 7.6, 4.8, 1.2 Hz, 1H), 7.57 (d, J = 9.3 Hz, 1H), 7.64-7.71 (m, 2H), 7.89-8.00 (m, 3H), 8.53 (d, J = 0.8 Hz, 1H), 8.74 (ddd, J = 4.8, 1.9, 0.9 Hz, 1H), 10.30 (s, 1H).<br>Mass spectrum (LC-MS-DAD-ELSD): m/z 329 [M + H]$^+$. |
| 20 | $^1$H NMR spectrum (DMSO-d6, δ in ppm): 7.10 (t, J = 7.7 Hz, 1H), 7.27-7.49 (m, 6H), 7.62 (dd, J = 9.6, 2.2 Hz, 1H), 7.72 (d, J = 9.6 Hz, 1H), 7.84 (broad d, J = 7.7 Hz, 2H), 8.49 (d, J = 0.8 Hz, 1H), 8.84 (broad s, 1H), 9.98 (broad s, 1H), 12.51 (broad m, 1H).<br>Mass spectrum (LC-MS-DAD-ELSD): m/z 319 [M + H]$^+$. |
| 21 | $^1$H NMR spectrum (DMSO-d6, δ in ppm): 7.09 (tt, J = 7.8, 1.2 Hz, 1H), 7.29 (broad s, 2H), 7.34 (broad t, J = 7.8 Hz, 2H), 7.49 (s, 1H), 7.63 (d, J = 9.5 Hz, 1H), 7.67 (dd, J = 9.5, 2.0 Hz, 1H), 7.89 (broad d, J = 7.8 Hz, 2H), 8.45 (s, 1H), 8.62 (broad s, 1H), 10.19 (s, 1H).<br>Mass spectrum (LC-MS-DAD-ELSD): m/z 336 [M + H]$^+$, m/z 334 [M − H]$^-$. |
| 22 | $^1$H NMR spectrum (DMSO-d6, δ in ppm): 6.52 (broad d, J = 8.4 Hz, 1H), 6.99 (broad m, 1H), 7.10 (broad t, J = 7.7 Hz, 1H), 7.35 (t, J = 7.7 Hz, 2H), 7.66 (broad t, J = 8.4 Hz, 1H), 7.74 (d, J = 9.4 Hz, 1H), 7.84 (broad d, J = 9.4 Hz, 1H), 7.90 (d, J = 7.7 Hz, 2H), 8.58 (s, 1H), 9.16 (broad s, 1H), 10.29 (s, 1H), 11.8 (very broad m, 1H). |
| 23 | $^1$H NMR spectrum (DMSO-d6, δ in ppm): 7.10 (t, J = 7.8 Hz, 1H), 7.35 (t, J = 7.8 Hz, 2H), 7.75 (d, J = 9.5 Hz, 1H), 7.87 (dd, J = 9.5, 1.7 Hz, 1H), 7.90 (d, J = 7.8 Hz, 2H), 8.42 (s, 1H), 8.57 (s, 1H), 9.20 (broad s, 1H), 10.26 (s, 1H), 15.3 (very broad m, 1H).<br>Mass spectrum (LC-MS-DAD-ELSD): m/z 305 [M + H]$^+$, m/z 303 [M − H]$^-$. |
| 24 | $^1$H NMR spectrum (DMSO-d6, δ in ppm): 6.93 (tt, J = 9.5, 2.4 Hz, 1H), 6.98 (s, 1H), 7.70 (s, 2H), 7.74 (dd, J = 9.5, 2.4 Hz, 2H), 7.82 (s, 1H), 8.29 (s, 1H), 8.47 (s, 1H), 8.93 (s, 1H), 10.74 (s, 1H).<br>Mass spectrum (LC-MS-DAD-ELSD): m/z 340 [M + H]$^+$. |
| 25 | $^1$H NMR spectrum (DMSO-d6, δ in ppm): 6.92 (td, J = 8.3, 2.3, 1.0 Hz, 1H), 6.98 (dd, J = 1.5, 0.9 Hz, 1H), 7.38 (td, J = 8.3, 6.8 Hz, 1H), 7.69 (d, J = 1.4 Hz, 2H), 7.74 (ddd, J = 8.3, 2.3, 0.9 Hz, 1H), 7.82 (t, J = 1.5 Hz, 1H), 7.88 (dt, J = 12.3, 2.3 Hz, 1H), 8.29 (dd, J = 1.5, 0.9 Hz, 1H), 8.45 (s, 1H), 8.93 (t, J = 1.4 Hz, 1H), 10.50 (s, 1H).<br>Mass spectrum (LC-MS-DAD-ELSD): m/z 322 [M + H]$^+$. |
| 26 | $^1$H NMR spectrum (DMSO-d6, δ in ppm): 6.68 (dd, J = 2.0 and 3.5 Hz, 1H), 7.07 (d, J = 3.5 Hz, 1H), 7.10 (t, J = 7.5 Hz, 1H), 7.35 (t, J = 7.5 Hz, 2H), 7.71 (d, J = 9.5 Hz, 1H), 7.77 (dd, J = 2.0 and 9.5 Hz, 1H), 7.84 (d, J = 2.0 Hz, 1H), 7.90 (d, J = 7.5 Hz, 2H), 8.58 (s, 1H), 9.00 (broad s, 1H), 10.3 (s, 1H).<br>Mass spectrum (LC-MS-DAD-ELSD): m/z 304 [M + H]$^+$. |
| 27 | $^1$H NMR spectrum (DMSO-d6, δ in ppm): 4.69 (s, 2H), 7.11 (t, J = 8.0 Hz, 1H), 7.37 (t, J = 8.0 Hz, 2H), 7.51 (d, J = 8.0 Hz, 1H), 7.79 (d, J = 9.5 Hz, 1H), 7.89 (m, 3H), 7.98 (t, J = 8.0 Hz, 1H), 8.17 (broad d, J = 9.5 Hz, 1H), 8.67 (s, 1H), 9.42 (broad s, 1H), 10.35 (broad s, 1H).<br>Mass spectrum (LC-MS-DAD-ELSD): m/z 345 [M + H]$^+$. |
| 28 | $^1$H NMR spectrum (DMSO-d6, δ in ppm): 7.11 (t, J = 7.5 Hz, 1H), 7.37 (t, J = 7.5 Hz, 2H), 7.59 (dd, J = 6.0 and 8.0 Hz, 1H), 7.74 (broad d, J = 8.0 Hz, 1H), 7.80 (d, J = 9.5 Hz, 1H), 7.85 (dd, J = 2.0 and 9.5 Hz, 1H), 7.90 (d, J = 7.5 Hz, 2H), 8.30 (broad d, J = 6.0 Hz, 1H), 8.55 (s, 1H), 8.71 (t, J = 1.5 Hz, 1H), 9.20 (broad s, 1H), 10.4 (broad s, 1H).<br>Mass spectrum (LC-MS-DAD-ELSD): m/z 331 [M + H]$^+$; m/z 329 [M − H]$^-$. |
| 29 | $^1$H NMR spectrum (DMSO-d6, δ in ppm): 7.10 (t, J = 8.0 Hz, 1H), 7.33 (t, J = 8.0 Hz, 2H), 7.69 (m, 2H), 7.89 (d, J = 8.0 Hz, 2H), 8.11 (broad m, 2H), 8.40 (s, 1H), 8.90 (s, 1H), 10.2 (s, 1H), 13.05 (broad m, 1H).<br>Mass spectrum (LC-MS-DAD-ELSD): m/z 304 [M + H]$^+$, m/z 302 [M − H]$^-$. |
| 30 | $^1$H NMR spectrum (DMSO-d6, δ in ppm): 7.11 (t, J = 7.5 Hz, 1H), 7.37 (t, J = 7.5 Hz, 2H), 7.60 (s, 2H), from 7.83 to 7.95 (m, 4H), 8.70 (s, 1H), 9.23 (s, 1H), 10.3 (s, 1H) (broad signals).<br>Mass spectrum (LC-MS-DAD-ELSD): m/z 304 [M + H]$^+$, m/z 302 [M − H]$^-$. |

TABLE 2-continued

| Ex | Characterizations |
|---|---|
| 31 | $^1$H NMR spectrum (DMSO-d6, δ in ppm): 3.71 (s, 3H), 7.10 (t, J = 7.5 Hz, 1H), 7.34 (t, J = 7.5 Hz, 2H), 7.65 (d, J = 9.5 Hz, 1H), 7.69 (s, 1H), 7.71 (s, 1H), 7.73 (dd, J = 1.5 and 9.5 Hz, 1H), 7.89 (d, J = 7.5 Hz, 2H), 8.55 (s, 1H), 8.97 (broad s, 1H), 10.2 (broad s, 1H). Mass spectrum (LC-MS-DAD-ELSD): m/z 318 [M + H]$^+$. |
| 32 | $^1$H NMR spectrum (DMSO-d6, δ in ppm): 7.10 (t, J = 7.5 Hz, 1H), 7.35 (t, J = 7.5 Hz, 2H), 7.46 (s, 1H), 7.81 (d, J = 9.5 Hz, 1H), 7.90 (m, 3H), 8.31 (s, 1H), 8.67 (s, 1H), 9.38 (broad s, 1H), 10.3 (s, 1H). Mass spectrum (LC-MS-DAD-ELSD): m/z 305 [M + H]$^+$. |
| 33 | $^1$H NMR spectrum (DMSO-d6, δ in ppm): 6.94 (tt, J = 9.3, 2.4 Hz, 1H), 7.43 (ddd, J = 7.2, 4.8, 1.3 Hz, 1H), 7.69-7.82 (m, 3H), 7.92-8.05 (m, 2H), 8.12 (dd, J = 9.6, 1.9 Hz, 1H), 8.66 (d, J = 1.0 Hz, 1H), 8.71 (ddd, J = 4.8, 1.8, 1.0 Hz, 1H), 9.43 (dd, J = 1.9, 1.0 Hz, 1H), 10.79 (s, 1H). Mass spectrum (LC-MS-DAD-ELSD): m/z 351 [M + H]$^+$. |
| 34 | $^1$H NMR spectrum (DMSO-d6, δ in ppm): 7.10 (t, J = 8.0 Hz, 1H), 7.35 (broad t, J = 8.0 Hz, 2H), from 7.77 to 7.87 (m, 4H), 7.91 (broad d, J = 8.0 Hz, 2H), 8.54 (s, 1H), 8.71 (m, 2H), 9.22 (broad s, 1H), 10.3 (s, 1H). Mass spectrum (LC-MS-DAD-ELSD): m/z 315 [M + H]$^+$. |
| 35 | $^1$H NMR spectrum (DMSO-d6, δ in ppm): 7.10 (tt, J = 7.7, 1.2 Hz.1H), 7.13-7.26 (m, 2H), 7.35 (broad t, J = 7.7 Hz, 1H), 7.50 (broad d, J = 7.3 Hz, 1H), 7.71 (dt, J = 9.5, 0.9 Hz, 1H), 7.79 (dd, J = 9.5, 2.2 Hz, 1H), 7.87 (d, J = 2.8 Hz, 1H), 7.91 (broad d, J = 7.8 Hz, 2H), 8.00 (broad d, J = 7.8 Hz, 1H), 8.58 (d, J = 0.8 Hz, 1H), 8.99 (broad s, 1H), 10.21 (s, 1H), 11.50 (broad s, 1H). Mass spectrum (LC-MS-DAD-ELSD): m/z 353 [M + H]$^+$, m/z 351 [M − H]$^-$. |
| 36 | $^1$H NMR spectrum (DMSO-d6, δ in ppm): 7.10 (broad t, J = 7.7 Hz, 1H), 7.20 (dd, J = 5.4, 3.7 Hz, 1H), 7.35 (t, J = 7.7 Hz, 2H), 7.59 (dd, J = 3.7, 1.5 Hz, 1H), 7.63 (d, J = 5.4, 1.5 Hz, 1H), 7.66-7.78 (m, 2H), 7.90 (m, 2H), 8.52 (s, 1H), 9.01 (broad s, 1H), 10.25 (s, 1H). |
| 37 | $^1$H NMR spectrum (DMSO-d6, δ in ppm): 7.10 (broad t, J = 7.8 Hz, 1H), 7.35 (t, J = 7.8 Hz, 2H), 7.82 (d, J = 9.8 Hz, 1H), 7.91 (broad d, J = 7.8 Hz, 2H), 8.14 (dd, J = 9.8, 1.9 Hz, 1H), 8.63 (broad s, 1H), 8.68 (d, J = 2.7 Hz, 1H), 8.77 (dd, J = 2.7, 1.5 Hz.1H), 9.32 (broad d, J = 1.5 Hz, 1H), 9.51 (dd, J = 1.9, 1.0 Hz, 1H), 10.31 (s, 1H). Mass spectrum (LC-MS-DAD-ELSD): m/z 316 [M + H]$^+$. |
| 38 | $^1$H NMR spectrum (DMSO-d6, δ in ppm): 7.10 (tt, J = 7.7, 1.2 Hz, 1H), 7.35 (broad t, J = 7.7 Hz, 2H), 7.43-7.53 (m, 2H), 7.71 (dd, J = 9.6, 0.9 Hz, 1H), 7.79-7.86 (m, 2H), 7.91 (broad d, J = 7.7 Hz, 2H), 8.42 (m, 1H), 8.61 (d, J = 0.8 Hz, 1H), 9.36 (broad s, 1H), 10.28 (s, 1H). Mass spectrum (LC-MS-DAD-ELSD): m/z 331 [M + H]$^+$. |
| 39 | $^1$H NMR spectrum (DMSO-d6, δ in ppm): 7.10 (broad t, J = 7.7 Hz, 1H), 7.35 (t, J = 7.7 Hz, 2H), 7.82 (broad d, J = 9.8 Hz, 1H), 7.86 (dd, J = 9.8, 1.5 Hz, 1H), 7.91 (d, J = 7.7 Hz, 2H), 8.52 (s, 1H), 9.18 (broad s, 1H), 9.22 (s, 2H), 9.25 (s, 1H), 10.30 (s, 1H). Mass spectrum (LC-MS-DAD-ELSD): m/z 316 [M + H]$^+$. |
| 40 | $^1$H NMR spectrum (DMSO-d6, δ in ppm): 7.10 (broad t, J = 7.8 Hz, 1H), 7.35 (t, J = 7.8 Hz, 2H), 7.59 (dd, J = 5.1, 1.5 Hz, 1H), 7.71 (d, J = 9.8 Hz, 1H), 7.74 (dd, J = 5.1, 2.9 Hz, 1H), 7.81 (dd, J = 9.8, 2.0 Hz, 1H), 7.90 (m, 2H), 7.99 (dd, J = 2.9, 1.5 Hz, 1H), 8.46 (s, 1H), 9.05 (broad s, 1H), 10.24 (s, 1H). Mass spectrum (LC-MS-DAD-ELSD): m/z 320 [M + H]$^+$. |
| 41 | $^1$H NMR spectrum (DMSO-d6, δ in ppm): 5.99 (dd, J = 7.0, 3.6 Hz, 1H), 7.06 (t, J = 3.6 Hz, 1H), 7.09 (tt, J = 7.7, 1.4 Hz, 1H), 7.33 (t, J = 7.7 Hz, 2H), 7.67-7.76 (m, 2H), 7.89 (m, 2H), 8.53 (s, 1H), 8.91 (s, 1H), 10.22 (s, 1 H). Mass spectrum (LC-MS-DAD-ELSD): m/z 322 [M + H]$^+$. |
| 42 | $^1$H NMR spectrum (DMSO-d6, δ in ppm): 6.92 (m, 1H), 7.33-7.45 (m, 2H), 7.76 (m, 2H), 7.89 (dt, J = 11.6, 2.4 Hz, 1H), 7.96 (td, J = 7.8, 1.6 Hz, 1H), 8.03 (dt, J = 7.8, 1.6 Hz, 1H), 8.12 (dd, J = 9.6, 1.9 Hz, 1H), 8.64 (d, J = 0.8 Hz, 1H), 8.71 (ddd, J = 4.8, 1.8, 1.0 Hz, 1H), 9.43 (dd, J = 1.9, 0.8 Hz, 1H), 10.55 (s, 1H). Mass spectrum (LC-MS-DAD-ELSD): m/z 333 [M + H]$^+$. |
| 43 | $^1$H NMR spectrum (DMSO-d6, δ in ppm): 7.16-7.38 (m, 3H), 7.43 (ddd, J = 7.5, 4.7, 1.3 Hz, 1H), 7.81 (d, J = 9.6 Hz, 1H), 7.96 (td, J = 7.5, 1.3 Hz, 1H), 8.03 (broad d, J = 7.5 Hz, 1H), 8.06-8.15 (m, 2H), 8.65 (s, 1H), 8.71 (broad d, J = 4.7 Hz, 1H), 9.43 (broad s, 1H), 9.85 (broad s, 1H). Mass spectrum (LC-MS-DAD-ELSD): m/z 333 [M + H]$^+$. |
| 44 | $^1$H NMR spectrum (DMSO-d6, δ in ppm): 7.06 (m, 1H), 7.45-7.47 (m, 2H), 7.82 (broad d, J = 9.8 Hz, 1H), 7.91-8.06 (m, 3H), 8.14 (dd, J = 9.8, 1.7 Hz, 1H), 8.69 (d, J = 0.9 Hz, 1H), 8.71 (broad d, J = 5.4 Hz, 1H), 9.43 (broad s, 1H), 9.89 (broad s, 1H). Mass spectrum (LC-MS-DAD-ELSD): m/z 351 [M + H]$^+$. |
| 45 | $^1$H NMR spectrum (DMSO-d6, δ in ppm): 7.17-7.33 (m, 2H), 7.43 (ddd, J = 7.9, 4.8, 1.0 Hz, 1H), 7.77 (partially masked m, 1H), 7.80 (dt, J = 9.6, 0.9 Hz, 1H), 7.96 (dt, J = 7.9, 1.8 Hz, 1H), 8.03 (dt, J = 7.9, 1.0 Hz, 1H), 8.13 (dd, J = 9.6, 1.8 Hz, 1H), 8.66 (d, J = 0.9 Hz, 1H), 8.71 (ddd, J = 4.8, 1.8, 1.0 Hz, 1H), 9.43 (dd, J = 1.8, 0.9 Hz, 1H), 10.09 (broad s, 1H). Mass spectrum (LC-MS-DAD-ELSD): m/z 351 [M + H]$^+$. |
| 46 | $^1$H NMR spectrum (DMSO-d6, δ in ppm): 6.07 (broad s, 2H), 6.49 (dd, J = 8.3, 0.9 Hz, 1H), 6.92 (broad td, J = 8.3, 2.5 Hz, 1H), 7.09 (dd, J = 7.4, 0.9 Hz, 1H), 7.38 (td, J = 8.3, 6.9 Hz, 1H), 7.52 (dd, J = 8.3, 7.4 Hz, 1H), 7.70 (dt, J = 9.6, 0.9 Hz, 1H), 7.75 (broad dd, J = 8.3, 1.8 Hz, 1H), 7.88 (dt, J = 11.7, 2.5 Hz, 1H), 7.99 (dd, J = 9.7, 1.8 Hz, 1H), 8.62 (d, J = 0.9 Hz, 1H), 9.19 (dd, J = 1.8, 0.9 Hz, 1H), 10.52 (broad s, 1H). Mass spectrum (LC-MS-DAD-ELSD): m/z 348 [M + H]$^+$. |
| 47 | $^1$H NMR spectrum (DMSO-d6, δ in ppm): 6.47 (td, J = 2.8, 1.7 Hz, 1H), 6.84-6.95 (m, 2H), 7.31 (dt, J = 2.8, 1.7 Hz, 1H), 7.37 (td, J = 8.3, 6.8 Hz, 1H), 7.60 (dt, J = 9.4, 0.9 Hz, 1H), 7.67 (dd, J = 9.4, 1.6 Hz, 1H), 7.74 (broad d, J = 8.3 Hz, 1H), 7.88 (dt, J = 12.1, 2.6 Hz, 1H), 8.42 (d, J = 0.9 Hz, 1H), 8.76 (broad s, 1H), 10.45 (broad s, 1H), 11.06 (broad m, 1H). Mass spectrum (LC-MS-DAD-ELSD): m/z 321 [M + H]$^+$. |

TABLE 2-continued

| Ex | Characterizations |
|---|---|
| 48 | $^1$H NMR spectrum (DMSO-d6, δ in ppm): 6.77 (broad s, 1H), 6.92 (td, J = 8.5, 2.6 Hz, 1H), 7.38 (td, J = 8.3, 6.8 Hz, 1H), 7.67-7.78 (m, 2H), 7.84-7.92 (m, 3H), 8.55 (s, 1H), 9.09 (broad s, 1H), 10.51 (broad s, 1H), 13.05 (broad s, 1H).<br>Mass spectrum (LC-MS-DAD-ELSD): m/z 322 [M + H]$^+$, m/z 320 [M − H]$^-$. |
| 49 | $^1$H NMR spectrum (DMSO-d6, δ in ppm): 6.66 (dd, J = 3.4, 1.9 Hz, 1H), 6.85-6.97 (tdd, J = 8.5, 2.5, 1.0 Hz, 1H), 7.05 (dd, J = 3.4, 0.8 Hz, 1H), 7.38 (td, J = 8.3, 6.8 Hz, 1H), 7.66-7.79 (m, 3H), 7.83 (dd, J = 1.9, 0.8 Hz, 1H), 7.87 (d, J = 11.9, 2.5 Hz, 1H), 8.58 (d, J = 0.6 Hz, 1H), 8.99 (t, J = 1.5 Hz, 1H), 10.51 (broad s, 1H).<br>Mass spectrum (LC-MS-DAD-ELSD): m/z 322 [M + H]$^+$. |
| 50 | $^1$H NMR spectrum (DMSO-d6, δ in ppm): 6.92 (tdd, J = 8.5, 2.6, 1.0 Hz, 1H), 7.38 (td, J = 8.5, 6.8 Hz, 1H), 7.45 (d, J = 0.9 Hz, 1H), 7.76 (ddd, J = 8.5, 2.6, 1.0 Hz, 1H), 7.81 (dt, J = 9.5, 1.0 Hz, 1H), 7.88 (dt, J = 12.0, 2.6 Hz.1H), 7.92 (dd, J = 9.5, 1.9 Hz, 1H), 8.31 (d, J = 0.9 Hz, 1H), 8.69 (d, J = 1.0 Hz, 1H), 9.38 (dd, J = 1.9, 1.0 Hz, 1H), 10.58 (broad s, 1H).<br>Mass spectrum (LC-MS-DAD-ELSD): m/z 323 [M + H]$^+$. |
| 51 | $^1$H NMR spectrum (DMSO-d6, δ in ppm): 7.10 (tt, J = 7.5, 1.3 Hz, 1H), 7.35 (t, J = 7.8 Hz, 2H), 7.52 (t, J = 4.9 Hz, 1H), 7.79 (d, J = 9.8 Hz, 1H), 7.91 (m, 2H), 8.30 (dd, J = 9.8, 1.7 Hz, 1H), 8.74 (s, 1H), 8.96 (d, J = 4.9 Hz, 2H), 9.69 (broad s, 1H), 10.31 (s, 1H).<br>Mass spectrum (LC-MS-DAD-ELSD): m/z 316 [M + H]$^+$. |
| 52 | $^1$H NMR spectrum (DMSO-d6, δ in ppm): 6.91 (tdd, J = 8.3, 2.2, 1.0 Hz, 1H), 7.37 (td, J = 8.3, 6.8 Hz, 1H), 7.65 (dt, J = 9.5, 0.9 Hz, 1H), 7.69-7.79 (m, 3H), 7.81 (dd, J = 9.5, 1.7 Hz, 1H), 7.87 (dt, J = 11.7, 2.2 Hz, 1H), 8.58 (d, J = 0.9 Hz, 1H), 9.00 (dd, J = 1.7, 0.9 Hz, 1H), 10.46 (s, 1H), 12.28 (broad m, 1H).<br>Mass spectrum (LC-MS-DAD-ELSD): m/z 322 [M + H]$^+$, m/z 320 [M − H]$^-$. |
| 53 | $^1$H NMR spectrum (DMSO-d6, δ in ppm): 6.92 (tdd, J = 8.4, 2.6, 1.1 Hz, 1H), 7.38 (td, J = 8.4, 6.9 Hz, 1H), 7.72-7.81 (m, 2H), 7.88 (ddt, J = 12.1, 2.2 Hz, 1H), 7.99 (broad d, J = 9.6 Hz, 1H), 8.69 (s, 1H), 8.71 (broad s, 1H), 9.32 (broad s, 1H), 10.54 (broad s, 1H), 14.26 (broad m, 1H).<br>Mass spectrum (LC-MS-DAD-ELSD): m/z 323 [M + H]$^+$. |
| 54 | $^1$H NMR spectrum (DMSO-d6, δ in ppm): 6.91 (tdd, J = 8.5, 2.6, 1.0 Hz, 1H), 7.38 (td, J = 8.5, 6.8 Hz, 1H), 7.67-7.82 (m, 4H), 7.86 (dt, J = 12.0, 2.2 Hz, 1H), 8.55 (s, 1H), 8.86 (broad s, 1H), 8.90 (broad m, 2H), 10.61 (s, 1H).<br>Mass spectrum (LC-MS-DAD-ELSD): m/z 354 [M + H]$^+$, m/z 352 [M − H]$^-$. |
| 55 | $^1$H NMR spectrum (DMSO-d6, δ in ppm): 6.92 (tdd, J = 8.5, 2.6, 1.0 Hz, 1H), 7.38 (td, J = 8.3, 6.8 Hz, 1H), 7.73-7.79 (m, 2H), 7.84-7.92 (m, 2H), 8.44 (broad m, 1H), 8.60 (broad s, 1H), 9.20 (broad s, 1H), 10.53 (broad s, 1H), 15.24 (broad m, 1H).<br>Mass spectrum (LC-MS-DAD-ELSD): m/z 323 [M + H]$^+$. |
| 56 | $^1$H NMR spectrum (DMSO-d6, δ in ppm): 6.86-6.98 (tdd, J = 8.4, 2.7, 0.8 Hz, 1H), 7.37 (td, J = 8.4, 6.8 Hz, 1H), 7.63-7.78 (m, 3H), 7.88 (dt, J = 11.8, 2.3 Hz, 1H), 7.99 (broad m, 1H), 8.24 (broad m, 1H), 8.44 (s, 1H), 8.90 (t, J = 1.4 Hz, 1H), 10.48 (broad s, 1H), 13.07 (broad m, 1H).<br>Mass spectrum (LC-MS-DAD-ELSD): m/z 322 [M + H]$^+$, m/z 320 [M − H]$^-$. |
| 57 | $^1$H NMR spectrum (DMSO-d6, δ in ppm): 4.49 (d, J = 5.5 Hz, 2H), 5.30 (t, J = 5.5 Hz, 1H), 6.47 (d, J = 3.4 Hz, 1H), 6.91 (tdd, J = 8.4, 2.3, 0.9 Hz, 1H), 6.98 (d, J = 3.4 Hz, 1H), 7.37 (td, J = 8.4, 6.8 Hz, 1H), 7.67-7.77 (m, 3H), 7.87 (ddd, J = 12.1, 2.3 Hz, 1H), 8.60 (s, 1H), 8.95 (t, J = 1.4 Hz, 1H), 10.50 (s, 1H).<br>Mass spectrum (LC-MS-DAD-ELSD): m/z 352 [M + H]$^+$, m/z 350 [M − H]$^-$. |
| 58 | $^1$H NMR spectrum (DMSO-d6, δ in ppm): 4.53 (d, J = 5.6 Hz, 2H), 5.37-5.47 (m, 1H), 7.09 (t, J = 7.6 Hz, 1H), 7.34 (t, J = 7.6 Hz, 2H), 7.59-7.67 (m, 2H), 7.78 (dd, J = 9.5, 1.5 Hz, 1H), 7.89 (d, J = 7.6 Hz, 2H), 8.54 (s, 1H), 8.96 (s, 1H), 10.16 (broad s, 1H), 12.15 (broad m, 1H).<br>Mass spectrum (LC-MS-ES+/−): m/z 332 [M + H]$^-$, m/z 334 [M + H]$^+$ |
| 59 | $^1$H NMR spectrum (DMSO-d6, δ in ppm): 2.58 (s, 3H), 6.90-6.97 (m, 1H), 7.29 (d, J = 6.8 Hz, 1H), 7.75 (d, J = 9.5 Hz, 3H) 7.79-7.87 (m, 2H) 8.10 (dd, J = 9.5, 1.7 Hz, 1H), 8.67 (s, 1H), 9.37 (broad s, 1H), 10.77 (broad s, 1H).<br>Mass spectrum (LC-MS-ES+/−): m/z 363 [M + H]$^-$, m/z 365 [M + H]$^+$ |
| 60 | $^1$H NMR spectrum (DMSO-d6, δ in ppm): 7.21 (td, J = 7.9, 1.6 Hz, 1H), 7.38-7.47 (m, 2H), 7.59 (dd, J = 7.9, 1.6 Hz, 1H), 7.82 (d, J = 9.6 Hz, 1H), 7.92-8.07 (m, 2H), 8.14 (dd, J = 9.6, 1.8 Hz, 1H), 8.36 (dd, J = 8.3, 1.6 Hz, 1H), 8.67-8.74 (m, 2H), 9.43 (broad s, 1H), 9.96 (broad s, 1H).<br>Mass spectrum (LC-MS-ES+/−): m/z 349 [M + H]$^+$ |
| 61 | $^1$H NMR spectrum (DMSO-d6, δ in ppm): 6.47 (m, 1H), 6.88 (m, 1H), 6.91 (tt, J = 9.2, 2.4 Hz, 1H), 7.31 (m, 1H), 7.60 (d, J = 9.5 Hz, 1H), 7.68 (dd, J = 9.5, 1.8 Hz, 1H), 7.74 (m, 2H), 8.44 (s, 1H), 8.76 (broad s, 1H), 10.69 (broad s, 1H), 11.06 (broad m, 1H).<br>Mass spectrum (LC-MS-ES+/−): m/z 337 [M + H]$^-$, m/z 339 [M + H]$^+$ |
| 62 | $^1$H NMR spectrum (DMSO-d6, δ in ppm): 6.47 (m, 1H), 6.87 (m, 1H), 7.13-7.38 (m, 4H), 7.64 (d, J = 9.5 Hz, 1H), 7.70 (dd, J = 9.5, 1.7 Hz, 1H), 8.13 (td, J = 7.8, 2.0 Hz, 1H), 8.43 (s, 1H), 8.76 (broad s, 1H), 9.76 (broad s, 1H), 11.05 (broad m, 1H).<br>Mass spectrum (LC-MS-ES+/−): m/z 319 [M + H]$^-$, m/z 321 [M + H]$^+$ |
| 63 | $^1$H NMR spectrum (DMSO-d6, δ in ppm): 6.47 (m, 1H), 6.87 (m, 1H), 7.03 (m, 1H), 7.32 (m, 1H), 7.40 (ddd, J = 10.4, 9.1, 5.0 Hz, 1H), 7.65 (d, J = 9.5 Hz, 1H), 7.71 (dd, J = 9.5, 1.7 Hz, 1H), 8.04 (ddd, J = 10.4, 6.2, 3.3 Hz, 1H), 8.46 (s, 1H), 8.76 (broad s, 1H), 9.81 (broad s, 1H), 11.07 (broad m, 1H).<br>Mass spectrum (LC-MS-ES+/−): m/z 337 [M + H]$^-$, m/z 339 [M + H]$^+$ |
| 64 | $^1$H NMR spectrum (DMSO-d6, δ in ppm): 6.47 (m, 1H), 6.87 (m, 1H), 7.17-7.29 (m, 2H), 7.32 (m, 1H), 7.64 (d, J = 9.5 Hz, 1H), 7.70 (dd, J = 9.5, 1.7 Hz, 1H), 7.83 (m, 1H), 8.44 (s, 1H), 8.76 (broad s, 1H), 9.98 (broad s, 1H), 11.05 (broad m, 1H).<br>Mass spectrum (LC-MS-ES+/−): m/z 337 [M + H]$^-$, m/z 339 [M + H]$^+$ |

TABLE 2-continued

| Ex | Characterizations |
|---|---|
| 65 | ¹H NMR spectrum (DMSO-d6, δ in ppm): 6.76 (d, J = 2.2 Hz, 1H), 6.93 (tt, J = 9.4, 2.4 Hz, 1H), 7.67-7.94 (m, 5H), 8.56 (s, 1H), 9.09 (broad s, 1H), 10.74 (broad s, 1H), 13.05 (broad m, 1H).<br>Mass spectrum (LC-MS-ES+/−): m/z 338 [M + H]⁻, m/z 340 [M + H]⁺ |
| 66 | ¹H NMR spectrum (DMSO-d6, δ in ppm): 6.66 (dd, J = 3.4, 1.9 Hz, 1H), 7.06 (d, J = 3.4 Hz, 1H), 7.16-7.39 (m, 3H), 7.77 (m, 2H), 7.83 (d, J = 1.9 Hz, 1H), 8.04-8.14 (m, 1H), 8.59 (s, 1H), 8.98 (broad s, 1H), 9.80 (broad s, 1H).<br>Mass spectrum (LC-MS-ES+/−): m/z 322 [M + H]⁺ |
| 67 | ¹H NMR spectrum (DMSO-d6, δ in ppm): 6.66 (dd, J = 3.4, 1.9 Hz, 1H), 6.97-7.13 (m, 2H), 7.40 (ddd, J = 10.5, 9.1, 5.0 Hz, 1H), 7.72-7.82 (m, 2H), 7.83 (dd, J = 1.9, 0.9 Hz, 1H), 8.01 (ddd, J = 10.3, 6.2, 3.2 Hz, 1H), 8.62 (s, 1H), 8.98 (broad s, 1H), 9.84 (broad s, 1H).<br>Mass spectrum (LC-MS-ES+/−): m/z 340 [M + H]⁺ |
| 68 | ¹H NMR spectrum (DMSO-d6, δ in ppm): 6.66 (dd, J = 3.4, 1.9 Hz, 1H), 7.06 (d, J = 3.4 Hz, 1H), 7.17-7.34 (m, 2H), 7.70-7.87 (m, 4H), 8.61 (s, 1H), 8.99 (broad s, 1H), 10.04 (broad s, 1H).<br>Mass spectrum (LC-MS-ES+/−): m/z 340 [M + H]⁺ |
| 69 | ¹H NMR spectrum (DMSO-d6, δ in ppm): 6.66 (dd, J = 3.4, 1.8 Hz, 1H), 7.07 (d, J = 3.4 Hz, 1H), 7.20 (m, 1H), 7.37-7.47 (m, 1H), 7.58 (dd, J = 8.2, 1.6 Hz, 1H), 7.78 (m, 2H), 7.81-7.86 (m, 1H), 8.36 (dd, J = 8.2, 1.6 Hz, 1H), 8.62 (s, 1H), 8.96-9.03 (broad s, 1H), 9.92 (broad s, 1H).<br>Mass spectrum (LC-MS-ES+/−): m/z 338 [M + H]⁺ |
| 70 | ¹H NMR spectrum (DMSO-d6, δ in ppm): 7.06 (m, 1H), 7.40 (ddd, J = 10.4, 9.1, 5.1 Hz, 1H), 7.46 (d, J = 0.9 Hz, 1H), 7.85 (d, J = 9.6 Hz, 1H), 7.85 (dd, J = 9.6, 1.7 Hz, 1H), 7.97 (m, 1H), 8.31 (d, J = 0.9 Hz, 1H), 8.72 (s, 1H), 9.37 (broad s, 1H), 9.91 (broad s, 1H).<br>Mass spectrum (LC-MS-ES+/−): m/z 341 [M + H]⁺ |
| 71 | ¹H NMR spectrum (DMSO-d6, δ in ppm): 7.17-7.25 (m, 1H), 7.38-7.47 (m, 2H), 7.58 (dd, J = 8.0, 1.4 Hz, 1H), 7.85 (d, J = 9.5 Hz, 1H), 7.92 (dd, J = 9.5, 1.7 Hz, 1H), 8.29-8.34 (m, 2H), 8.72 (s, 1H), 9.38 (broad s, 1H), 9.95 (broad s, 1H).<br>Mass spectrum (LC-MS-ES+/−): m/z 339 [M + H]⁺ |
| 72 | ¹H NMR spectrum (DMSO-d6, δ in ppm): 6.95-7.00 (m, 1H), 7.14-7.39 (m, 3H), 7.68-7.78 (m, 2H), 7.80-7.84 (m, 1H), 8.06-8.15 (m, 1H), 8.30 (broad s, 1H), 8.46 (s, 1H), 8.92 (broad s, 1H), 9.80 (broad s, 1H).<br>Mass spectrum (LC-MS-ES+/−): m/z 322 [M + H]⁺ |
| 73 | ¹H NMR spectrum (DMSO-d6, δ in ppm): 6.96-7.11 (m, 2H), 7.33-7.46 (m, 1H), 7.69-7.79 (m, 2H), 7.79-7.85 (m, 1H), 7.98-8.07 (m, 1H), 8.29 (broad s, 1H), 8.49 (s, 1H), 8.92 (broad s, 1H), 9.85 (broad s, 1H).<br>Mass spectrum (LC-MS-ES+/−): m/z 340 [M + H]⁺ |
| 74 | ¹H NMR spectrum (DMSO-d6, δ in ppm): 6.93-7.00 (m, 1H), 7.20-7.29 (m, 2H), 7.67-7.86 (m, 4H), 8.29 (broad s, 1H), 8.47 (s, 1H), 8.92 (broad s, 1H), 10.04 (broad s, 1H).<br>Mass spectrum (LC-MS-ES+/−): m/z 340 [M + H]⁺ |
| 75 | ¹H NMR spectrum (DMSO-d6, δ in ppm): 6.98 (dd, J = 1.9, 0.9 Hz, 1H), 7.20 (td, J = 7.9, 1.6 Hz, 1H), 7.42 (td, J = 7.9 1.6 Hz, 1H), 7.58 (dd, J = 7.9, 1.6 Hz, 1H), 7.72 (dd, J = 9.5, 1.7 Hz, 1H), 7.76 (d, J = 9.5 Hz, 1H), 7.82 (t, J = 1.9 Hz, 1H), 8.30 (broad s, 1H), 8.37 (dd, J = 7.9, 1.6 Hz, 1H), 8.49 (s, 1H), 8.93 (broad s, 1H), 9.93 (broad s, 1H).<br>Mass spectrum (LC-MS-ES+/−): m/z 338 [M + H]⁺ |
| 76 | ¹H NMR spectrum (DMSO-d6, δ in ppm): 4.49 (d, J = 5.3 Hz, 2H), 5.30 (t, J = 5.3 Hz, 1H), 6.47 (d, J = 3.4 Hz, 1H), 6.99 (d, J = 3.4 Hz, 1H), 7.21-7.28 (m, 2H), 7.73-7.83 (m, 3H), 8.62 (s, 1H), 8.94 (broad s, 1H), 10.03 (broad s, 1H).<br>Mass spectrum (LC-MS-ES+/−): m/z 368 [M + H]⁻, m/z 370 [M + H]⁺ |
| 77 | ¹H NMR spectrum (DMSO-d6, δ in ppm): 7.14-7.40 (m, 3H), 7.82 (d, J = 9.5 Hz, 1H), 7.97 (dd, J = 9.5, 1.7 Hz, 1H), 8.03-8.15 (m, 1H), 8.63 (broad m, 1H), 8.71 (s, 1H), 9.31 (broad s, 1H), 9.84 (broad s, 1H), 14.19-14.39 (broad m, 1H).<br>Mass spectrum (LC-MS-ES+/−): m/z 321 [M + H]⁻, m/z 323 [M + H]⁺ |
| 78 | ¹H NMR spectrum (DMSO-d6, δ in ppm): 7.17-7.24 (m, 1H), 7.38-7.45 (m, 1H), 7.58 (dd, J = 8.0.1.4 Hz, 1H), 7.81 (d, J = 9.5 Hz, 1H), 7.99 (dd, J = 9.5, 1.7 Hz, 1H), 8.35 (dd, J = 8.2, 1.4 Hz, 1H), 8.61-8.67 (broad m, 1H), 8.73 (s, 1H), 9.33 (broad s, 1H), 9.95 (broad s, 1H), 14.14-14.42 (broad m, 1H).<br>Mass spectrum (LC-MS-ES+/−): m/z 337 [M + H]⁻, m/z 339 [M + H]⁺ |
| 79 | ¹H NMR spectrum (DMSO-d6, δ in ppm): 7.36-7.46 (m, 2H), 7.72-7.83 (m, 2H), 7.87 (dd, J = 7.8, 1.2 Hz, 1H), 7.94-8.06 (m, 3H), 8.14 (dd, J = 9.8, 1.7 Hz, 1H), 8.64-8.78 (m, 2H), 9.43 (s, 1H), 10.46 (broad s, 1H).<br>Mass spectrum (LC-MS-ES+/−): m/z 340 [M + H]⁺ |
| 80 | ¹H NMR spectrum (DMSO-d6, δ in ppm): 6.89-7.03 (m, 2H), 7.25 (d, J = 7.4 Hz, 1H), 7.65-8.04 (m, 7H), 8.69 (s, 1H), 9.33 (s, 1H), 10.90 (broad s, 1H).<br>Mass spectrum (LC-MS-ES+/−): m/z 366 [M + H]⁺ |
| 81 | ¹H NMR spectrum (DMSO-d6, δ in ppm): 6.88 (d, J = 8.7 Hz, 1H), 7.16-7.40 (m, 4H), 7.6 (broad m, 2H), 7.82-7.98 (m, 3H), 8.00-8.10 (m, 1H), 8.67 (s, 1H), 9.27 (s, 1H), 9.94 (broad s, 1H).<br>Mass spectrum (LC-MS-ES+/−): m/z 348 [M + H]⁺ |
| 82 | ¹H NMR spectrum (DMSO-d6, δ in ppm): 6.89 (d, J = 8.7 Hz, 1H), 7.02-7.12 (m, 1H), 7.22 (d, J = 7.4 Hz, 1H), 7.41 (ddd, J = 10.3, 9.2, 5.0 Hz, 1H), 7.6 (m, 2H), 7.84-8.02 (m, 4H), 8.69 (s, 1H), 9.27 (s, 1H), 9.96 (broad s, 1H).<br>Mass spectrum (LC-MS-ES+/−): m/z 366 [M + H]⁺ |
| 83 | ¹H NMR spectrum (DMSO-d6, δ in ppm): 6.98 (d, J = 8.4 Hz, 1H), 7.20-7.35 (m, 3H), 7.69-7.78 (m, 1H), 7.87-8.01 (m, 3H), 7.95 (broad m, 2H), 8.69 (s, 1H), 9.31 (s, 1H), 10.23 (broad s, 1H).<br>Mass spectrum (LC-MS-ES+/−): m/z 366 [M + H]⁺ |

TABLE 2-continued

| Ex | Characterizations |
|---|---|
| 84 | ¹H NMR spectrum (DMSO-d6, δ in ppm): 6.89 (d, J = 8.7 Hz, 1H), 7.17-7.27 (m, 2H), 7.38-7.48 (m, 1H), 7.59 (dd, J = 7.9, 1.4 Hz, 1H), 7.60 (m, 2H), 7.83-7.98 (m, 3H), 8.32 (dd, J = 8.2, 1.4 Hz, 1H), 8.68 (s, 1H), 9.28 (s, 1H), 10.01 (broad s, 1H). Mass spectrum (LC-MS-ES+/−): m/z 364 [M + H]⁺ |
| 85 | ¹H NMR spectrum (DMSO-d6, δ in ppm): 6.47 (m, 1H), 6.87 (m, 1H), 7.19 (td, J = 7.9, 1.6 Hz, 1H), 7.32 (m, 1H), 7.41 (td, J = 7.9, 1.6 Hz, 1H), 7.58 (dd, J = 7.9, 1.6 Hz, 1H), 7.65 (d, J = 9.5 Hz, 1H), 7.71 (dd, J = 9.5, 1.6 Hz, 1H), 8.39 (dd, J = 7.9, 1.6 Hz, 1H), 8.46 (s, 1H), 8.76 (broad s, 1H), 9.91 (broad s, 1H), 11.05 (broad m, 1H). Mass spectrum (LC-MS-ES+/−): m/z 335 [M + H]⁻, m/z 337 [M + H]⁺ |
| 86 | ¹H NMR spectrum (DMSO-d6, δ in ppm): 6.77 (d, J = 2.3 Hz, 1H), 7.15-7.41 (m, 3H), 7.70-7.95 (m, 3H), 8.10 (m, 1H), 8.56 (s, 1H), 9.08 (broad s, 1H), 9.81 (broad s, 1H), 13.04 (broad m, 1H). Mass spectrum (LC-MS-ES+/−): m/z 320 [M + H]⁻, m/z 322 [M + H]⁺ |
| 87 | ¹H NMR spectrum (DMSO-d6, δ in ppm): 6.78 (broad s, 1H), 7.20 (td, J = 8.0, 1.4 Hz, 1H), 7.36-7.47 (m, 1H), 7.58 (dd, J = 8.0, 1.4 Hz, 1H), 7.75 (d, J = 9.5 Hz, 1H), 7.86 (broad s, 1H), 7.91 (broad d, J = 9.5 Hz, 1H), 8.37 (dd, J = 8.0, 1.4 Hz, 1H), 8.59 (s, 1H), 9.09 (broad s, 1H), 9.94 (s, 1H), 13.06 (broad s, 1H). Mass spectrum (LC-MS-ES+/−): m/z 336 [M + H]⁻, m/z 338 [M + H]⁺ |
| 88 | ¹H NMR spectrum (DMSO-d6, δ in ppm): 6.66 (dd, J = 3.4, 1.7 Hz, 1H), 6.93 (tt, J = 9.4, 2.4 Hz, 1H), 7.05 (d, J = 3.4 Hz, 1H), 7.67-7.80 (m, 4H) 7.83 (m, 1H), 8.60 (s, 1H), 8.99 (broad s, 1H), 10.74 (broad s, 1H). Mass spectrum (LC-MS-ES+/−): m/z 338 [M + H]⁻, m/z 340 [M + H]⁺ |
| 89 | ¹H NMR spectrum (DMSO-d6, δ in ppm): 6.94 (tt, J = 9.5, 2.2 Hz, 1H), 7.46 (d, J = 0.9 Hz, 1H), 7.75 (m, 2H), 7.81 (d, J = 9.6 Hz, 1H), 7.92 (dd, J = 9.6, 1.9 Hz, 1H), 8.31 (d, J = 0.9 Hz, 1H), 8.71 (broad s, 1H), 9.38 (broad s, 1H), 10.81 (broad s, 1H). Mass spectrum (LC-MS-ES+/−): m/z 339 [M + H]⁻, m/z 341 [M + H]⁺ |
| 90 | ¹H NMR spectrum (DMSO-d6, δ in ppm): 7.16-7.39 (m, 3H), 7.46 (d, J = 0.8 Hz, 1H), 7.84 (d, J = 9.5 Hz, 1H), 7.92 (dd, J = 9.6, 1.9 Hz, 1H), 8.05 (m, 1H), 8.31 (d, J = 0.8 Hz, 1H), 8.69 (s, 1H), 9.37 (broad s, 1H), 9.87 (broad s, 1H). Mass spectrum (LC-MS-ES+/−): m/z 323 [M + H]⁺ |
| 91 | ¹H NMR spectrum (DMSO-d6, δ in ppm): 7.18-7.33 (m, 2H), 7.46 (s, 1H), 7.74 (m, 1H), 7.84 (d, J = 9.5 Hz, 1H), 7.92 (d, J = 9.5 Hz, 1H), 8.31 (s, 1H), 8.70 (s, 1H), 9.37 (s, 1H), 10.12 (s, 1H), (broad signals) Mass spectrum (LC-MS-ES+/−): m/z 339 [M + H]⁻, m/z 341 [M + H]⁺ |
| 92 | ¹H NMR spectrum (DMSO-d6, δ in ppm): 4.49 (d, J = 5.6 Hz, 2H), 5.30 (t, J = 5.6 Hz, 1H), 6.46 (d, J = 3.4 Hz, 1H), 6.92 (tt, J = 9.3, 2.4 Hz, 1H), 6.98 (d, J = 3.4 Hz, 1H), 7.65-7.83 (m, 4H), 8.64 (s, 1H), 8.98 (broad s, 1H), 10.74 (broad s, 1H). Mass spectrum (LC-MS-ES+/−): m/z 368 [M + H]⁻, m/z 370 [M + H]⁺ |
| 93 | ¹H NMR spectrum (DMSO-d6, δ in ppm): 4.48 (d, J = 5.3 Hz, 2H), 5.30 (t, J = 5.3 Hz, 1H), 6.47 (d, J = 3.3 Hz, 1H), 6.96-7.11 (m, 1H), 6.99 (d, J = 3.3 Hz, 1H), 7.35-7.46 (m, 1H), 7.76 (m, 2H), 7.96-8.05 (m, 1H), 8.64 (s, 1H), 8.95 (broad s, 1H), 9.85 (broad s, 1H). Mass spectrum (LC-MS-ES+/−): m/z 368 [M + H]⁻, m/z 370 [M + H]⁺ |
| 94 | ¹H NMR spectrum (DMSO-d6, δ in ppm): 7.19-7.28 (m, 2H), 7.65-7.72 (m, 2H), 7.75-7.86 (m, 3H), 8.59 (s, 1H), 8.99 (broad s, 1H), 10.27-11.48 (broad m, 1H). Mass spectrum (LC-MS-ES+/−): m/z 338 [M + H]⁻, m/z 340 [M + H]⁺ |
| 95 | ¹H NMR spectrum (DMSO-d6, δ in ppm): 7.05 (m, 1H), 7.40 (m, 1H), 7.79 (d, J = 9.5 Hz, 1H), 7.94-8.06 (m, 2H), 8.71 (s, 1H), 8.73 (s, 1H), 9.32 (broad s, 1H), 9.89 (broad s, 1H), 14.27 (broad s, 1H). Mass spectrum (LC-MS-ES+/−): m/z 339 [M + H]⁻, m/z 341 [M + H]⁺ |
| 96 | ¹H NMR spectrum (DMSO-d6, δ in ppm): 7.20-7.30 (m, 2H) 7.73-7.82 (m, 2H) 8.00 (dd, J = 9.5, 1.7 Hz 1H) 8.71 (s, 2H) 9.32 (broad s, 1H) 10.08 (broad s, 1H) 14.25 (broad s, 1H) Mass spectrum (LC-MS-ES+/−): m/z 339 [M + H]⁻, m/z 341 [M + H]⁺ |
| 97 | ¹H NMR spectrum (DMSO-d6, δ in ppm): 6.93 (tt, J = 9.4, 2.2 Hz, 1H), 7.68-7.82 (m, 3H), 7.88 (dd, J = 9.5, 1.7 Hz, 1H), 8.43 (broad m, 1H), 8.62 (s, 1H), 9.21 (broad s, 1H), 10.76 (broad s, 1H), 15.31 (broad m, 1H). Mass spectrum (LC-MS-ES+/−): m/z 339 [M + H]⁻, m/z 341 [M + H]⁺ |
| 98 | ¹H NMR spectrum (DMSO-d6, δ in ppm): 7.15-7.41 (m, 3H), 7.81 (d, J = 9.5 Hz, 1H), 7.89 (dd, J = 9.5, 1.7 Hz, 1H), 8.10 (m, 1H), 8.43 (broad m, 1H), 8.61 (s, 1H), 9.20 (broad s, 1H), 9.82 (broad s, 1H), 15.31 (broad m, 1H). Mass spectrum (LC-MS-ES+/−): m/z 321 [M + H]⁻, m/z 323 [M + H]⁺ |
| 99 | ¹H NMR spectrum (DMSO-d6, δ in ppm): 7.05 (m, 1H), 7.40 (m, 1H), 7.82 (d, J = 9.5 Hz, 1H), 7.82 (dd, J = 9.5, 1.7 Hz, 1H), 8.01 (m, 1H), 8.43 (broad m, 1H), 8.64 (s, 1H), 9.20 (broad s, 1H), 9.88 (broad s, 1H), 15.31 (broad m, 1H). Mass spectrum (LC-MS-ES+/−): m/z 339 [M + H]⁻, m/z 341 [M + H]⁺ |
| 100 | ¹H NMR spectrum (DMSO-d6, δ in ppm): 7.20 (m, 1H), 7.42 (m, 1H), 7.59 (m, 1H), 7.77-7.97 (m, 2H), 8.31-8.51 (m, 2H), 8.66 (s, 1H), 9.21 (s, 1H), 9.95 (s, 1H), 15.33 (broad m, 1H), (broad signals) Mass spectrum (LC-MS-ES+/−): m/z 337 [M + H]⁻, m/z 339 [M + H]⁺ |

The compounds according to the invention underwent pharmacological tests to determine their modulatory effect on NOT.

Evaluation of the In Vitro Activity on N2A Cells

The activity of the compounds according to the invention was evaluated on a cell line (N2A) endogenously expressing the murine Nurr1 receptor and stably transfected with the NOT binding response element (NBRE) coupled to the luciferase reporter gene. The $EC_{50}$ values are between 0.01 and 1000 nM. The tests were performed according to the procedure described hereinbelow.

The cell line Neuro-2A is obtained from a standard commercial source (ATCC). The clone Neuro-2A was obtained from a spontaneous tumour originating from a strain of albino mice A by R. J Klebe et al. This line Neuro-2A is then stably transfected with 8NBRE-luciferase. The N2A-8NBRE cells are cultured to the point of confluence in 75 cm² culture flasks containing DMEM supplemented with 10% foetal calf serum, 4.5 g/L of glucose and 0.4 mg/ml of geneticin. After culturing for one week, the cells are recovered with 0.25% trypsin for 30 seconds and then resuspended in DMEM without phenol red, containing 4.5 g/L of glucose and 10% Hyclone defatted serum, and placed in white, transparent-based 96-well plates. The cells are deposited at a rate of 60 000 per well in 75 μL for 24 hours before adding the products. The products are applied in 25 μL and incubated for a further 24 hours. On the day of measurement, an equivalent volume (100 μL) of Steadylite is added to each well, and the wells are then left for 30 minutes to obtain complete lysis of the cells and maximum production of the signal. The plates are then measured in a microplate luminescence counter, after having been sealed with an adhesive film. The products are prepared in the form of a $10^{-2}$ M stock solution, and then diluted in 100% of DMSO. Each concentration of product is prediluted in culture medium before incubation with the cells thus containing 0.625% final of DMSO.

For example, compounds 3, 17, 24, 29, 45 and 53 gave an $EC_{50}$ value of 0.9 nM, 26.8 nM, 0.9 nM, 1.1 nM, 1.2 nM and 0.4 nM, respectively.

It is thus seen that the compounds according to the invention have a modulatory effect on NOT.

The compounds according to the invention may thus be used for the preparation of medicaments for their therapeutic application in the treatment or prevention of diseases involving the NOT receptors.

Thus, according to another of its aspects, a subject of the invention is medicaments comprising a compound of formula (I), or an addition salt thereof with a pharmaceutically acceptable acid.

These medicaments find their therapeutic use especially in the treatment and prevention of neurodegenerative diseases, for instance Parkinson's disease, Alzheimer's disease, tauopathies (e.g. progressive supranuclear palsy, frontotemporal dementia, corticobasal degeneration, Pick's disease); cerebral trauma, for instance ischaemia and cranial trauma and epilepsy; psychiatric diseases, for instance schizophrenia, depression, substance dependency, and attention-deficit hyperactivity disorder; inflammatory diseases of the central nervous system, for instance multiple sclerosis, encephalitis, myelitis and encephalomyelitis and other inflammatory diseases, for instance vascular pathologies, atherosclerosis, joint inflammations, arthrosis, rheumatoid arthritis; osteoarthritis, Crohn's disease, ulcerative colitis; allergic inflammatory diseases such as asthma, autoimmune diseases, for instance type 1 diabetes, lupus, scleroderma, Guillain-Barré syndrome, Addison's disease and other immune-mediated diseases; osteoporosis; cancers.

Thus, one subject of the present invention is directed towards a compound of formula (I) as defined previously, for the treatment of the abovementioned diseases, complaints and disorders.

According to another of its aspects, the present invention relates to the use of a compound of formula (I) as defined previously, for the preparation of a medicament for treating or preventing one of the diseases, complaints or disorders mentioned above.

These compounds may also be used as a treatment combined with grafts and/or transplantations of stem cells.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above complaints or diseases.

The appropriate unit forms of administration include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages are not outside the context of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration, to a patient, of an effective dose of a compound according to the invention, or a pharmaceutically acceptable salt thereof.

It is understood that all the subjects of the invention defined above, especially the medicaments, pharmaceutical compositions and treatment methods, also apply more particularly to the subgroups of compounds previously defined.

What is claimed is:
1. A compound of formula (I):

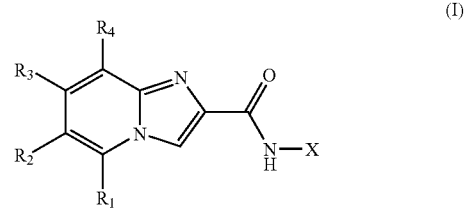

wherein:
- X represents a phenyl group optionally substituted with one or more groups chosen, independently of each other, from the following atoms or groups: halogen, ($C_1$-$C_6$) alkoxy, ($C_1$-$C_6$)alkyl, NRaRb, cyano, and ($C_1$-$C_6$) alkoxycarbonyl, the groups ($C_1$-$C_6$)alkyl and ($C_1$-$C_6$) alkoxy being optionally substituted with one or more halogen atoms;
- $R_1$ represents a hydrogen atom, a halogen, a group ($C_1$-$C_6$) alkoxy, a group ($C_1$-$C_6$)alkyl or a group NRaRb; the alkyl and alkoxy groups possibly being substituted with one or more halogen, hydroxyl, amino, or a group ($C_1$-$C_6$)alkoxy;
- $R_2$ represents an unsaturated, partially saturated or totally saturated aromatic heterocyclic group, optionally substituted with one or more groups chosen, independently of each other, from the following atoms or groups: hydroxyl, ($C_1$-$C_6$)alkoxy, halogen, cyano, NRaRb, —CO—$R_5$, —CO—NR$_6$R$_7$, —CO—O—$R_8$, —NR$_9$—CO—$R_{10}$, ($C_3$-$C_7$)cycloalkyl($C_1$-$C_6$)alkyl, ($C_3$-$C_7$)cycloalkyl($C_1$-$C_6$)alkoxy, a group ($C_1$-$C_6$)alkyl, optionally substituted with one or more hydroxyl or NRaRb, an oxido group, whereby $R_2$ is linked to the imidazo[1,2-a]pyridine moiety of formula (I) via a carbon-carbon bond;
- $R_3$ represents a hydrogen atom, a group ($C_1$-$C_6$)alkyl, a group ($C_1$-$C_6$)alkoxy or a halogen atom;
- $R_4$ represents a hydrogen atom, a group ($C_1$-$C_4$)alkyl, a group ($C_1$-$C_4$)alkoxy or a fluorine atom;
- $R_5$ represents a hydrogen atom, a phenyl group or a group ($C_1$-$C_6$)alkyl;
- $R_6$ and $R_7$, which may be identical or different, represent a hydrogen atom or a group ($C_1$-$C_6$)alkyl or form, with the nitrogen atom, a 4- to 7-membered ring optionally including another heteroatom chosen from N, O and S;
- $R_8$ represents a group ($C_1$-$C_6$)alkyl;
- $R_9$ and $R_{10}$, which may be identical or different, represent a hydrogen atom or a group ($C_1$-$C_6$)alkyl;
- Ra and Rb are, independently of each other, hydrogen or ($C_1$-$C_6$)alkyl or form, with the nitrogen atom that bears them, a 4- to 7-membered ring, optionally including another heteroatom chosen from N, O and S;

or an acid addition salt thereof;
with the exception of N-(4-bromophenyl)-6-(1-methyl-2-piperidinyl)imidazo[1,2-a]pyridine-2-carboxamide.

2. The compound of formula (I) according to claim 1, wherein:
- X represents a phenyl group optionally substituted with one or more halogen atoms or cyano groups;

or an acid addition salt thereof.

3. The compound of formula (I) according to claim 1, wherein:
- $R_2$ represents a pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine group, optionally substituted with one or more groups chosen from the following atoms or groups: hydroxyl, ($C_1$-$C_6$)alkoxy, oxido, halogen, —NRaRb, and ($C_1$-$C_6$)alkyl which is itself optionally substituted with a hydroxyl group; and
- Ra and Rb are, independently of each other, hydrogen or ($C_1$-$C_6$)alkyl;

or an acid addition salt thereof.

4. The compound of formula (I) according to claim 1, wherein:
- $R_2$ represents a pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine group, optionally substituted with one or more groups chosen from the following atoms or groups: hydroxyl, ($C_1$-$C_6$)alkoxy, oxido, halogen, —NRaRb, and ($C_1$-$C_6$)alkyl which is itself optionally substituted with a hydroxyl group; and
- Ra and Rb are, independently of each other, hydrogen or ($C_1$-$C_6$)alkyl;

or an acid addition salt thereof.

5. The compound of formula (I) according to claim 1, wherein:
- $R_2$ represents an indole, isoindole, benzimidazole, indazole, indolizine, benzofuran, isobenzofuran, benzothiophene, benzo[c]thiophen, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, tetrazolopyrimidine, pyrrolopyrazine, imidazopyrazine, pyrazolopyrazine, triazolopyrazine, tetrazolopyrazine, pyrrolopyridazine, imidazopyridazine, pyrazolopyridazine, triazolopyridazine, tetrazolopyridazine, pyrrolotriazine, imidazotriazine, pyrazolotriazine, triazolotriazine, tetrazolotriazine, furopyridine, furopyrimidine, furopyrazine, furopyridazine, furotriazine, oxazolopyridine, oxazolopyrimidine, oxazolopyrazine, oxazolopyridazine, oxazolotriazine, isoxazolopyridine, isoxazolopyrimidine, isoxazolopyrazine, isoxazolopyridazine, isoxazolotriazine, oxadiazolopyridine, oxadiazolopyrimidine, oxadiazolopyrazine, oxadiazolopyridazine, oxadiazolotriazine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, thiazolotriazine, isothiazolopyridine, isothiazolopyrimidine, isothiazolopyrazine, isothiazolopyridazine, isothiazolotriazine, thiadiazolopyridine, thiadiazolopyrimidine, thiadiazolopyrazine, thiadiazolopyridazine, thiadiazolotriazine, benzothiazole, benzoisothiazole or benzothiadiazole group, optionally substituted with one or more groups chosen from the following atoms or groups: hydroxyl, ($C_1$-$C_6$)alkoxy, oxido, halogen, —NRaRb, and ($C_1$-$C_6$)alkyl which is itself optionally substituted with a hydroxyl group; and
- Ra and Rb are, independently of each other, hydrogen or ($C_1$-$C_6$)alkyl;

or an acid addition salt thereof.

6. The compound of formula (I) according to claim 1, wherein:
- $R_2$ represents a dioxolane, pyridine, imidazole, pyrazole, triazole, pyrrole, furan, oxazole, indole, imidazoline, thiophene, pyrazine, pyrimidine or thiazole group optionally substituted with one or more groups chosen from the following atoms or groups: hydroxyl, ($C_1$-$C_6$) alkoxy, oxido, halogen, —NRaRb, and ($C_1$-$C_6$)alkyl which is itself optionally substituted with a hydroxyl group, and
- Ra and Rb are, independently of each other, hydrogen or ($C_1$-$C_6$)alkyl, or an acid addition salt thereof.

7. The compound of formula (I) according to claim 1, wherein $R_1$ represents a hydrogen atom or a group ($C_1$-$C_6$) alkyl;

or an acid addition salt thereof.

8. The compound of formula (I) according to claim 1, wherein $R_3$ and $R_4$ represent a hydrogen atom;

or an acid addition salt thereof.

9. The compound of formula (I) according to claim 1, wherein:
- X represents a phenyl group optionally substituted with one or more fluorine or chlorine atoms or with a cyano group;
- $R_2$ represents a dioxolane, pyridine, imidazole, pyrazole, triazole, pyrrole, furan, oxazole, indole, imidazoline, thiophene, pyrazine, pyrimidine or thiazole group, optionally substituted with one or more hydroxyl, methyl, hydroxymethyl, methoxy, halogen, $NH_2$, $(C_1$-$C_6)$alkyl or oxido groups,
- $R_1$ represents a hydrogen atom or a methyl group; and
- $R_3$ and $R_4$ represent a hydrogen atom;

or an acid addition salt thereof.

10. The compound of formula (I) according to claim 1, selected from the group consisting of:
- 6-(1,3-Dioxolan-2-yl)-N-phenylimidazo[1,2-a]pyridine-2-carboxamide;
- N-Phenyl-6-(pyrid-3-yl)imidazo[1,2-a]pyridine-2-carboxamide;
- N-Phenyl-6-(pyrid-2-yl)imidazo[1,2-a]pyridine-2-carboxamide;
- 6-[5-(Hydroxymethyl)pyrid-3-yl]-N-phenylimidazo[1,2-a]pyridine-2-carboxamide;
- 6-[4-(Hydroxymethyl)pyrid-2-yl]-N-phenylimidazo[1,2-a]pyridine-2-carboxamide and the hydrochloride (1:1) thereof;
- 6-(6-Aminopyrid-2-yl)-N-phenylimidazo[1,2-a]pyridine-2-carboxamide and the hydrochloride (1:1) thereof;
- 6-(1H-Imidazol-4-yl)-N-phenylimidazo[1,2-a]pyridine-2-carboxamide and the hydrochloride (1:1) thereof;
- N-Phenyl-6-(1H-pyrazol-3-yl)imidazo[1,2-a]pyridine-2-carboxamide;
- N-Phenyl-6-(1H-1,2,4-triazol-3-yl)imidazo[1,2-a]pyridine-2-carboxamide;
- N-Phenyl-6-(1H-pyrrol-3-yl)imidazo[1,2-a]pyridine-2-carboxamide;
- 6-(2-Methyl-1H-imidazol-4-yl)-N-phenylimidazo[1,2-a]pyridine-2-carboxamide;
- 6-(3-Furyl)-N-phenylimidazo[1,2-a]pyridine-2-carboxamide;
- 6-(1H-Imidazol-1-yl)-N-phenylimidazo[1,2-a]pyridine-2-carboxamide and the trifluoroacetate (1:1) thereof;
- 6-(Oxazol-5-yl)-N-phenylimidazo[1,2-a]pyridine-2-carboxamide;
- 6-(2-Aminothiazol-4-yl)-N-phenylimidazo[1,2-a]pyridine-2-carboxamide;
- 6-(2-Methyl-1,3-dioxolan-2-yl)-N-phenylimidazo[1,2-a]pyridine-2-carboxamide;
- 6-(4,5-Dihydro-1H-imidazol-2-yl)-N-phenylimidazo[1,2-a]pyridine-2-carboxamide and the hydrochloride (1:1) thereof;
- 6-(6-Methoxypyrid-2-yl)-N-phenylimidazo[1,2-a]pyridine-2-carboxamide;
- 5-Methyl-N-phenyl-6-(pyrid-2-yl)imidazo[1,2-a]pyridine-2-carboxamide;
- 6-(2-Amino-1H-imidazol-4-yl)-N-phenylimidazo[1,2-a]pyridine-2-carboxamide and the trifluoroacetate (1:1) thereof;
- 6-(2-Aminothiazol-5-yl)-N-phenylimidazo[1,2-a]pyridine-2-carboxamide;
- 6-(6-Hydroxypyrid-2-yl)-N-phenylimidazo[1,2-a]pyridine-2-carboxamide;
- N-Phenyl-6-(1H-1,2,3-triazol-4-yl)imidazo[1,2-a]pyridine-2-carboxamide;
- N-(3,5-Difluorophenyl)-6-(furan-3-yl)imidazo[1,2-a]pyridine-2-carboxamide;
- N-(3-Fluorophenyl)-6-(furan-3-yl)imidazo[1,2-a]pyridine-2-carboxamide;
- 6-(2-Furyl)-N-phenylimidazo[1,2-a]pyridine-2-carboxamide;
- 6-[6-(Hydroxymethyl)pyrid-2-yl]-N-phenylimidazo[1,2-a]pyridine-2-carboxamide and the hydrochloride (1:1) thereof;
- 6-(1-Oxidopyrid-3-yl)-N-phenylimidazo[1,2-a]pyridine-2-carboxamide and the hydrochloride (1:1) thereof;
- N-Phenyl-6-(1H-pyrazol-4-yl)imidazo[1,2-a]pyridine-2-carboxamide;
- 6-(1H-Imidazol-2-yl)-N-phenylimidazo[1,2-a]pyridine-2-carboxamide hydrochloride (1:1);
- 6-(1-Methyl-1H-imidazol-4-yl)-N-phenylimidazo[1,2-a]pyridine-2-carboxamide;
- 6-(Oxazol-2-yl)-N-phenylimidazo[1,2-a]pyridine-2-carboxamide;
- N-(3,5-Difluorophenyl)-6-(pyrid-2-yl)imidazo[1,2-a]pyridine-2-carboxamide;
- N-Phenyl-6-(pyrid-4-yl)imidazo[1,2-a]pyridine-2-carboxamide;
- 6-(1H-Indol-3-yl)-N-phenylimidazo[1,2-a]pyridine-2-carboxamide;
- N-Phenyl-6-(thiophen-2-yl)imidazo[1,2-a]pyridine-2-carboxamide;
- N-Phenyl-6-(pyrazin-2-yl)imidazo[1,2-a]pyridine-2-carboxamide;
- 6-(1-Oxidopyrid-2-yl)-N-phenylimidazo[1,2-a]pyridine-2-carboxamide;
- N-Phenyl-6-(pyrimidin-5-yl)imidazo[1,2-a]pyridine-2-carboxamide;
- N-Phenyl-6-(thien-3-yl)imidazo[1,2-a]pyridine-2-carboxamide;
- 6-(5-Fluoro-2-furyl)-N-phenylimidazo[1,2-a]pyridine-2-carboxamide;
- N-(3-Fluorophenyl)-6-(pyrid-2-yl)imidazo[1,2-a]pyridine-2-carboxamide;
- N-(2-Fluorophenyl)-6-(pyrid-2-yl)imidazo[1,2-a]pyridine-2-carboxamide;
- N-(2,5-Difluorophenyl)-6-(pyrid-2-yl)imidazo[1,2-a]pyridine-2-carboxamide;
- N-(2,3-Difluorophenyl)-6-(pyrid-2-yl)imidazo[1,2-a]pyridine-2-carboxamide;
- 6-(6-Aminopyrid-2-yl)-N-(3-fluorophenyl)imidazo[1,2-a]pyridine-2-carboxamide;
- N-(3-Fluorophenyl)-6-(1H-pyrrol-3-yl)imidazo[1,2-a]pyridine-2-carboxamide;
- N-(3-Fluorophenyl)-6-(1H-pyrazol-3-yl)imidazo[1,2-a]pyridine-2-carboxamide;
- N-(3-Fluorophenyl)-6-(furan-2-yl)imidazo[1,2-a]pyridine-2-carboxamide;
- N-(3-Fluorophenyl)-6-(oxazol-2-yl)imidazo[1,2-a]pyridine-2-carboxamide;
- N-Phenyl-6-(pyrimidin-2-yl)imidazo[1,2-a]pyridine-2-carboxamide;
- N-(3-Fluorophenyl)-6-(1H-imidazol-4-yl)imidazo[1,2-a]pyridine-2-carboxamide;
- N-(3-Fluorophenyl)-6-(1H-1,2,4-triazol-3-yl)imidazo[1,2-a]pyridine-2-carboxamide;
- 6-(2-Aminothiazol-4-yl)-N-(3-fluorophenyl)imidazo[1,2-a]pyridine-2-carboxamide;
- N-(3-Fluorophenyl)-6-(1H-1,2,3-triazol-4-yl)imidazo[1,2-a]pyridine-2-carboxamide;
- N-(3-Fluorophenyl)-6-(1H-pyrazol-4-yl)imidazo[1,2-a]pyridine-2-carboxamide;
- N-(3-Fluorophenyl)-6-[5-(hydroxymethyl)furan-2-yl]imidazo[1,2-a]pyridine-2-carboxamide;

6-[2-(Hydroxymethyl)-1H-imidazol-4-yl]-N-phenylimidazo[1,2-a]pyridine-2-carboxamide;
N-(3,5-Difluorophenyl)-6-(6-methylpyrid-2-yl)imidazo[1,2-a]pyridine-2-carboxamide;
N-(2-Chlorophenyl)-6-(pyrid-2-yl)imidazo[1,2-a]pyridine-2-carboxamide;
N-(3,5-Difluorophenyl)-6-(1H-pyrrol-3-yl)imidazo[1,2-a]pyridine-2-carboxamide;
N-(2-Fluorophenyl)-6-(1H-pyrrol-3-yl)imidazo[1,2-a]pyridine-2-carboxamide;
N-(2,5-Difluorophenyl)-6-(1H-pyrrol-3-yl)imidazo[1,2-a]pyridine-2-carboxamide;
N-(2,3-Difluorophenyl)-6-(1H-pyrrol-3-yl)imidazo[1,2-a]pyridine-2-carboxamide;
N-(3,5-Difluorophenyl)-6-(1H-pyrazol-3-yl)imidazo[1,2-a]pyridine-2-carboxamide;
N-(2-Fluorophenyl)-6-(furan-2-yl)imidazo[1,2-a]pyridine-2-carboxamide;
N-(2,5-Difluorophenyl)-6-(furan-2-yl)imidazo[1,2-a]pyridine-2-carboxamide;
N-(2,3-Difluorophenyl)-6-(furan-2-yl)imidazo[1,2-a]pyridine-2-carboxamide;
N-(2-Chlorophenyl)-6-(furan-2-yl)imidazo[1,2-a]pyridine-2-carboxamide;
N-(2,5-Difluorophenyl)-6-(oxazol-2-yl)imidazo[1,2-a]pyridine-2-carboxamide;
N-(2-Chlorophenyl)-6-(oxazol-2-yl)imidazo[1,2-a]pyridine-2-carboxamide;
N-(2-Fluorophenyl)-6-(furan-3-yl)imidazo[1,2-a]pyridine-2-carboxamide;
N-(2,5-Difluorophenyl)-6-(furan-3-yl)imidazo[1,2-a]pyridine-2-carboxamide;
N-(2,3-Difluorophenyl)-6-(furan-3-yl)imidazo[1,2-a]pyridine-2-carboxamide;
N-(2-Chlorophenyl)-6-(furan-3-yl)imidazo[1,2-a]pyridine-2-carboxamide;
N-(2,3-Difluorophenyl)-6-[5-(hydroxymethyl)furan-2-yl]imidazo[1,2-a]pyridine-2-carboxamide;
N-(2-Fluorophenyl)-6-(1H-1,2,4-triazol-3-yl)imidazo[1,2-a]pyridine-2-carboxamide;
N-(2-Chlorophenyl)-6-(1H-1,2,4-triazol-3-yl)imidazo[1,2-a]pyridine-2-carboxamide;
N-(2-Cyanophenyl)-6-(pyrid-2-yl)imidazo[1,2-a]pyridine-2-carboxamide;
6-(6-Aminopyrid-2-yl)-N-(3,5-difluorophenyl)imidazo[1,2-a]pyridine-2-carboxamide and the dihydrochloride thereof;
6-(6-Aminopyrid-2-yl)-N-(2-fluorophenyl)imidazo[1,2-a]pyridine-2-carboxamide and the dihydrochloride thereof;
6-(6-Aminopyrid-2-yl)-N-(2,5-difluorophenyl)imidazo[1,2-a]pyridine-2-carboxamide and the dihydrochloride thereof;
6-(6-Aminopyrid-2-yl)-N-(2,3-difluorophenyl)imidazo[1,2-a]pyridine-2-carboxamide and the dihydrochloride thereof;
6-(6-Aminopyrid-2-yl)-N-(2-chlorophenyl)imidazo[1,2-a]pyridine-2-carboxamide and the dihydrochloride thereof;
N-(2-Chlorophenyl)-6-(1H-pyrrol-3-yl)imidazo[1,2-a]pyridine-2-carboxamide;
N-(2-Fluorophenyl)-6-(1H-pyrazol-3-yl)imidazo[1,2-a]pyridine-2-carboxamide;
N-(2-Chlorophenyl)-6-(1H-pyrazol-3-yl)imidazo[1,2-a]pyridine-2-carboxamide;
N-(3,5-Difluorophenyl)-6-(furan-2-yl)imidazo[1,2-a]pyridine-2-carboxamide;
N-(3,5-Difluorophenyl)-6-(oxazol-2-yl)imidazo[1,2-a]pyridine-2-carboxamide;
N-(2-Fluorophenyl)-6-(oxazol-2-yl)imidazo[1,2-a]pyridine-2-carboxamide;
N-(2,3-Difluorophenyl)-6-(oxazol-2-yl)imidazo[1,2-a]pyridine-2-carboxamide;
N-(3,5-Difluorophenyl)-6-[5-(hydroxymethyl)furan-2-yl]imidazo[1,2-a]pyridine-2-carboxamide;
N-(2,5-Difluorophenyl)-6-[5-(hydroxymethyl)furan-2-yl]imidazo[1,2-a]pyridine-2-carboxamide;
N-(2,3-Difluorophenyl)-6-(1H-imidazol-4-yl)imidazo[1,2-a]pyridine-2-carboxamide;
N-(2,5-Difluorophenyl)-6-(1H-1,2,4-triazol-3-yl)imidazo[1,2-a]pyridine-2-carboxamide;
N-(2,3-Difluorophenyl)-6-(1H-1,2,4-triazol-3-yl)imidazo[1,2-a]pyridine-2-carboxamide;
N-(3,5-Difluorophenyl)-6-(1H-1,2,3-triazol-4-yl)imidazo[1,2-a]pyridine-2-carboxamide;
N-(2-Fluorophenyl)-6-(1H-1,2,3-triazol-4-yl)imidazo[1,2-a]pyridine-2-carboxamide;
N-(2,5-Difluorophenyl)-6-(1H-1,2,3-triazol-4-yl)imidazo[1,2-a]pyridine-2-carboxamide; and
N-(2-Chlorophenyl)-6-(1H-1,2,3-triazol-4-yl)imidazo[1,2-a]pyridine-2-carboxamide;
or an acid addition salt thereof.

11. A pharmaceutical composition comprising a compound of formula (I) according to claim 1, or a pharmaceutically acceptable salt of this compound, and also at least one pharmaceutically acceptable excipient.

* * * * *